(12) United States Patent
Hsia

(10) Patent No.: US 12,036,246 B2
(45) Date of Patent: *Jul. 16, 2024

(54) COMPOSITIONS AND METHODS FOR ENHANCING CANCER CHEMOTHERAPY

(71) Applicant: Houn Simon Hsia, Tustin, CA (US)

(72) Inventor: Houn Simon Hsia, Tustin, CA (US)

(73) Assignee: Houn Simon Hsia, Tustin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/163,793

(22) Filed: Feb. 1, 2021

(65) Prior Publication Data

US 2021/0252076 A1    Aug. 19, 2021

Related U.S. Application Data

(62) Division of application No. 16/007,539, filed on Jun. 13, 2018, now Pat. No. 10,905,725.

(60) Provisional application No. 62/670,275, filed on May 11, 2018, provisional application No. 62/595,002, filed on Dec. 5, 2017, provisional application No. 62/519,096, filed on Jun. 13, 2017, provisional application No. 62/519,093, filed on Jun. 13, 2017.

(51) Int. Cl.
| | |
|---|---|
| *A61K 35/60* | (2006.01) |
| *A61K 31/192* | (2006.01) |
| *A61K 31/282* | (2006.01) |
| *A61K 31/337* | (2006.01) |
| *A61K 31/4409* | (2006.01) |
| *A61K 31/517* | (2006.01) |
| *A61K 31/519* | (2006.01) |
| *A61K 31/5377* | (2006.01) |
| *A61K 31/555* | (2006.01) |
| *A61K 33/04* | (2006.01) |
| *A61K 33/243* | (2019.01) |
| *A61K 45/06* | (2006.01) |
| *A61P 35/00* | (2006.01) |

(52) U.S. Cl.
CPC ............ *A61K 35/60* (2013.01); *A61K 31/192* (2013.01); *A61K 31/282* (2013.01); *A61K 31/337* (2013.01); *A61K 31/4409* (2013.01); *A61K 31/517* (2013.01); *A61K 31/519* (2013.01); *A61K 31/5377* (2013.01); *A61K 31/555* (2013.01); *A61K 33/04* (2013.01); *A61K 33/243* (2019.01); *A61K 45/06* (2013.01); *A61P 35/00* (2018.01)

(58) Field of Classification Search
CPC ........ A61P 35/00; A61K 35/60; A61K 45/06; A61K 31/4409; A61K 31/192; A61K 31/519; A61K 31/337; A61K 31/282; A61K 31/5377; A61K 31/555; A61K 31/517; A61K 33/04; A61K 33/243
See application file for complete search history.

(56) References Cited

U.S. PATENT DOCUMENTS

| | | | | |
|---|---|---|---|---|
| 6,077,828 | A * | 6/2000 | Abbruzzese | A23L 33/175 |
| | | | | 514/5.5 |
| 6,197,295 | B1 * | 3/2001 | Hsia | A23L 33/14 |
| | | | | 424/93.51 |
| 6,576,233 | B2 * | 6/2003 | Hsia | C12P 3/00 |
| | | | | 424/93.51 |
| 8,257,694 | B2 | 9/2012 | Daikeler | |
| 9,072,768 | B2 | 7/2015 | Ranganathan | |
| 10,206,861 | B2 | 2/2019 | Seiberg | |
| 10,905,723 | B2 | 2/2021 | Hsia | |
| 10,905,725 | B2 * | 2/2021 | Hsia | A61K 31/5377 |
| 2005/0013875 | A1 | 1/2005 | Kobayashi | |
| 2006/0034944 | A1 | 2/2006 | Ruslow | |
| 2006/0088574 | A1 | 4/2006 | Manning | |
| 2007/0116802 | A1 | 5/2007 | Germano | |
| 2011/0189220 | A1 | 8/2011 | Yang | |
| 2011/0195093 | A1 | 8/2011 | Gunn | |
| 2014/0294795 | A1 | 10/2014 | Hsia | |

FOREIGN PATENT DOCUMENTS

| | | |
|---|---|---|
| CA | 105768108 A | 7/2016 |
| CN | 105617358 | 6/2016 |
| CN | 106822560 | 6/2017 |

(Continued)

OTHER PUBLICATIONS

F. Sahena, et al, Fatty Acid Compositions of Fish Oil Extracted from Different Parts of Indian Mackerel (*Rastrelliger kanagutra*) Using Various Techniques of Supercritical CO2 Extraction, 120 Food Chem. 879 (Year: 2010).*

(Continued)

*Primary Examiner* — Sean M Basquill

(74) *Attorney, Agent, or Firm* — Fish IP Law, LLP

(57) ABSTRACT

A nutritional supplement that includes fish oil and selenium has been found to provide a variety of activities beneficial in treating cancer and associated conditions. Such a supplement provides synergistic effects in reducing cancer cell proliferation when used in combination with chemotherapeutic drugs, and can reduce proliferation in drug-resistant cancer cells when used in combination with chemotherapeutic drugs to which the cells are resistant. Effects in reducing angiogenesis, reducing metastasis, reducing the number of circulating cancer cells, and modifying AXL signaling were also found. In addition, use of such a supplement was found to reduce wasting associated with cachexia and reduce circulating cytokines associated with inflammation. Overall effects were found to extend survival in clinical studies.

10 Claims, 112 Drawing Sheets

(56) References Cited

FOREIGN PATENT DOCUMENTS

| DE | 2020013002760 U1 | 7/2014 |
| JP | 06340544 | 6/1996 |
| JP | 20121479 | 1/2012 |
| JP | 2019529578 | 11/2020 |
| KR | 20040073559 | 8/2004 |
| WO | 2011115062 A1 | 9/2011 |
| WO | 2012018597 | 2/2012 |
| WO | 2012122295 | 9/2012 |
| WO | 2018231937 | 12/2018 |
| WO | 2018231943 | 12/2018 |

OTHER PUBLICATIONS

R.S. Pardini, Nutritional Intervention with Omega-3 Fatty Acids Enhances Tumor Response to Anti-Neoplastic Agents, 162 Chemico-Biological Interact. 89 (Year: 2006).*

Marwan Fakih, et al, Selenium Protects Against Toxicity Induced by Anticancer Drugs and Augments Antitumor Activity: A Highly Selective, New, and Novel Approach for the Treatment of Solid Tumors, 5 Clin. Colorec. Cancer 132 (Year: 2005).*

Ronald J. Tallarida, Drug Synergism and Dose-Effect Data Analysis 5-12 (Chapman & Hall/CRC) (Year: 2000).*

Calviello, G, et al. "Antineoplastic effects of N-3 polyunsaturated fatty acids in combination with drugs and radiotherapy: preventive abd therapeutic strategies," Nutrition and Cancer61:3, 287-301. 16 pages.

Ma, et al. "Efficacy of Dietary Antioxidants Combined with a Chemotherapeutic Agent on Human Colon Cancer Progression in a Fluorescent Orthotopic Moue Model," Anticancer Research 29: 2421-2426 (2009). 6 pages.

Extended European Search Report dated May 28, 2021, from related application 18817547.5. 17 pages.

Wang, Hang, et al. "Reduction of splenic immunosuppressive cells and enhancement of anti-tumor immunity by synergy of fish oil and selenium yeast," PLoS ONE 8(1):e52912. 10 pages.

Hwang, Jin-Taek, et al. Selenium Regulates Cyclooxygenase-2 and Extracellular Signal-Regulated Kinase Signaling Pathways by Activating AMPActivated Protein Kinase in Colon Cancer Cells. www.aacrjournals.org. Cancer Res 2006; 66: (20). Oct. 15, 2006. 7 pages.

Douwes, Friedrich. "Integrative Cancer Therapy Concept at St. George Hospital Germany," Klinik St. Georg. 6 pages.

Extended European Search Report dated Feb. 1, 2021, from related application 18817307.4. 6 pages.

Fakih, et al. "Selenium Protects Against Toxicity Induced by Anticancer Drugs and Augments Antitumor Activity: A Highly Selective, New, and Novel Approach for the Treatment of Solid Tumors," Clinical Colorectal Cancer, vol. 5, No. 2, 132-135. 2005. 4 pages.

Norman, et al. "The Role of Dietary Supplements during Cancer Therapy," International Research and Conference on Food, Nutrition, and Cancer. American Society for Nutritional Sciences, 2003. 6 pages.

Fernandes, et al. "Selenium compunds as therapeutic agents in cancer," Biochimica et Biophysica Acta. 2014. 19 pages.

Pardini, Ronals S. Nutiritional intervention with omega-3 fatty acids enhances tumor response to anti-neoplastic agents. ScienceDirect, Chemico-Biological Interactions, 162, 2006, 89-105. 17 pages.

Fahmy, et al. "Protective Effects of omega-3 fatty acids and/or selenium on cisplatin and ionizing radioation induced liver toxicity in rats," Indian Journal of Pharmaceutical Education and Research, vol. 50, Issue 4. 2016. 9 pages.

NIH, National Cancer Institute—What is Cancer? www.cancer.gov/about-cancer/understanding/what-is-cancer.

Knox, Julie, VeryWellHealth—What are Cancer Stem Cells? www.verywellhealth.com/cancer-stem-cells-5096752.

Durrani, et al. "Synergistic effect of selenium compounds with radiation therapy in human A549 lung xenografts," Cancer Research, 2007. 4 pages.

Simone, et al. "Antioxidants and Other Nutrients Do Not Interfere With Chemotherapy or Radiation Therapy and Can Increase Kill and Increase Survival, Part 1," Alternative Therapies, Jan./Feb. 2007, vol. 13, No. 1. 15 pages.

* cited by examiner

Effects of selenium yeast and fish oil in HCC827Gr cells (72 h of treatment)

Control

Selenium yeast 500 ng/ml + Fish oil 75 µM

Iressa 0.1 µM

Selenium yeast 500 ng/ml + Fish oil 75 µM + Iressa 0.1 µM

Iressa does not work well on drug-resistant lung cancer cell, but after adding selenium yeast and fish oil, it shows the synergistic effect on slowing down the cell proliferation.

Even increasing Iressa dosage to 4 μM, there is no significant effect on inhibiting cancer cell proliferation. However, after adding selenium yeast and fish oil, it shows synergistic effect on inhibiting cancer cell proliferation.

Animal

LLC 5*10⁵/mice, s.c.

C57BL/6

| 1 | T | Tumor |
|---|---|---|
| 2 | TT | Tumor + Tarceva |
| 3 | TAC | Tumor + Alimta + Cisplatin |
| 4 | TACT | Tumor + Alimta + Cisplatin + Tarceva |
| 5 | TACN | Tumor + Alimta + Cisplatin + Nutrawell |
| 6 | TACNT | Tumor + Alimta + Cisplatin + Nutrawell + Tarceva |

COMPOSITIONS AND METHODS FOR ENHANCING CANCER CHEMOTHERAPY

This application is a divisional application of U.S. patent application Ser. No. 16/007,539, filed Jun. 13, 2018, which claims the benefit of U.S. Provisional Application No. 62/519,093, filed on Jun. 13, 2017, U.S. Provisional Application No. 62/519,096, filed on Jun. 13, 2017, U.S. Provisional Application No. 62/595,002 filed on Dec. 5, 2017, and U.S. Provisional Application No. 62/670,275 filed on May 11, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is cancer chemotherapy, in particular cancer chemotherapy in combination with a nutritional supplement.

BACKGROUND

The background description includes information that may be useful in understanding the present invention. It is not an admission that any of the information provided herein is prior art or relevant to the presently claimed invention, or that any publication specifically or implicitly referenced is prior art.

Chemotherapy protocols utilized in the treatment of cancer can clearly benefit patients, but can be ineffective or less effective with some cancers, particularly recurring or resistant tumors. In addition chemotherapy is associated with significant side effects, including nausea, weight loss, hair loss, immunosuppression, and skin irritation.

Attempts have also been made to enhance the effects of chemotherapy. Some studies have suggested that consumption of fish oil can improve results from chemotherapy, however other research has suggested that fish oil can interfere (Daenen et al, JAMA Oncol (2015) 1(3):350-358). Formulation of chemotherapeutic agents as nanoparticles has also been attempted (Xu et al, Coll. Surf. B: Biointerfaces (2006) 48(1):50-57). It is unclear, however, if all chemotherapeutic drugs are suitable for such reformulation. Codelivery of chemotherapeutic drugs with siRNA designed to interfere with multi-drug resistance has also been explored. Such siRNAs, however, are sequence specific and may not be suitable for some tumors.

Mitigation of the side effects of chemotherapy is generally directed at providing symptomatic relief. For example, antiemetics can be used to reduce nausea, along with diet modification and eating small, frequent meals that avoid certain foods. Unfortunately such approaches are not always effective. In some instances chemotherapeutic agents are selected to have reduced toxicity in order to reduce side effects, however such agents may also have reduced effectiveness against tumor cells.

Attempts have also been made to improve the sensitivity of cancer cells that are resistant to chemotherapeutic agents. For example, U.S. Pat. No. 7,906,554, to Kelley, describes the use of isoflavones in improving the effectiveness of chemotherapeutic agents. Since the only data provided is directed to a compound that is known to have significant anti-cancer activity (dehydroequol) on its own, however, the effect does not appear to be clearly demonstrated. U.S. Pat. No. 83,463,943, to Kim and Kim, describe the use of glucosamine in sensitizing cancer cells to chemotherapeutic agents. It is not clear, however, if the concentration of glucosamine that was found to be effective (1 mM or higher) can be achieved in vivo. U.S. Pat. No. 9,095,602, to Gleave et al, describes the use of anti-sense DNA to suppress TRPM-2 gene activity in order to enhance chemosensitivity in resistant cancers. Such an approach, however, requires a means of safely and selectively providing the anti-sense DNA to a tumor. In addition, it is not clear that such specific gene suppression will be effective across different cancer cell types and chemotherapeutic mechanisms.

Thus, there is still a need for safe and effective compositions and methods to enhance the effectiveness and/or reduce the side effects of cancer chemotherapy and increase the sensitivity of chemotherapy resistant cancer cells.

SUMMARY OF THE INVENTION

The inventive subject matter provides compositions and methods in which a supplement that includes fish oil and selenium can be used either alone or in combination with chemotherapeutic agents to improve treatment of cancer. A specific formulation for a preferred dietary supplement that includes fish oil and selenium, which has proven to be both effective and palatable, is provided.

Use of a supplement containing fish oil and selenium was found to reduce proliferation in different tumor cell lines, and to do so in a synergistic manner when used in combination with a variety of chemotherapeutic agents. Increases in biochemical markers associated with apoptosis and oxidative stress, along with shifts in cell cycle phase distribution are also found in cancer cells so treated. Similarly, reductions in tumor size are found in animal models of different tumor types on treatment with such a supplement, either alone or in combination with chemotherapeutic agents. In addition to reducing tumor size, use of a supplement containing fish oil and selenium (either alone or in combination with a chemotherapeutic drug) was found to reduce the number and size of tumor-associated blood vessels, indicating an anti-angiogenic effect. Certain chemotherapeutic drugs were also found to have previously undocumented anti-angiogenic effects when used alone. In addition to reductions in tumor size, use of such supplements (either alone or in combination with chemotherapeutic agents) was found to reduce indicators of tumor progression and the incidence of metastasis. Similarly, in a clinical setting use of a supplement containing fish oil and selenium was found to reduce the number of circulating tumor cells.

Surprisingly, stem cell characteristics of cancer stem cells and sphere cells were reduced by use of supplements containing fish oil and selenium. AXL signaling was also modified. Such supplements were also found to render drug-resistant tumor cells sensitive to chemotherapeutic agents to which they were resistant. Treatment with a supplement containing fish oil and selenium was found to modify expression of biochemical markers related to immune response to cancer cells in both cancer cells and cells of the immune system, indicating that such a supplement can complement or potentiate immunotherapy.

Supplements containing fish oil and selenium were also found to be effective in relieving wasting associated with cachexia, and to do so beyond their caloric contribution. Mass of fat, muscle, and various organ tissues is improved or maintained, despite simultaneous chemotherapy. Biochemical markers associated with tissues affected by cachexia are also increased on use of such a supplement.

Circulating concentrations of a variety of cytokines, many of which are associated with inflammation, are also normalized on use of such a supplement.

Overall, use of a supplement containing fish oil and selenium, particularly in cotherapy with chemotherapeutic drugs, provides anti-tumor effects and reduces cachexis and inflammation associated with the disease. Such a combination of effects was found to improve survival rate in clinical studies of cancer patients.

Various objects, features, aspects and advantages of the inventive subject matter will become more apparent from the following detailed description of preferred embodiments.

DETAILED DESCRIPTION

Figure 1:
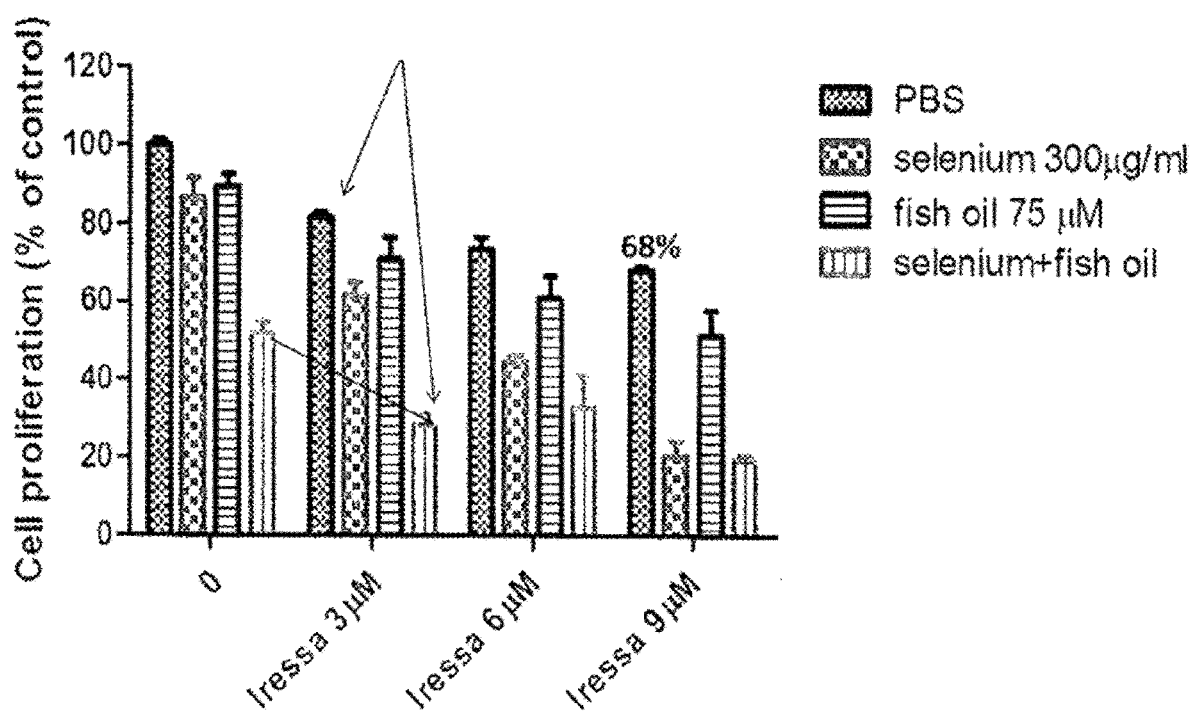
FIG. 1: Histogram of the effect of treatment with Iressa (3 µM to 9 µM) in combination with PBS or various supplements on proliferation of A549 lung tumor cells.

The following description includes information that may be useful in understanding the present invention. It is not an admission that any of the information provided herein is prior art or relevant to the presently claimed invention, or that any publication specifically or implicitly referenced is prior art.

The inventive subject matter provides compositions and methods in which a nutritional supplement (such as a supplement that includes fish oil, selenium in the form of selenium yeast, chromium, and certain plant-derived materials (NutraWell) and/or a supplement that includes a selenium and fish oil) is used in combination with chemotherapy. Combination therapy with chemotherapeutic agents and the supplement surprisingly provides a significant synergistic effect in reduction of tumor size and/or reducing cell proliferation. In addition, side effects of radiotherapy are mitigated and expression of genes related to apoptosis is modulated in tumor cells. Surprisingly, supplements of the inventive concept were also found to increase the sensitivity of resistant cancer cells to chemotherapeutic agents.

One should appreciate that the disclosed techniques provide many advantageous technical effects including enhancing the effectiveness of current chemotherapy protocols used in the treatment of cancer while reducing the side effects associated with these approaches, and in the treatment of cancer that are resistant to chemotherapy.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

While the some findings described below are directed to the use of fish oil and a selenium source, the Applicant notes that the nutritional supplement formulation provided in Table 1 (i.e. NutraWell) incorporates fish oil and selenium. The selenium is preferably provided as selenium yeast or components thereof (such as peptides and/or amino acids prepared from selenium yeast). As such effects found in fish oil and selenium yeast studies can be extended to the use of this nutritional supplement. NutraWell has been found to have a high level of acceptance and to have unanticipated beneficial anti-tumor activity in combination with conventional therapies. As shown below, such a nutritional supplement also shows striking beneficial effects when used in combination with one or more chemotherapeutic agents.

TABLE 1

| Component | Minimum | Maximum | Unit |
|---|---|---|---|
| Maltodextrin | 10000 | 50000 | mg |
| Whey Protein Isolate | 5000 | 60000 | mg |
| Whey Protein Concentrate | 1000 | 50000 | mg |
| Fructooligosaccharides/Inulin | 40 | 15000 | mg |

TABLE 1-continued

| Component | Minimum | Maximum | Unit |
|---|---|---|---|
| Granulated Honey | 1000 | 9000 | mg |
| Oat Fiber | 500 | 15000 | mg |
| Natural French Vanilla Flavor | 500 | 20000 | mg |
| Soy Protein | 500 | 50000 | mg |
| Brownulated Powdered Brown Sugar | 500 | 10000 | mg |
| Natural Vanilla Masking Flavor | 500 | 5000 | mg |
| Lecithin | 200 | 10000 | mg |
| Milk, Non-fat | 50 | 5000 | mg |
| Rice Protein Powder | 50 | 5000 | mg |
| Calcium Caseinate | 50 | 2000 | mg |
| Oils | | | |
| Flax Seed Oil | 100 | 7000 | mg |
| Canola Oil | 100 | 7000 | mg |
| Borage Oil | 100 | 7000 | mg |
| Olive Oil | 100 | 7000 | mg |
| Fish Oil | 150 | 10,000 | mg |
| Pure Lemon Oil | 100 | 1000 | mg |
| Pure Orange Oil | 50 | 1000 | mg |
| Mixed Tocopherols | 0.5 | 200 | mg |
| Vitamins/Minerals | | | |
| Potassium Phosphate | 200 | 1500 | mg |
| Calcium Carbonate | 100 | 5000 | mg |
| Choline Bitartrate | 150 | 2500 | mg |
| Sodium Chloride | 100 | 2000 | mg |
| Calcium Phosphate Tribasic | 100 | 2000 | mg |
| Ascorbic Acid | 50 | 3000 | mg |
| Potassium Chloride | 50 | 2000 | mg |
| Magnesium Oxide | 50 | 500 | mg |
| Selenium Yeast | 30 | 4000 | mcg |
| Chromium Yeast | 30 | 3000 | mcg |
| Molybdenum Yeast | 30 | 2000 | mcg |
| Inositol | 10 | 5000 | mg |
| Zinc Sulfate Monohydrate | 5 | 200 | mg |
| Dry Vitamin E Acetate | 5 | 2000 | IU |
| Niacinamide | 5 | 500 | mg |
| Ferric Orthophosphate | 3 | 100 | mg |
| Calcium Pantothenate | 3 | 200 | mg |
| Manganese Sulfate Monohydrate | 3 | 100 | mg |
| Beta Carotene | 1 | 100 | mg |
| Copper Gluconate | 1 | 15 | mg |
| Vitamin D3 | 25 | 5000 | IU |
| Vitamin K2 | 2 | 1000 | mcg |
| Pyridoxine HCl | 0.5 | 200 | mg |
| Potassium Iodide | 0.5 | 1500 | mg |
| Riboflavin | 0.5 | 1000 | mg |
| Thiamine Hydrochloride | 0.5 | 2500 | mg |
| Dry Vitamin K1 | 1 | 500 | mcg |
| Vitamin A Acetate | 500 | 100000 | IU |
| Folic Acid | 100 | 10000 | mcg |
| d-Biotin | 10 | 10000 | mcg |
| Vitamin B12 | 1 | 3000 | mcg |
| Amino Acids | | | |
| L-Carnitine | 300 | 30000 | mg |
| L-Glutamine | 500 | 60000 | mg |
| L-Arginine Base | 500 | 30000 | mg |
| Taurine | 50 | 2000 | mg |
| L-Lysine | 50 | 2000 | mg |
| Alpha Lipoic Acid | 10 | 1000 | mg |
| Resveratrol | 15 | 1500 | mg |
| Co-Enzyme Q10 | 10 | 5000 | mg |
| Glycine | 5 | 1000 | mg |
| Proline | 5 | 1000 | mg |
| Bacterial Cultures | | | |
| *Lact. Acidophilus* (app. 10 billion total) | 2 | 500 | mg |
| *Bifido Bifidium* (app. 10 billion total) | 2 | 500 | mg |
| *Lac. Bulgaricus* (app. 10 billion total) | 2 | 500 | mg |
| *Bifido Longum* (app. 10 billion total) | 2 | 500 | mg |
| *Strep. Thermophilus* (app. 10 billion total) | 2 | 500 | mg |
| Enzymes | | | |
| Papain | 5 | 100 | mg |
| Pepsin | 5 | 100 | mg |
| Lipase | 5 | 100 | mg |
| Bromelain | 5 | 100 | mg |
| Pancreatin 4X | 0.5 | 100 | mg |
| Lactase | 1 | 100 | mg |
| Betaine HCl | 3 | 100 | mg |
| Plant Products | | | |
| Pineapple Juice Powder | 2 | 500 | mg |
| Papaya Fruit Powder | 2 | 500 | mg |
| Quercetin | 30 | 3000 | mg |
| EGCG | 25 | 600 | mg |
| OPC | 15 | 500 | mg |
| Anthocyanins | 15 | 5000 | mg |
| Ellagic Acid | 10 | 300 | mg |
| Astaxanthin | 2 | 90 | mg |
| Fucoidan | 20 | 1500 | mg |
| Mushroom Preparation | | | |
| Cordyceps | 5 | 6000 | mg |
| Ganoderma Lucidum | 15 | 10000 | mg |
| Shiitake | 40 | 15000 | mg |
| Maitake | 30 | 15000 | mg |
| Turkey Tail | 30 | 15000 | mg |

The composition shown in Table 1 includes components in addition to selenium and fish oil that have various physiological and biochemical effects, including anti-inflammatory activity, lowering of blood glucose levels, lowering of cholesterol, and anti-tumor activity. In preferred embodiments the nutritional supplement includes at least three components as represented in Table 1. Such additional components provide supplementation of necessary vitamins, minerals, and amino acids at elevated levels. Other components (e.g. enzymes, lecithin) serve to aid in digestion and absorption of components of the composition when consumed. The combination of these complementary activities provides a synergistic effect that exceeds the simple additive effect of individual components. It should be appreciated that the composition shown in Table 1 also includes certain flavorants (e.g. brown sugar, honey, vanilla flavor and masking agent) that serve to improve palatability and acceptance. Certain components (e.g. honey, brown sugar, milk, rice protein, casein) can provide both flavor and caloric energy. The Inventor has found that the combination of flavorants described above is effective in providing compliance with consumption of the nutritional supplement in effective amounts. In some embodiments, such flavorants can be excluded without negatively impacting the effectiveness of the nutritional supplement.

Components shown in Table 1 can be provided as a single formulation (for example, as a pill, tablet, capsule, powder, liquid, suspension, etc.) or can be segregated into different formulations (for example, as pills, tablets, capsules, powders, liquids, suspensions, or combinations thereof). The amounts shown in Table 1 are exemplary, and represent typical daily dosages provided to an adult of normal stature and otherwise normal health. These amounts can be adjusted to account for differences in body mass, gender, medical condition, etc. For example, a relatively small patient weighing 40 kilos or less may receive benefit from dosages provided at or below the low end of the ranges provided, whereas a relatively large patient weighing 100 kilograms or more may require dosages provided at the high end of the ranges noted (or more). In some embodiments such a daily dose can be distributed as multiple doses throughout the day. In some of such embodiments the composition of each of such distributed doses can be identical. In other embodiments the composition of such distributed doses can be different, provided the summation of such doses provides the required supplementation.

Tumor Cell Proliferation

Figure 2:
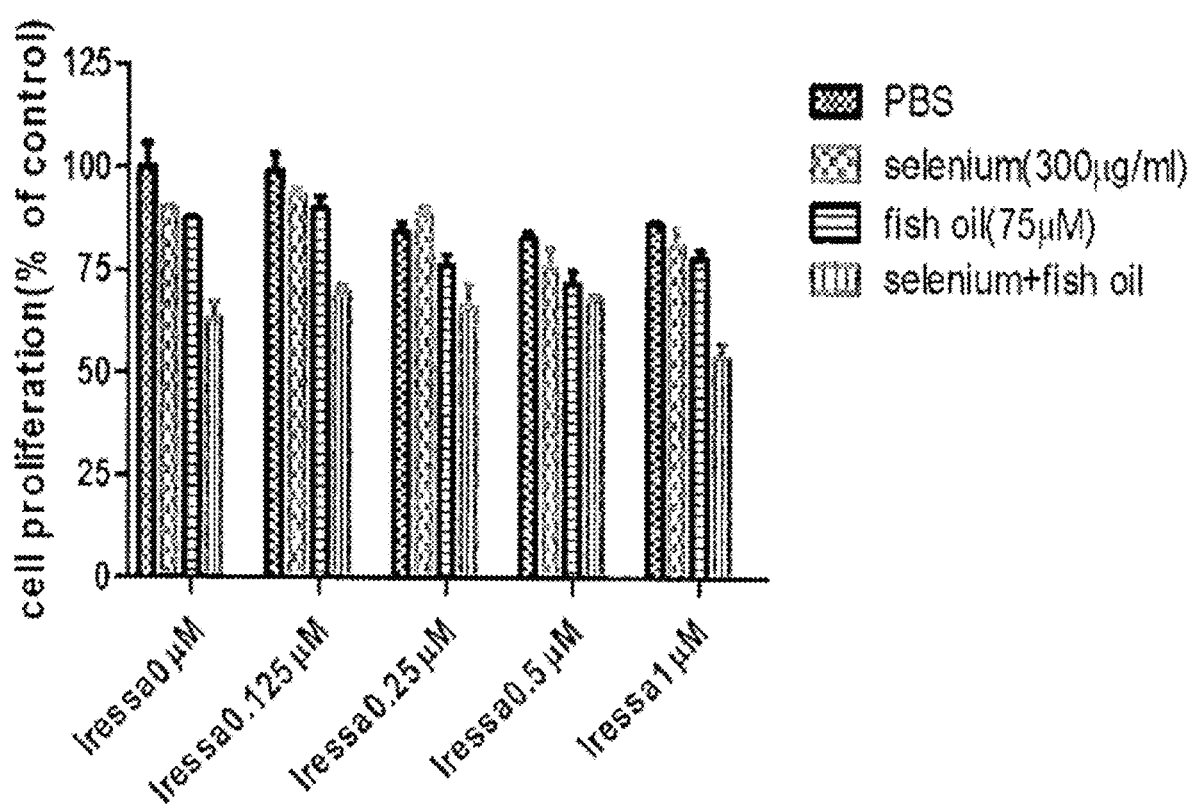
FIG. 2: Histogram of the effect of treatment with Iressa (0.125 µM to 1 µM) in combination with PBS or various supplements on proliferation of A549 lung tumor cells.
Figure 3:
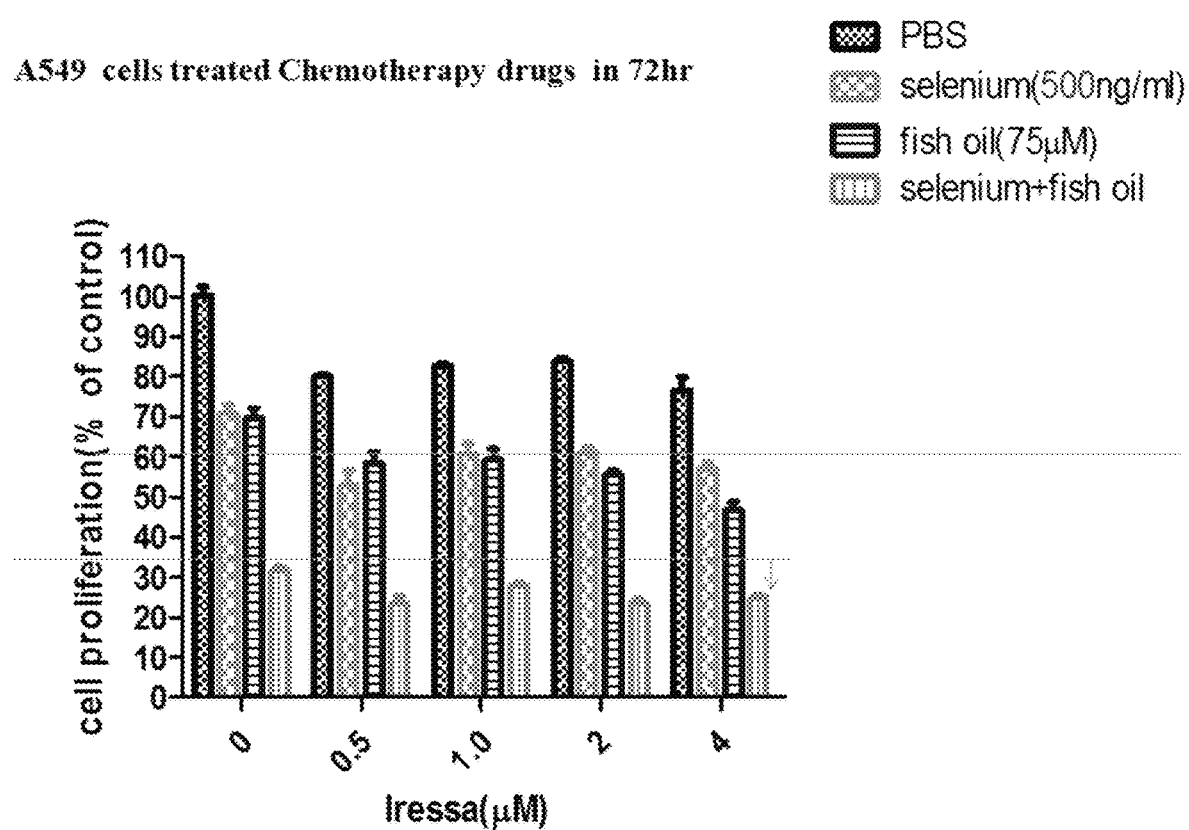
FIG. 3: Histogram of the effect of treatment with Iressa (0.5 µM to 4 µM) in combination with PBS or various supplements on proliferation of A549 lung tumor cells.
Figure 4:
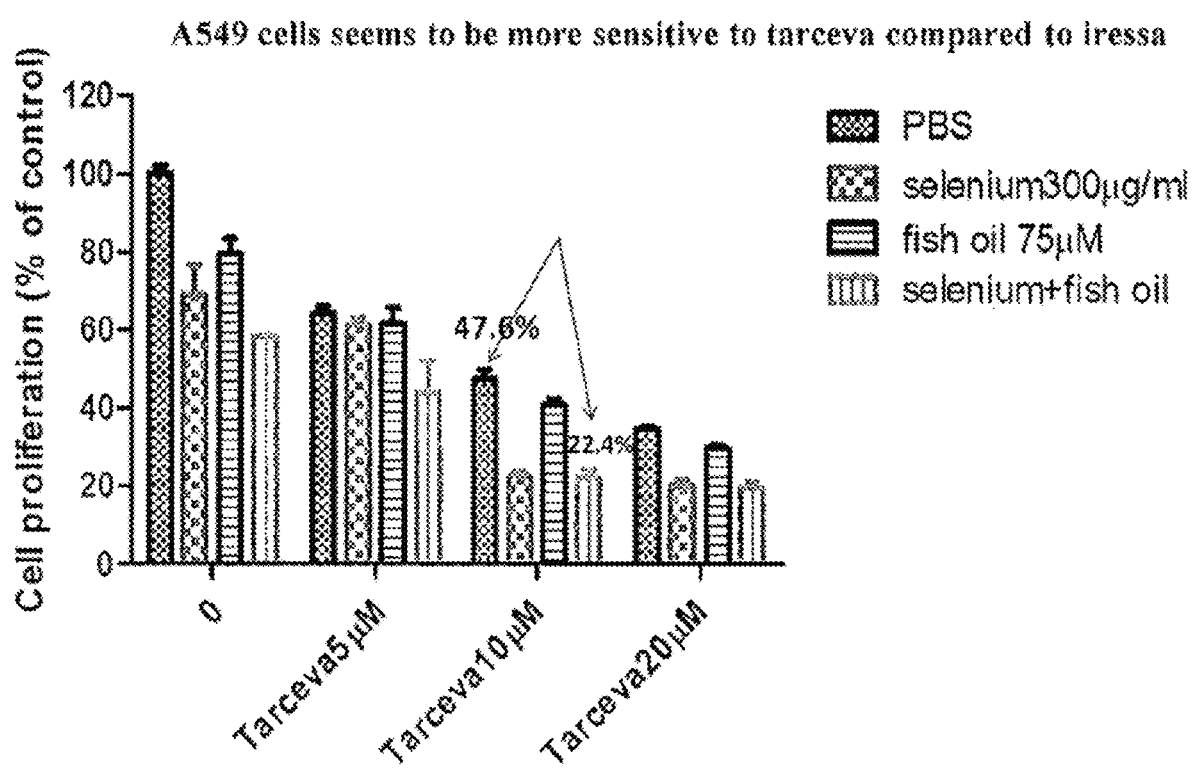
FIG. 4: Histogram of the effect of treatment with Tarceva (5 µM to 20 µM) in combination with PBS or various supplements on proliferation of A549 lung tumor cells.
Figure 5:
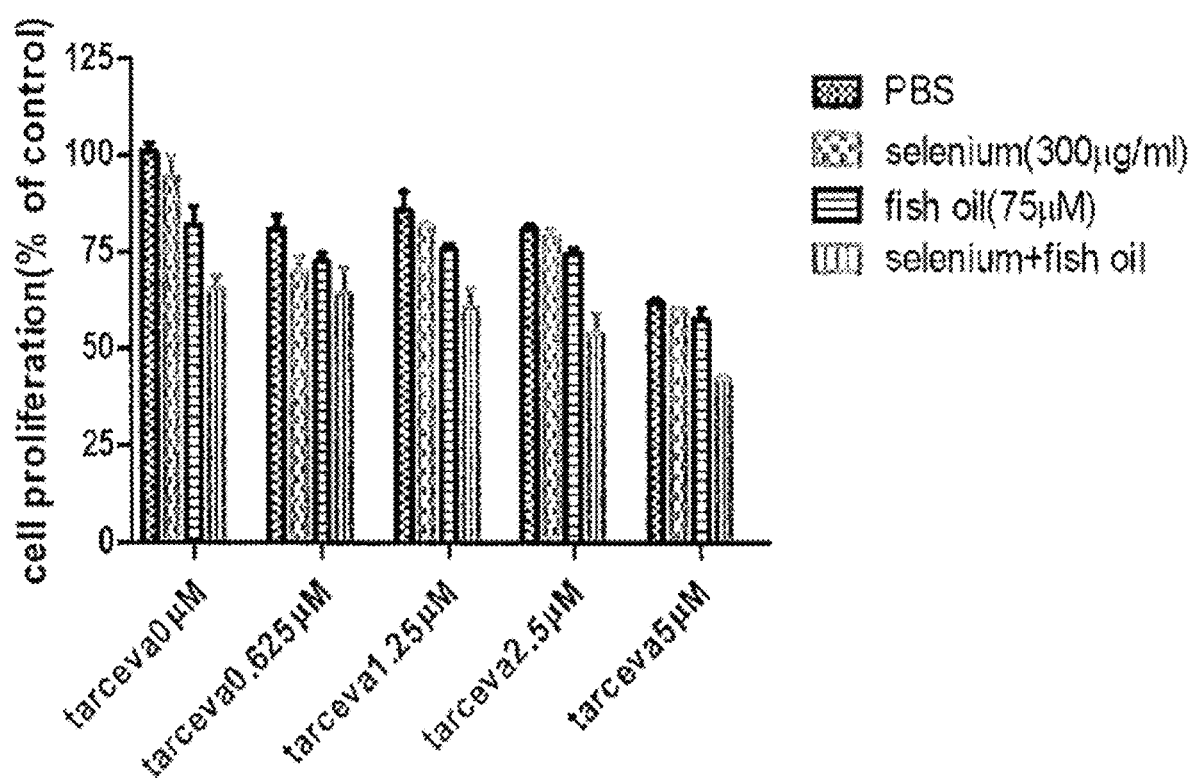
FIG. 5: Histogram of the effect of treatment with Tarceva (0.625 µM to 5 µM) in combination with PBS or various supplements on proliferation of A549 lung tumor cells.
Figure 6:
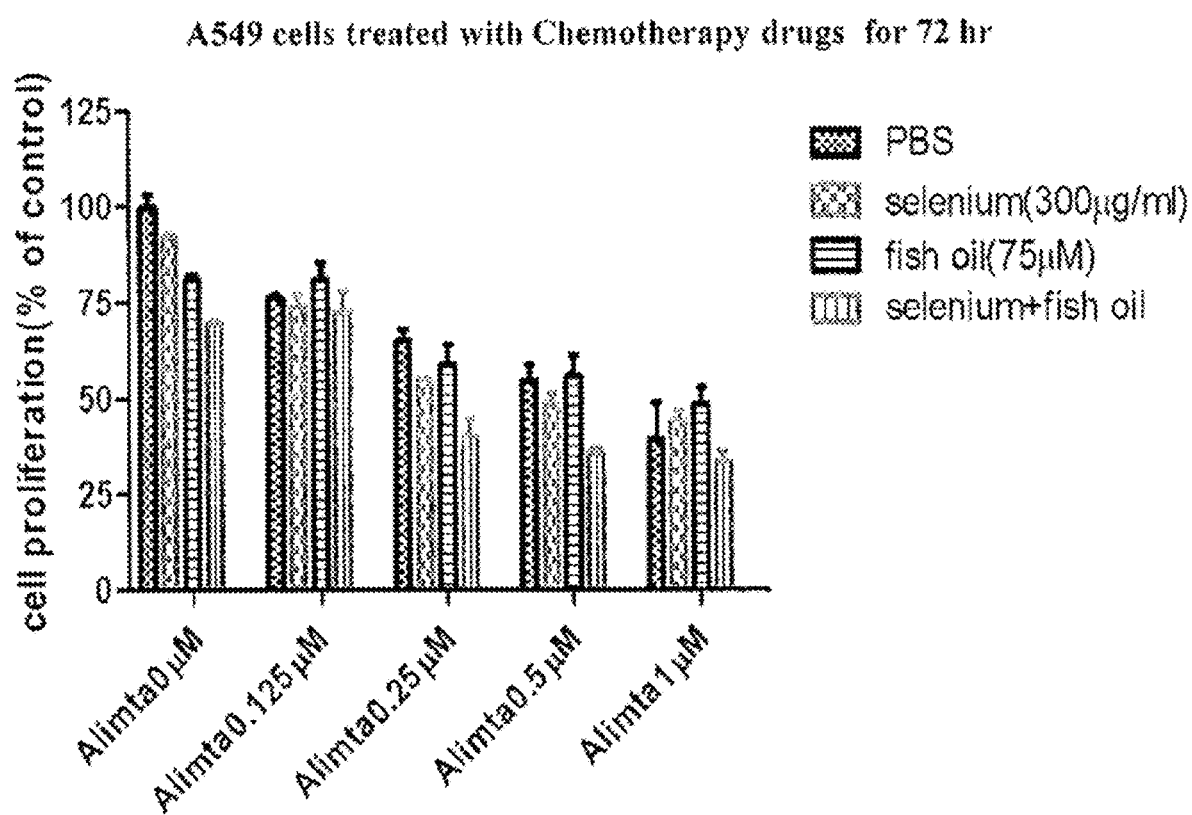
FIG. 6: Histogram of the effect of treatment with Alimta (0.125 µM to 1 µM) in combination with PBS or various supplements on proliferation of A549 lung tumor cells.
Figure 7:
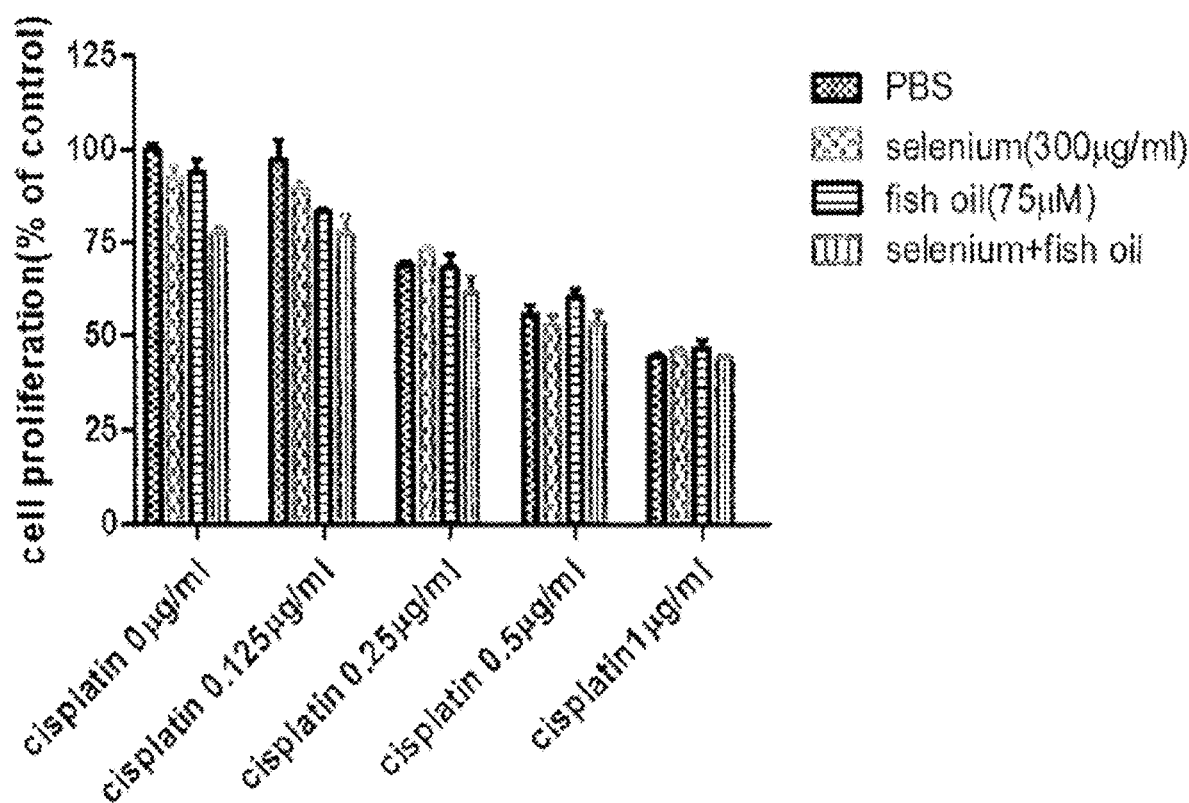
FIG. 7: Histogram of the effect of treatment with Cisplatin (0.125 µg/mL to 1 µg/mL) in combination with PBS or various supplements on proliferation of A549 lung tumor cells.

Surprisingly, the Inventor has found that treatment of various cancer cells with a combination of fish oil and selenium yeast has a direct impact on cell proliferation, particularly when used in combination with cancer chemotherapeutic agents. Examples of the effects of co-treatment of tumor cells with chemotherapeutic agents and with a nutritional supplement that includes fish oil and a selenium peptide can be seen in FIG. 1, FIG. 2, FIG. 3, FIG. 4, FIG. 5, FIG. 6, FIG. 7, FIG. 8, FIG. 9 and FIG. 10. These figures show the effect of treatment of various cancer cell lines with chemotherapeutic agents and a fish oil supplement, a selenium peptide supplement, and a supplement made by combining fish oil and the selenium peptide. FIG. 1, FIG. 2, and FIG. 3 show the effects of treatment with Iressa in combination with PBS or various supplements on proliferation of A549 lung tumor cells. As shown, the use of a supplement containing both fish oil and selenium reduces A549 cell proliferation, and the combination also provides an unexpected synergistic effect in reducing A549 cell proliferation when used in combination with Iressa. Similar effects are seen in FIG. 4 and FIG. 5 when such a nutritional supplement is used in combination with Tarceva to treat A549 cancer cells. The effects of a nutritional supplement containing both fish oil and selenium in combination with on the proliferation of A549 cancer cells in combination with Alimta is shown in FIG. 6, while the effects of such a nutritional supplement in combination with Cisplatin on proliferation of A549 cancer cells is shown in FIG. 7. Synergistic effects for the combination of a nutritional supplement containing fish oil and selenium and the chemotherapeutic agent are notable in many instances, particularly at lower drug concentrations.

Figure 8:
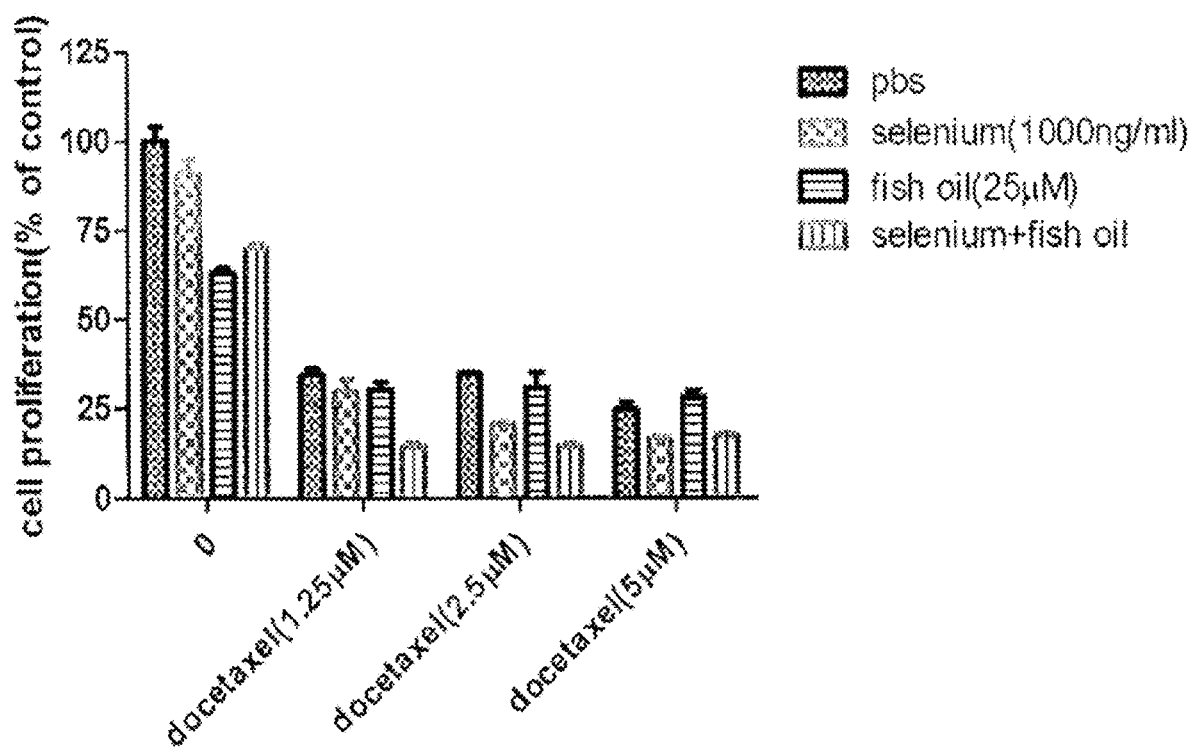
FIG. 8: Histogram of the effect of treatment with Docetaxel (1.25 µM to 5 µM) in combination with PBS or various supplements on proliferation of MDA-MB-231 breast cancer cells.
Figure 9:
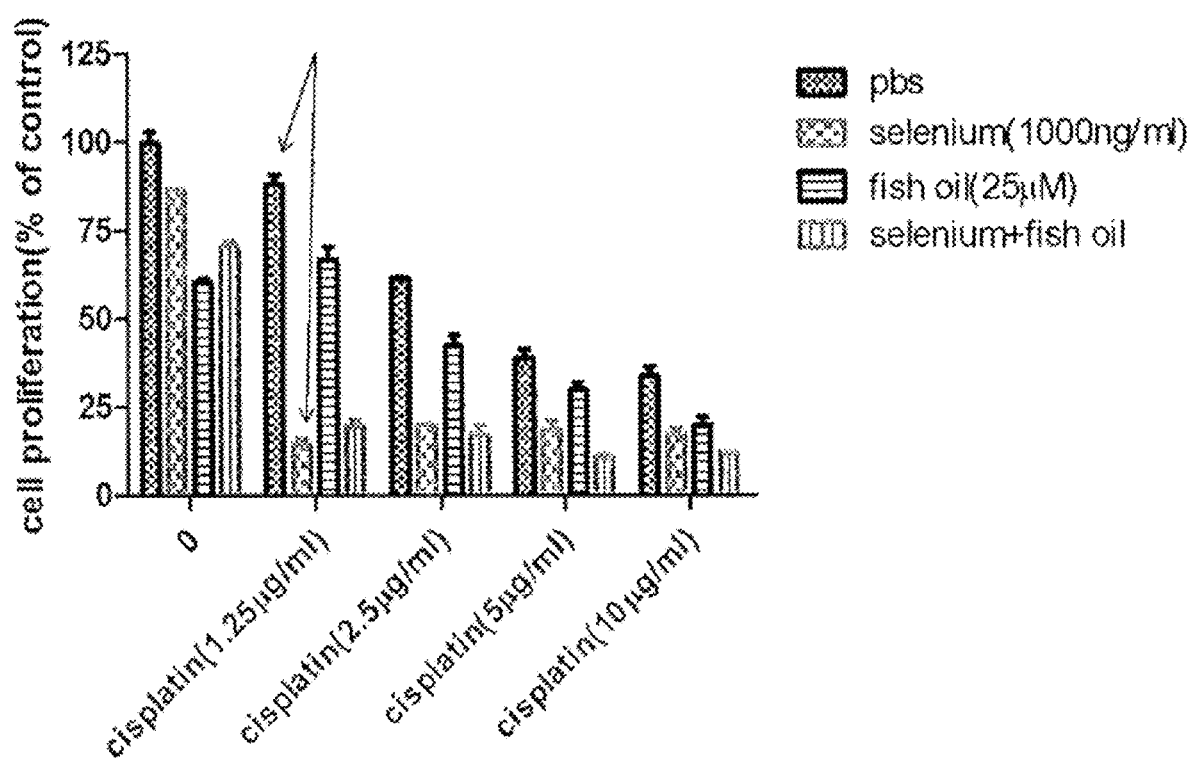
FIG. 9: Histogram of the effect of treatment with Cisplatin (1.25 µg/mL to 10 µg/mL) in combination with PBS or various supplements on proliferation of MDA-MB-231 breast cancer cells.
Figure 10:
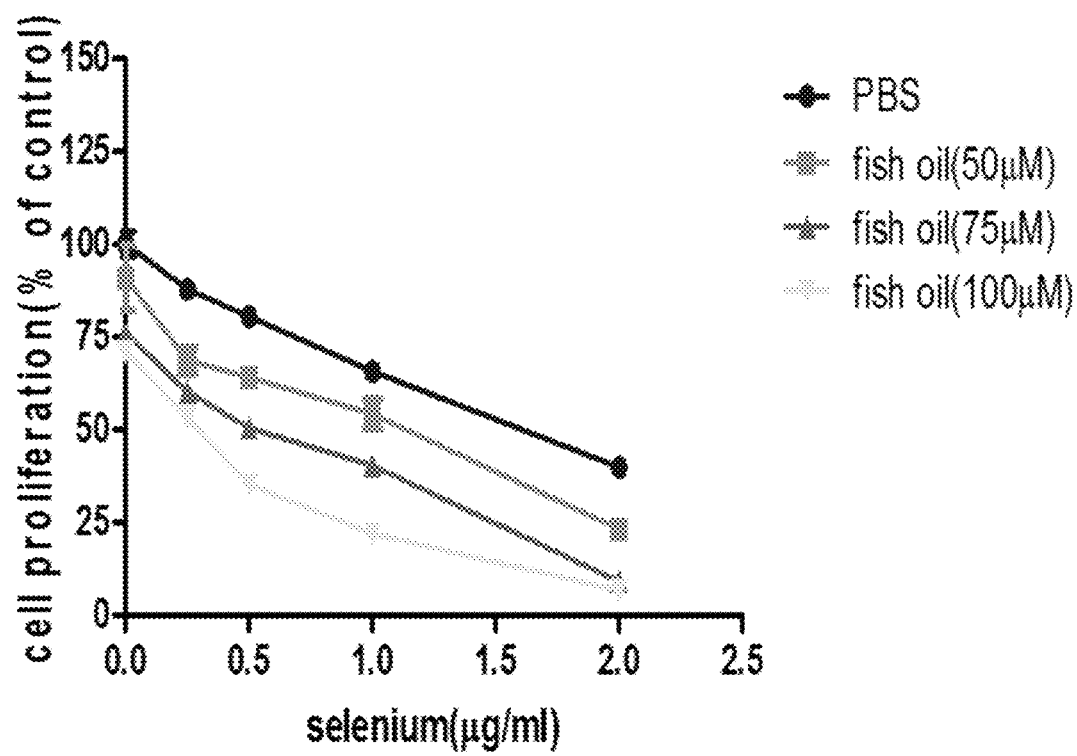
FIG. 10: Effect of a supplement containing selenium, a supplement containing fish oil, and a nutritional supplement containing both fish oil and selenium on proliferation of A549 cells in culture.

Inventors have surprisingly found that co-treatment with chemotherapeutic agents and a fish oil/selenium peptide supplement also provides similar effects in an unrelated triple-negative breast cancer cell line (MDA-MB-231). Typical results of co-treatment of these cells with Docetaxel and fish oil/selenium supplement for 72 hours on cell proliferation are shown in FIG. 8. While this chemotherapeutic agent and the supplement containing fish oil and selenium both provided a reduction in proliferation, a surprising synergistic effect is noted when they are used in combination. Similar effects are seen when MDA-MB-231 cells are treated with nutritional supplements containing fish oil, selenium, fish oil and selenium in combination, and Cisplatin. Surprisingly, synergistic effects in reducing proliferation are found for both a selenium containing supplement and a selenium/fish oil supplement when used in combination with Cisplatin.

Figure 11:
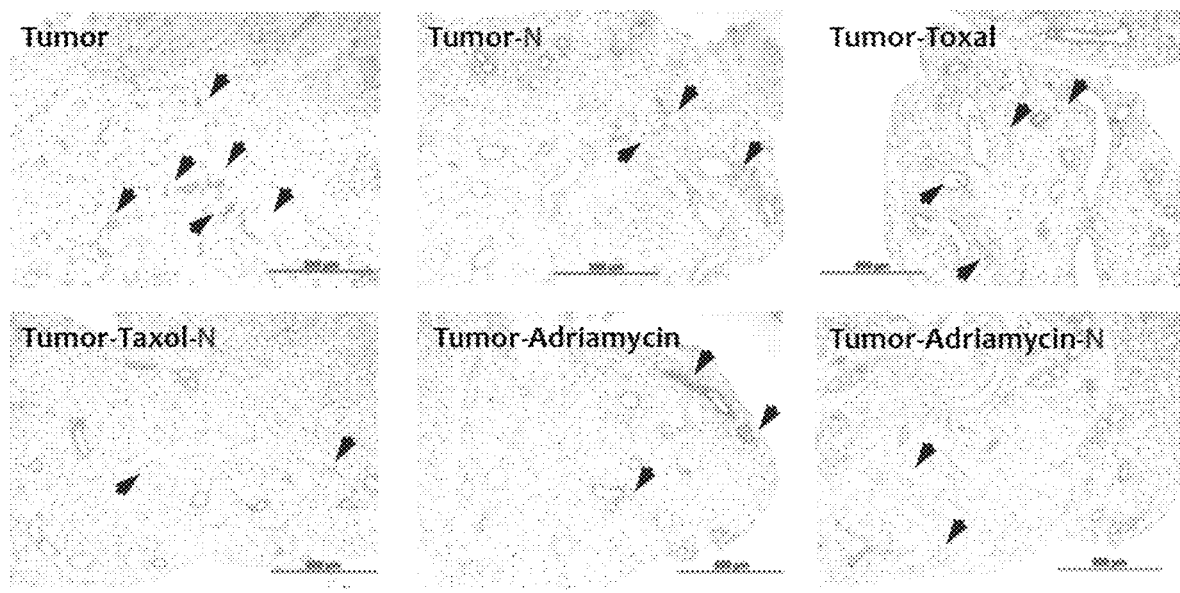
FIG. 11: Graph showing the effect of a nutritional supplement containing fish oil and selenium and/or chemotherapeutic agents on expression of Ki-67.

The effects of a nutritional supplement that includes fish oil and selenium in combination with chemotherapeutic drugs were also identified in in vivo studies, where the Ki-61 proliferative index marker was identified in mammary gland tumors of murine models by immunocytochemistry. Typical results of such studies are shown in FIG. 11, where Ki-61 cells are indicated by arrows. As shown, treatment with the fish oil/selenium supplement ("N") reduces the number of positive cells (indicating a reduction in proliferative index) as does treatment with chemotherapeutic agents (Taxol, Adriamycin. Treatment with a combination of both the nutritional supplement and a chemotherapeutic agent provided an even greater reduction in proliferative index.

Overall, the Inventor has found that a nutritional supplement that includes fish oil and selenium (for example, in the form of selenium yeast or yeast products) can reduce proliferation in a variety of tumor cell types, and can provide a synergistic effect when used in combination with a variety of different chemotherapeutic agents. The effect is seen both in cell culture and in in vivo animal models of human disease.

Tumor Size

Figure 12:
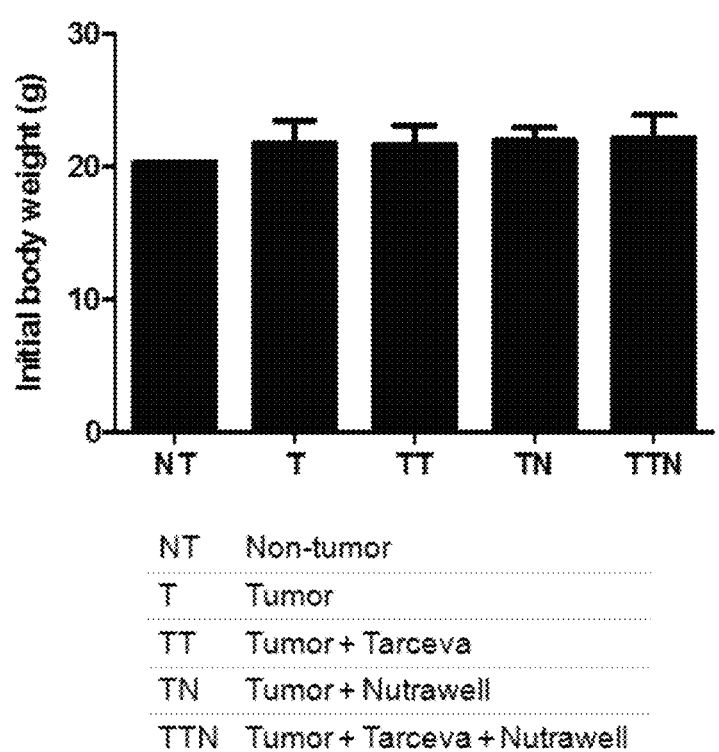
FIG. 12: Initial body weight of mice utilized in Tarceva and nutritional supplement containing fish oil and selenium studies.
Figure 13:
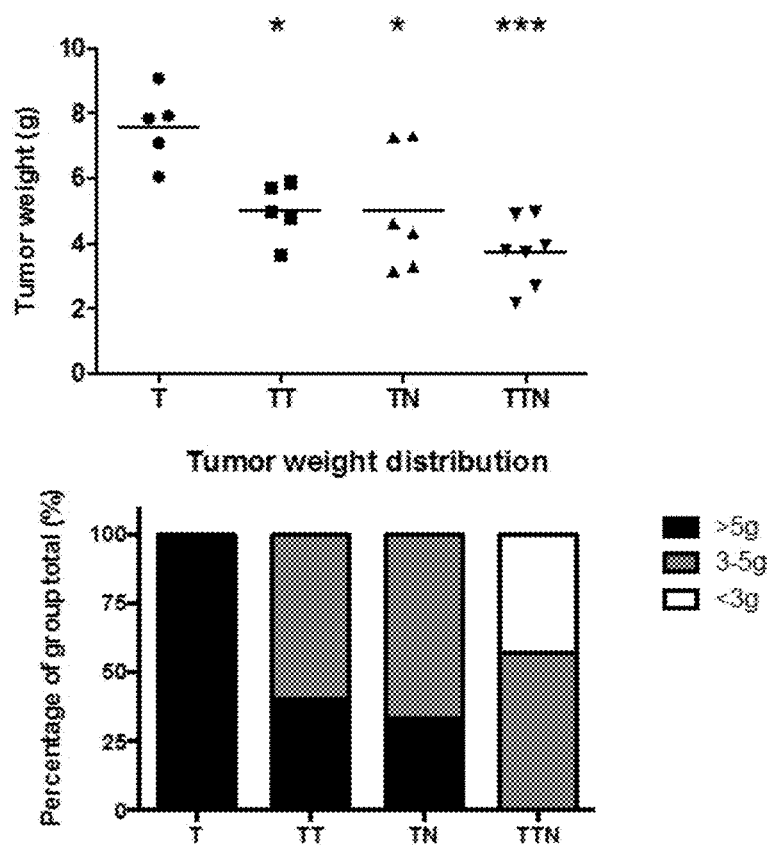
FIG. 13: Histogram showing weight of tumors in mice treated with Tarceva, a nutritional supplement containing fish oil and selenium, or a combination of these.

The Inventor has also found that a nutritional supplement that includes fish oil and selenium reduces tumor size in in vivo animal models of human disease, and surprisingly can do so in a synergistic manner when used in combination with chemotherapeutic drugs. 8FIG. 8A provides an example of a typical testing protocol for such a nutritional supplement ("Nutrawell") and the chemotherapeutic drug Tarceva. Initial body weights of mice used in such studies, which can be used to calculate tumor weight, are shown in FIG. 12. Results of studies of tumor weight (upper panel) and tumor weight distribution (lower panel) are shown in FIG. 13. As shown, 28 days after tumor implantation mice were sacrificed and the tumor characterized. Untreated mice all developed large (>5 g) tumors. Mice treated with either Tarceva or NutraWell still showed a significant number of such large tumors. Mice treated with a combination of Tarceva and a fish oil/selenium nutritional supplement, however, did not show any large tumors and had a significant proportion of small (<3 g) tumors.

Figure 14:
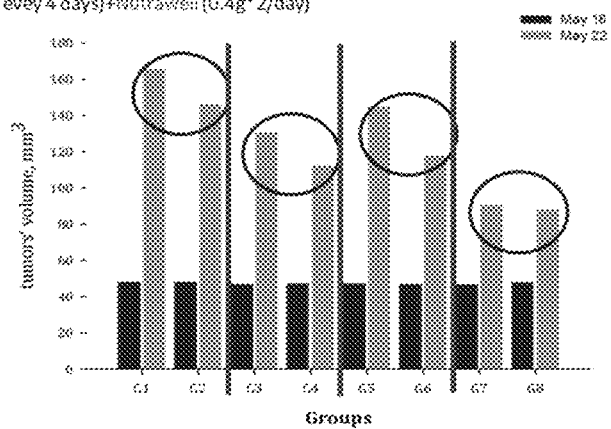
FIG. 14: Histogram of the effect of a nutritional supplement containing fish oil and selenium and/or chemotherapeutic agents in mice implanted with human breast cancer cells

Similar results were found in mice implanted with cells derived from a human breast cancer and treated with a fish oil/selenium nutritional supplement in combination with chemotherapeutic drugs commonly used to treat breast cancer (e.g. Taxol, Adriamycin, Avastin, etc.). FIG. 14 shows an exemplary treatment protocol (upper panel) and the results of tumor volume studies (lower panel) performed on control (untreated) mice, mice treated with a fish oil/selenium nutritional supplement, and mice treated with various chemotherapeutic agents with and without co-treatment with a fish oil/selenium nutritional supplement. Tumor volume was recorded at two different time periods, and shows the effect on growth. Untreated (control) mice show an approximately 120 mm$^3$ increase in tumor volume over 4 days. As shown, the chemotherapeutic drugs Taxol, Adiamycin, and/or Avastin used in combination with a fish oil/selenium nutritional supplement show a significantly decreased rate of tumor growth relative to the use of these chemotherapeutic agents alone. It should also be appreciated that the fish oil/selenium nutritional supplement alone provided a reduction in tumor growth.

Figure 15:
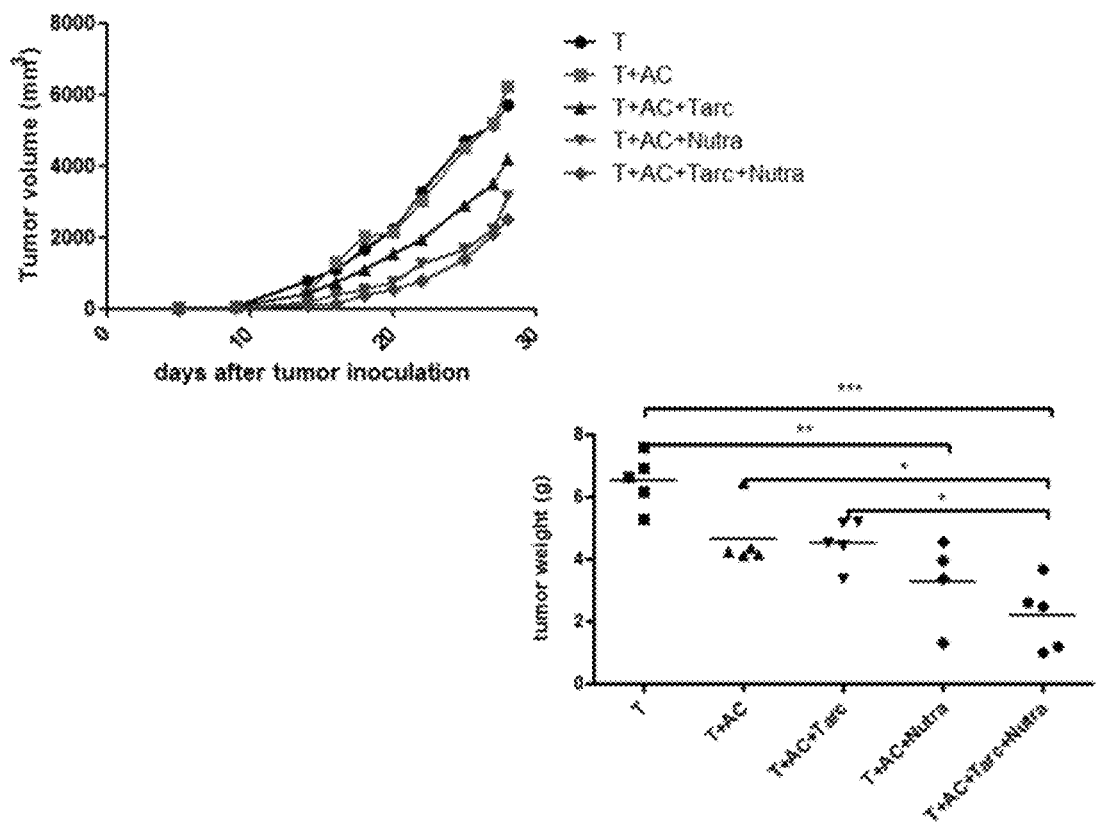
FIG. 15: Graphical depiction of the effects by cotherapy with a nutritional supplement containing fish oil and selenium and chemotherapy on tumor volume and mass.

Surprisingly, cotherapy with a fish oil/selenium nutritional supplement was found to potentiate the effects of chemotherapeutic reagents in a synergistic manner. As shown in FIG. 15, tumor volume (upper panel) in implanted mice is not notably impacted by treatment with Alimta and Cisplatin, indicating resistance to this combined chemotherapy. Addition of Tarceva to this chemotherapy regime provides only marginal improvement in terms of reducing tumor volume. Large reductions are, however, observed when Alimta and Cisplatin are combined with a fish oil/ selenium nutritional, with greater reductions seen when NutraWell is used in combination with all three chemotherapeutic drugs. Similar results are seen for tumor weight (lower panel).

Figure 16:
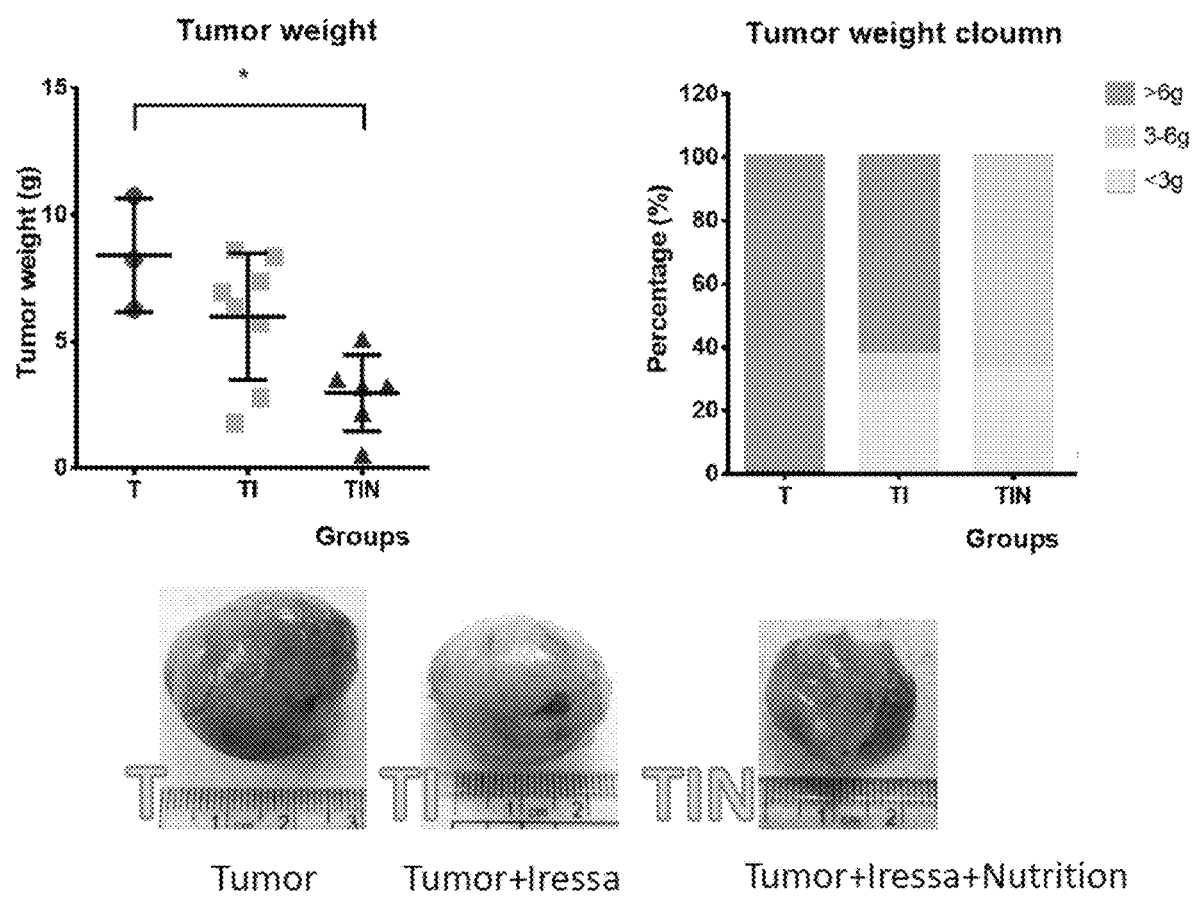
FIG. 16: Histograms and photographs of the effect of treatment with Iressa and Iressa in combination with a nutritional supplement containing fish oil and selenium on weight and weight distribution of tumors produced by injection of lung cancer cells.

The effects of cotreatment with a nutritional supplement containing fish oil and selenium and the chemotherapeutic drug Iressa on tumor weight in mice implanted with lung cancer cells can be seen in FIG. 16. As shown, treatment with Iressa alone provides only a marginal reduction in tumor weight (top left panel), while cotreatment with Iressa and a nutritional supplement containing fish oil and selenium reduced tumor weight by more 50% relative to untreated control mice. Weight distribution (top right panel)

also shows a modest reduction in tumor weight on treatment with the chemotherapeutic agent (with most of the mice having >6 gram tumors), while cotreatment with a nutritional supplement containing fish oil and selenium resulted in all tumors having a weight of less than 6 grams and many having a weight of less than 3 grams. Photographs of typical examples of tumors obtained from mice in the control and treated groups is shown in the lower panel of FIG. 16.

Further in vivo studies were performed using the protocol shown in Table 2.

TABLE 2

Figure 17:
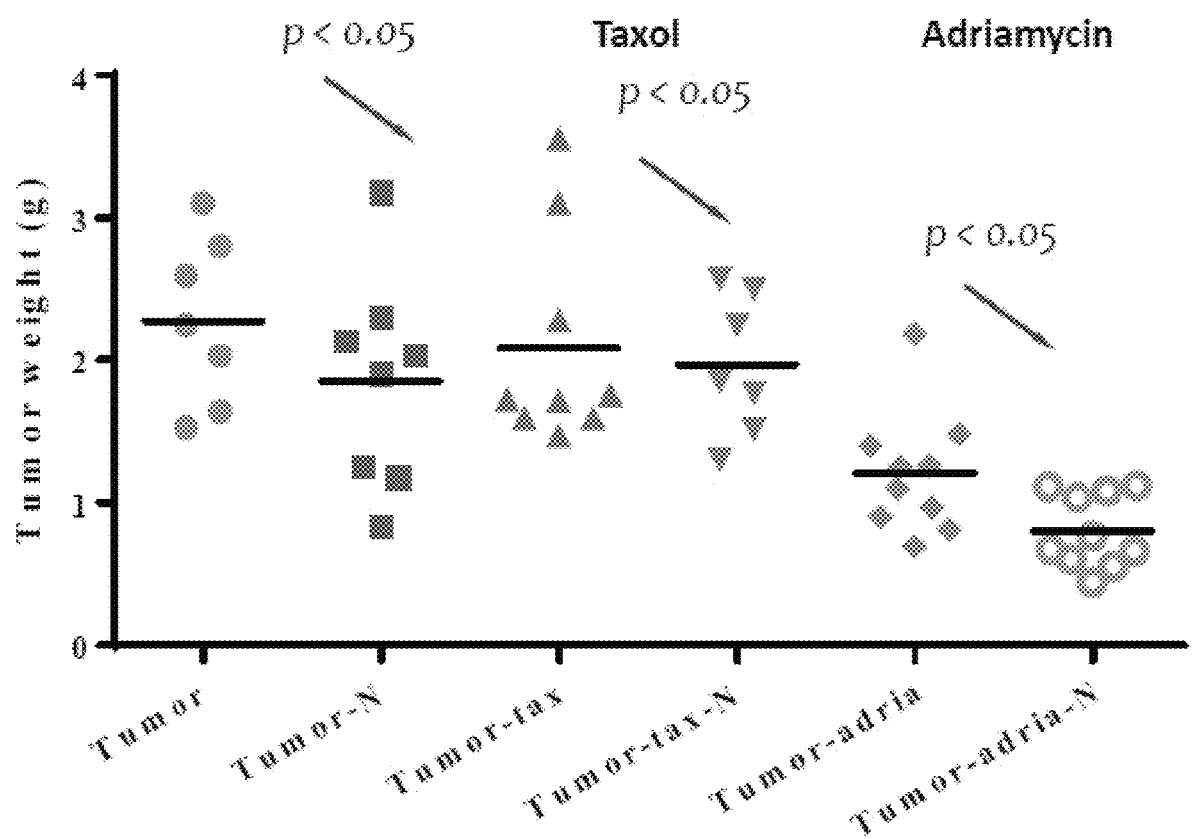
FIG. 17: Graph of the effect on tumor weight of addition of a nutritional supplement containing fish oil and selenium to Taxol and Adriamycin treatment regimes in an in vivo model of breast cancer.
Figure 18:
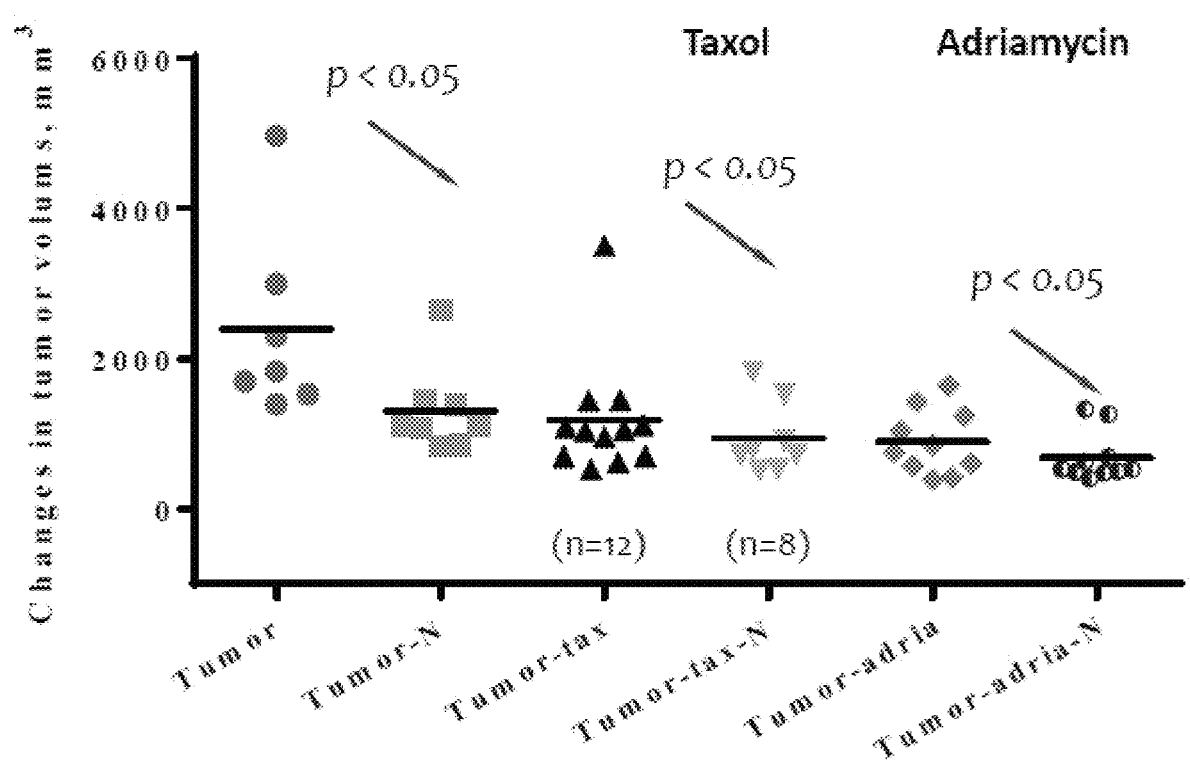
FIG. 18: Graph of the effect on tumor volume of addition of a nutritional supplement containing fish oil and selenium to Taxol and Adriamycin treatment regimes in an in vivo model of breast cancer.
Figure 19:
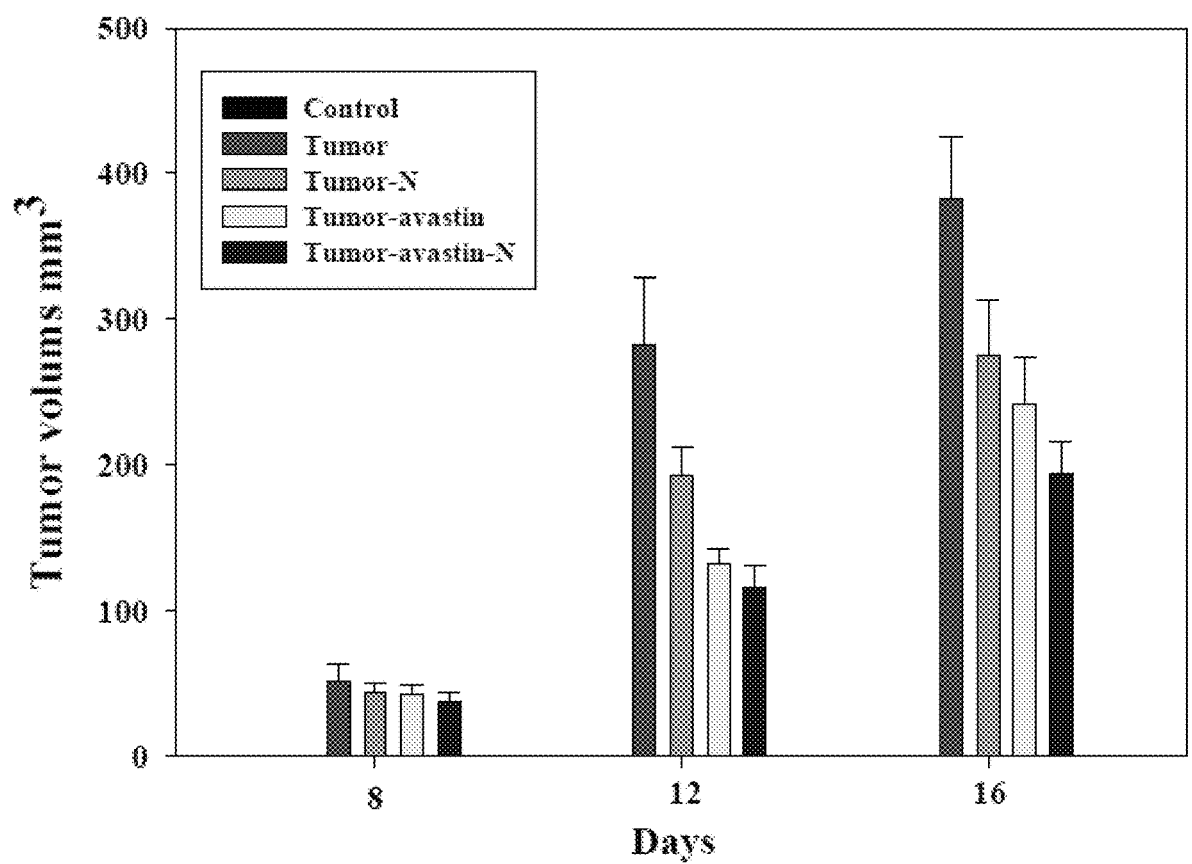
FIG. 19: Histogram of the effects of treatment with a nutritional supplement containing fish oil and selenium and Avastin on tumor volume.
Figure 20:
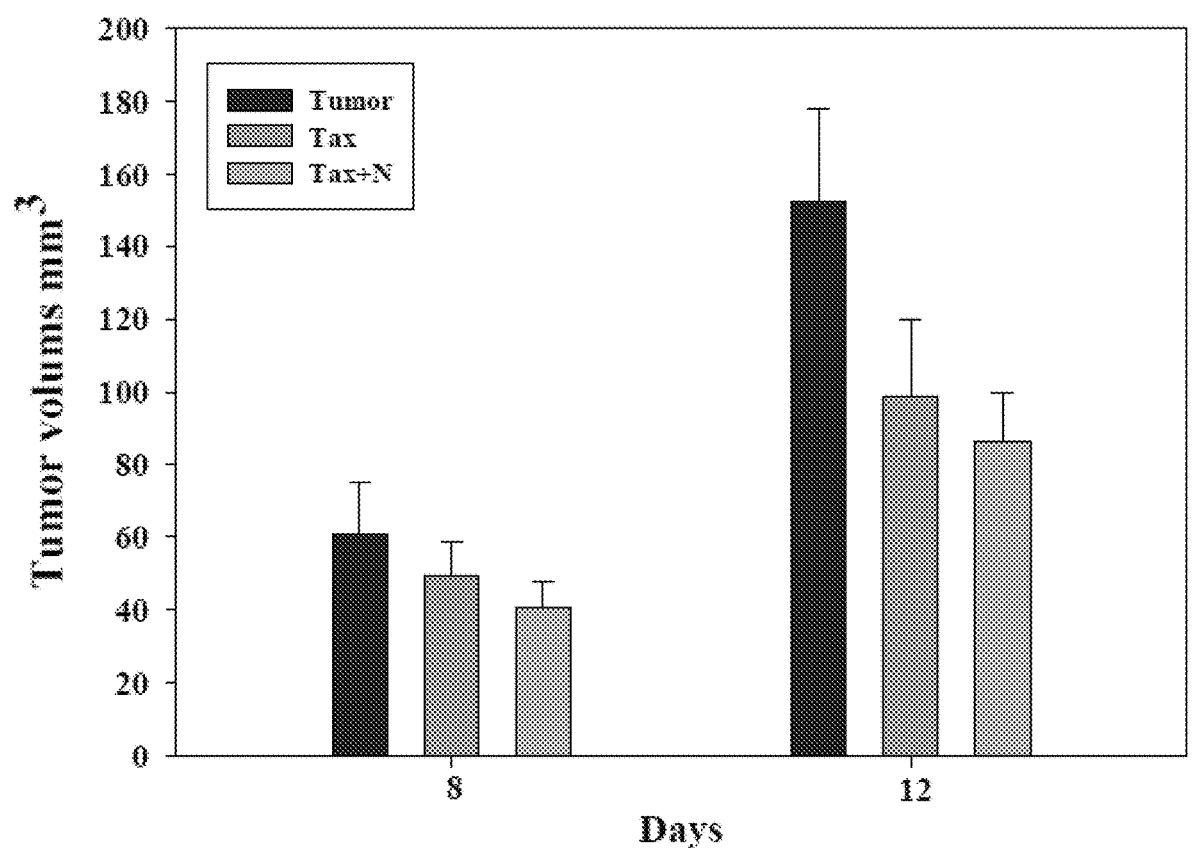
FIG. 20: Histogram of the effects of treatment with a nutritional supplement containing fish oil and selenium and Taxol on tumor volume.
Figure 21:
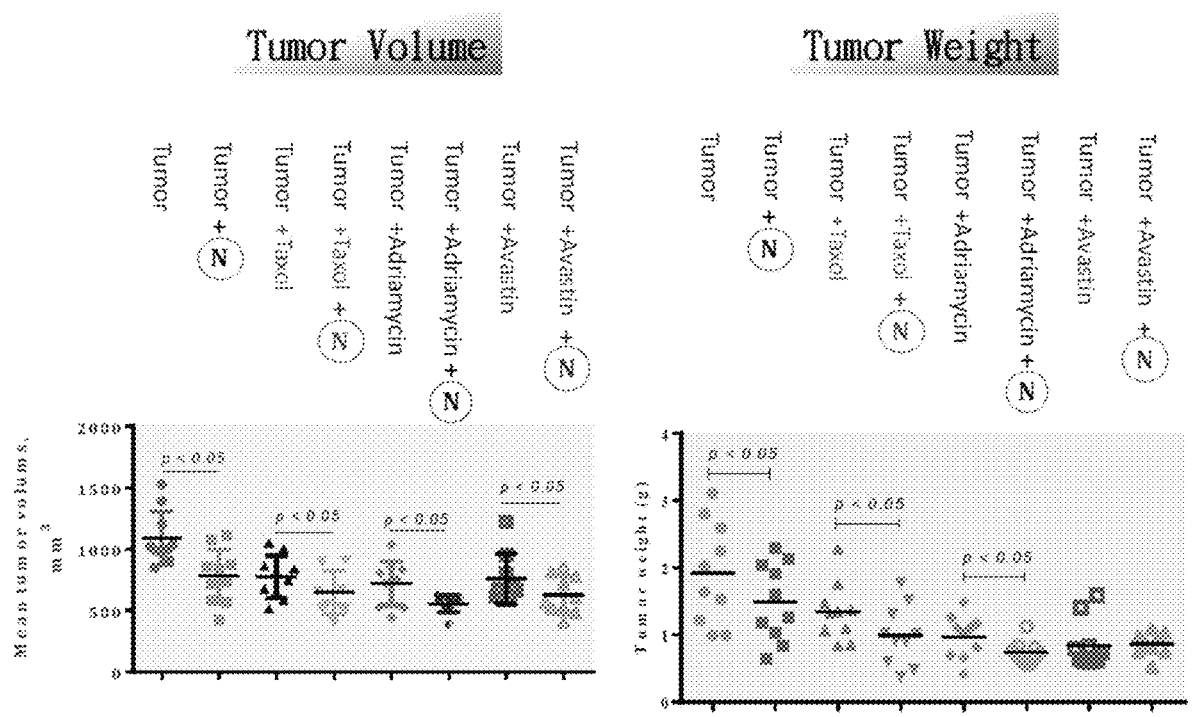
FIG. 21: Graphs of the effects of treatment with a nutritional supplement containing fish oil and selenium and/or chemotherapeutic agents on tumor volume and tumor weight.

Group 1, n = 10, Tumor positive control
Group 2, n = 10, Total Nutrition Formula
Group 3, n = 10, Taxol ® (paclitaxel)
(ip, 5 mg/kg every 4 days)
Group 4, n = 10, Taxol ® (ip, 5 mg/kg every 4 days) +
Total Nutrition Formula
Group 5, n = 10, Adriamycin ® (doxorubicin)
(iv, 2 mg/kg every 4 days)
Group 6, n = 10, Adriamycin ® (iv, 2 mg/kg every 4 days) +
Total Nutrition Formula FIG. 17 and FIG. 18 show typical data for tumor weight and volume (respectively) in the test groups of mice implanted with breast cancer cells as described in Table 2. As shown, the addition of a nutritional supplement containing fish oil and selenium to treatment regimes utilizing Taxol or Adriamycin results in a significant reduction in tumor weight relative to use of these chemotherapeutic agents alone. Similar studies were performed to determine the effect of a nutritional supplement of the inventive concept in combination with Avastin or Taxol. A nutritional supplement containing fish oil and selenium was provided at 0.4 g twice per day to mice implanted with tumor cells, where Avastin or Taxol was provided interperitoneally at 5 mg/kg every 4 days. The effect on tumor volume in mice treated with a nutritional supplement containing fish oil and selenium and Avastin can be seen in FIG. 19. The effect on tumor volume in mice treated with a nutritional supplement containing fish oil and selenium and Taxol can be seen in FIG. 20. An improvement in reduction in tumor volume is seen with co-treatment with the nutritional supplement with both Avastin and Taxol. Results of similar studies showing the effects of cotreatment with a nutritional supplement containing fish oil and selenium and Taxol, Adriamycin, or Avastin on tumor volume (left panel) and tumor weight (right panel) are shown in FIG. 21.

Figure 22:
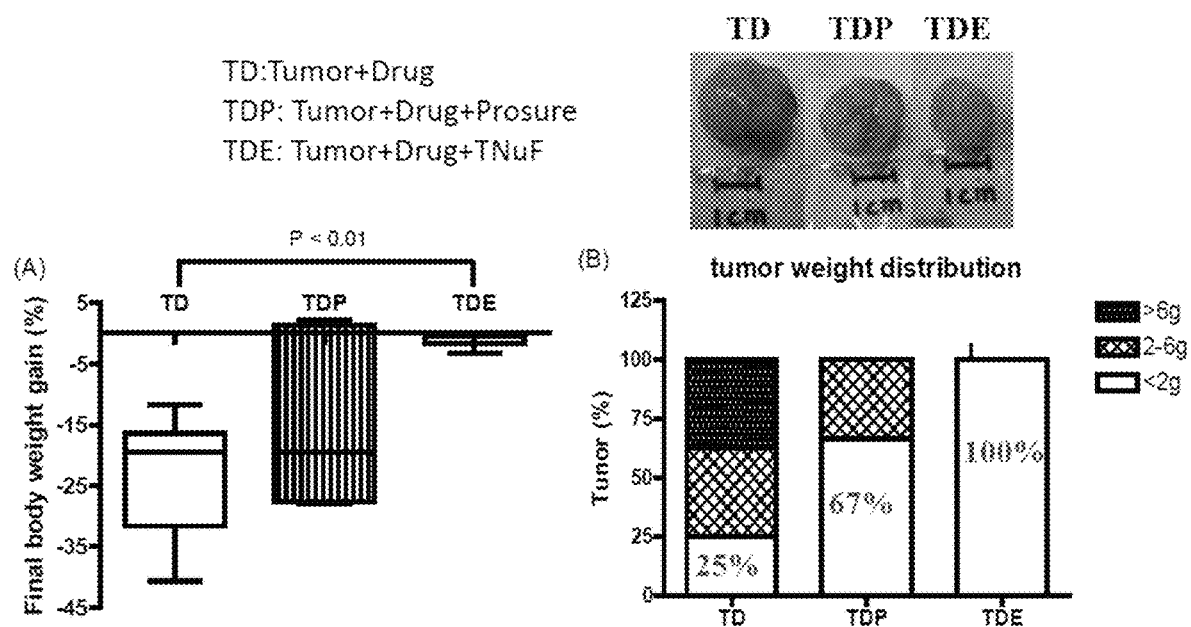
FIG. 22: Photographs and histograms of the effect of a prior art nutritional supplement and a nutritional supplement containing fish oil and selenium in combination with chemotherapy on tumor weight distribution and body weight gain.

To determine if the results of in vivo studies were influenced by general nutritional status of animal subjects receiving nutritional supplementation Inventors compared the results of cotreatment with a nutritional supplement containing fish oil and selenium ("TNuF") and equivalent caloric supplementation with a commercial nutritional supplement (Prosure™ "P"). As shown in FIG. 22 (upper panel), cotreatment with a chemotherapeutic drug and Prosure™ resulted in a slight reduction in apparent tumor size relative to treatment with only the chemotherapeutic drug. Cotreatment with a nutritional supplement containing fish oil and selenium and the chemotherapeutic drug, however, reduced apparent size of tumors by about 50% relative to subjects treated only with the chemotherapeutic drug. A similar effect is seen in tumor weight distribution (see 20180449S4, lower panel). It is apparent that the improvements in reducing tumor size and weight are not only a result of improvement in nutritional status.

Inhibition of Neovascularization/Angiogenesis

In many instances growth of solid tumors is promoted by angiogenesis and/or neovascularization, leading to the development of blood vessels within the tumor mass. Inventors have also found that a nutritional supplement containing fish oil and selenium can reduce angiogenesis/neovascularization in tumors, both alone and when used in combination with chemotherapeutic agents. Surprisingly, the Inventor also noted reduced angiogenesis/neovascularization effects for some chemotherapeutic agents alone. The Inventor believes that such a reduction in neovacularization induces oxidative stress in tumors and/or renders tumors so treated more susceptible to oxidative stress.

Figure 23:
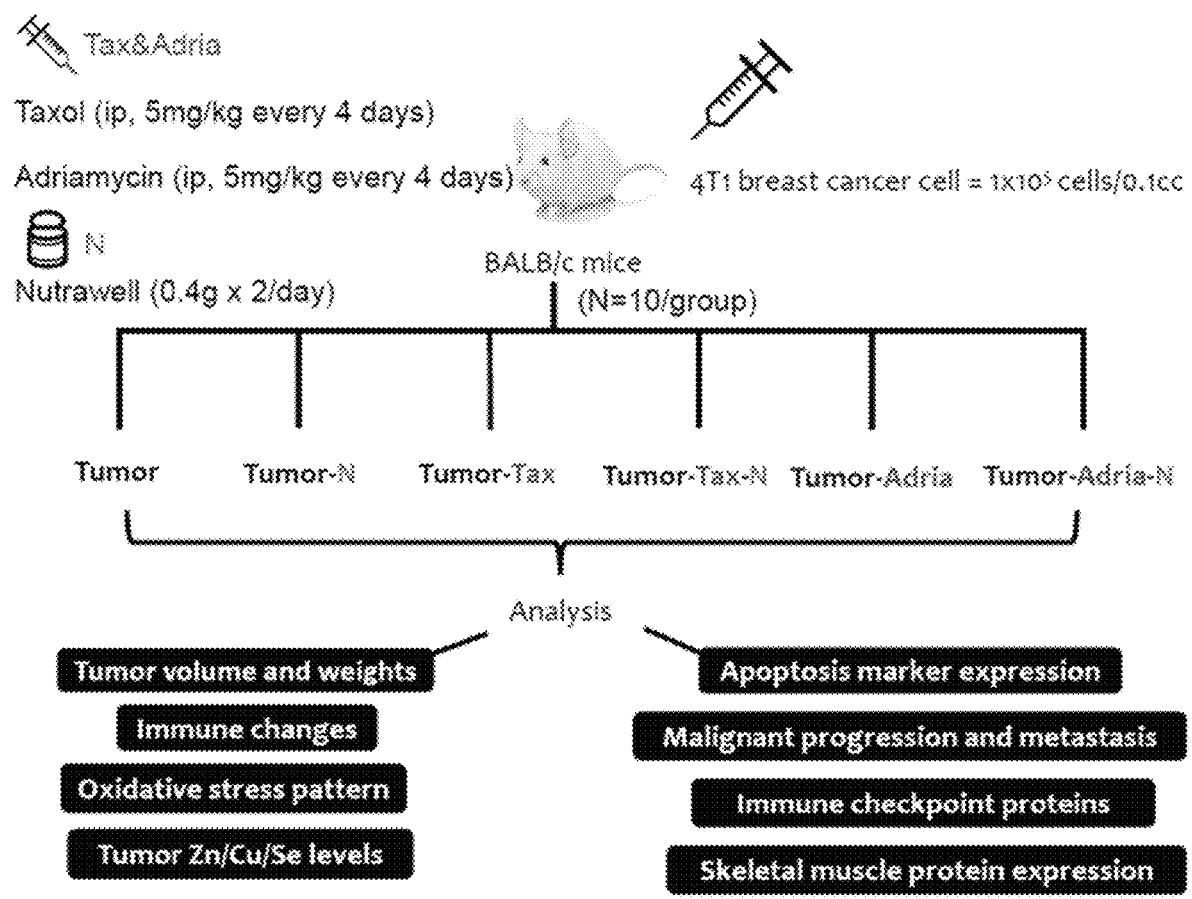
FIG. 23: Schematic depiction of a typical testing protocol for evaluating effects of treatment with a nutritional supplement containing fish oil and selenium in combination with Taxol or Adriamycin.
Figure 24:
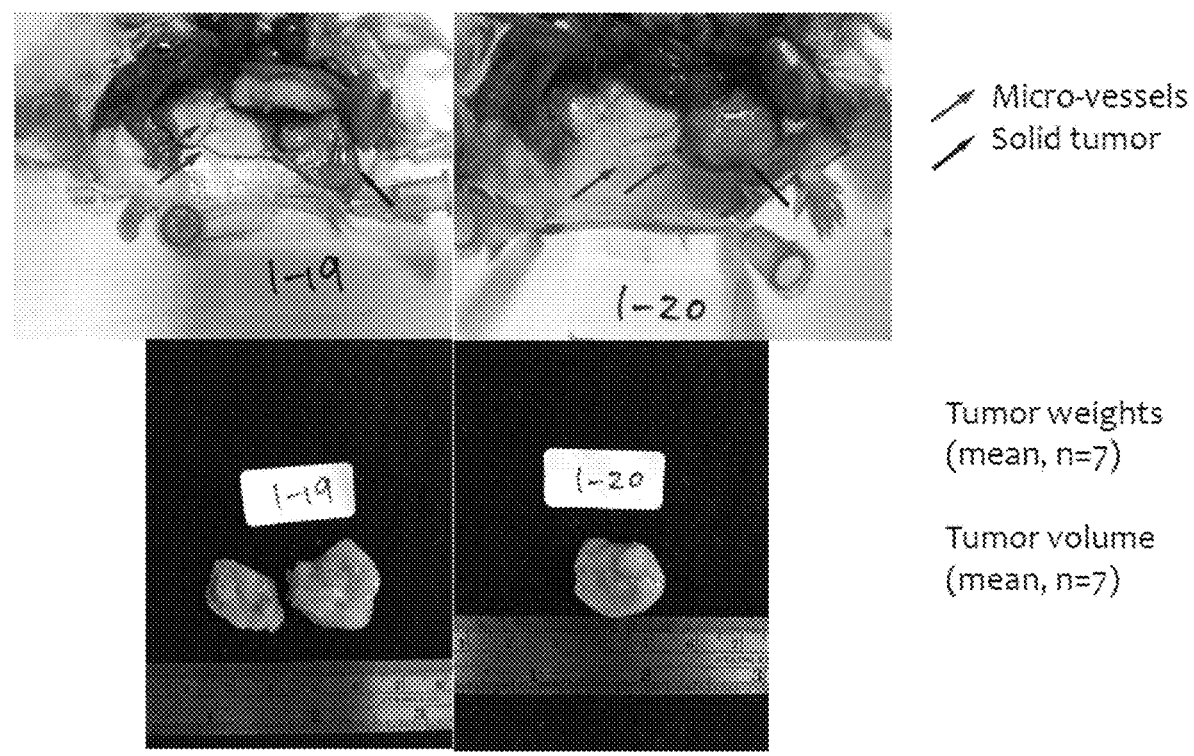
FIG. 24: Photographs showing tumors and associated blood vessels in mice from an untreated control group.
Figure 25:
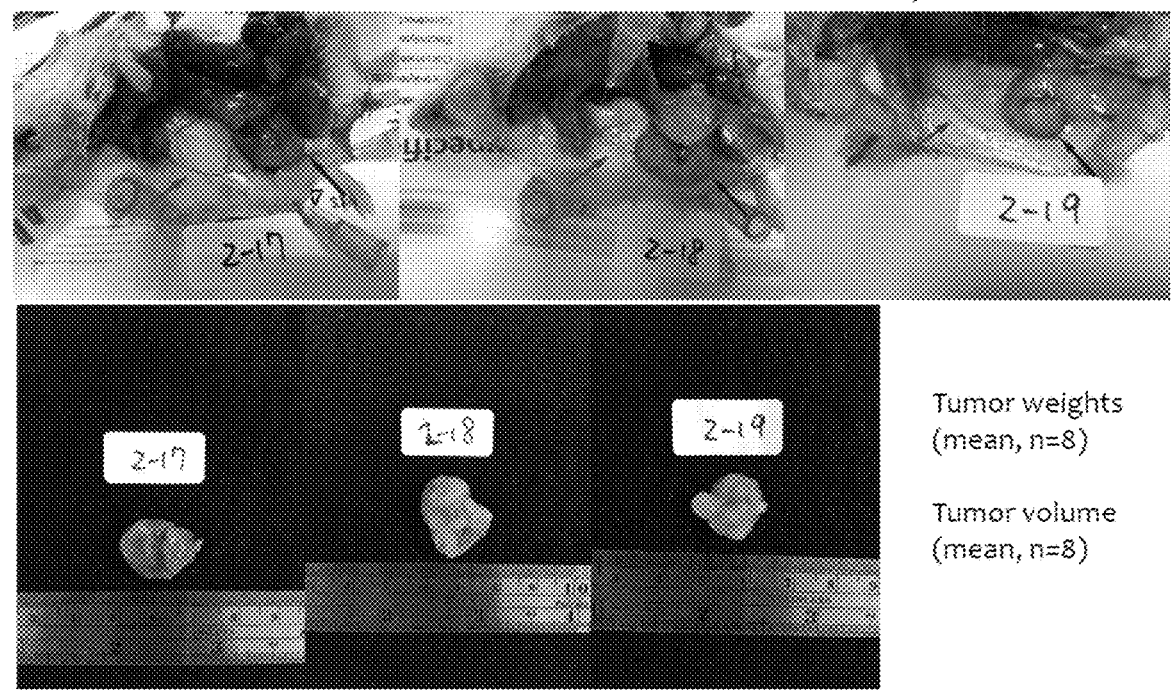
FIG. 25: Photographs showing tumors and associated blood vessels from mice treated with a nutritional supplement Photographs showing tumors.
Figure 26:
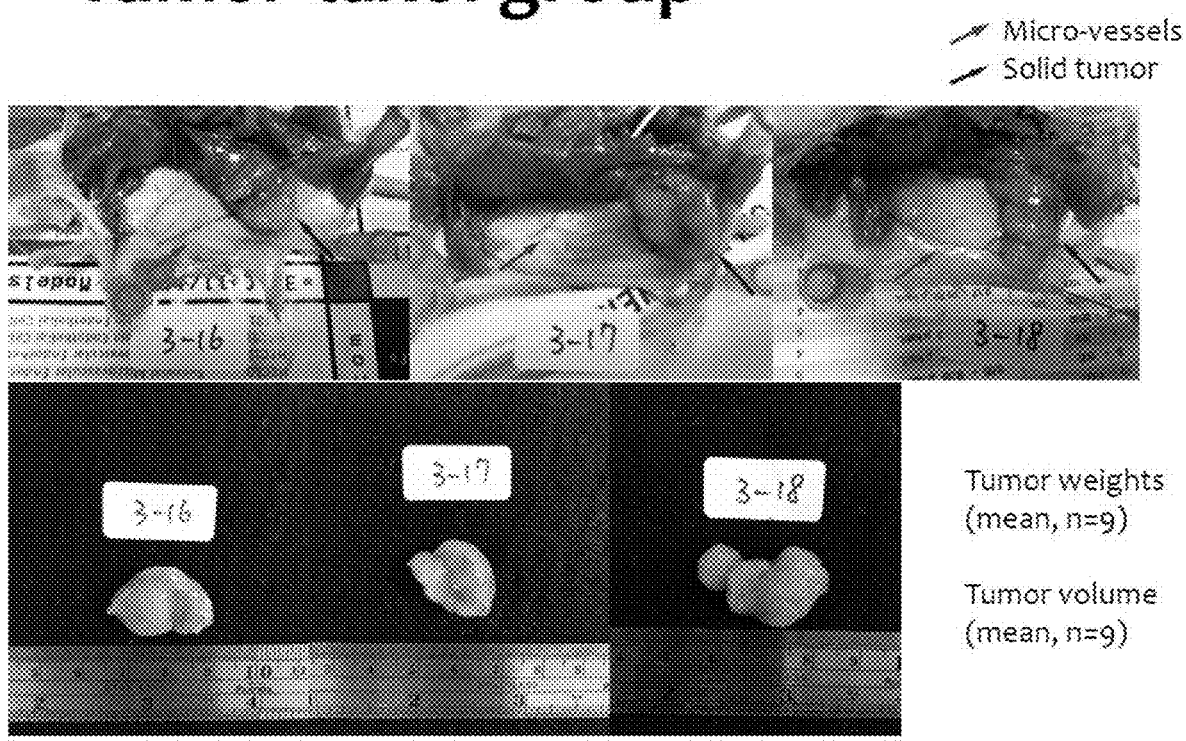
FIG. 26: Photographs showing tumors and associated blood vessels from mice treated with Taxol.
Figure 27:
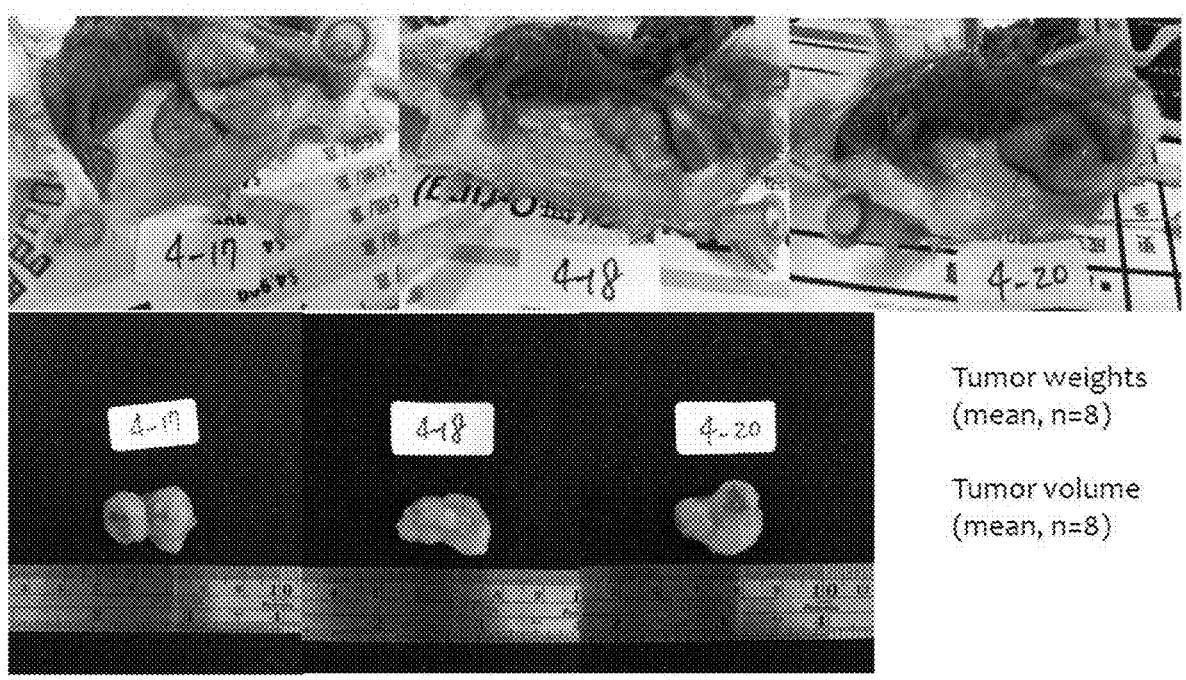
FIG. 27: Photographs showing tumors and associated blood vessels from mice treated with a combination of Taxol and a nutritional supplement containing fish oil and selenium.
Figure 28:
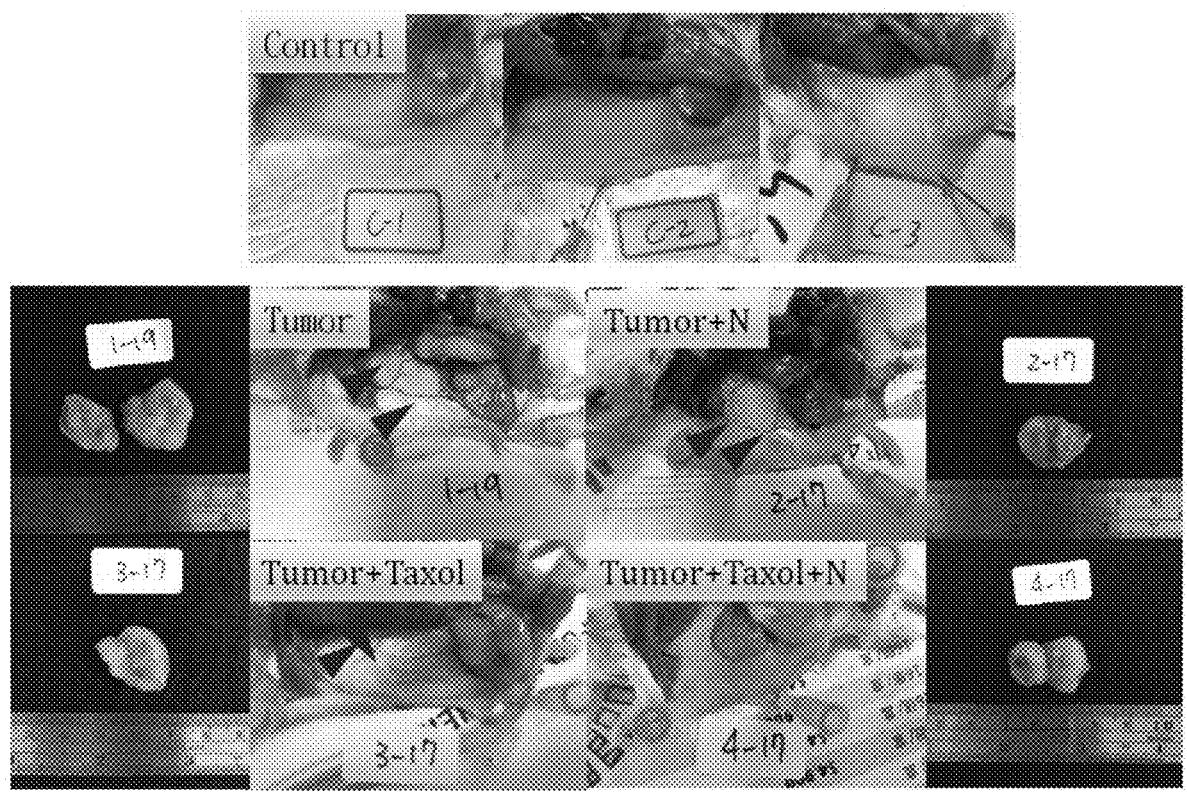
FIG. 28: Comparative photographs showing tumors and associated blood vessels from mice treated with either Taxol or a combination of Taxol and a nutritional supplement containing fish oil and selenium.

Inventors have found that the use of a nutritional supplement containing fish oil and selenium in combination with chemotherapeutic agents (e.g. taxol, adriamycin, avastin) has a direct and observable effect on vascularization of tumors in in vivo murine models of breast cancer. In an exemplary study mice were treated as shown in the scheme depicted in FIG. 23. FIG. 24 provides photographs of typical tumors and associated blood vessels in mice in the untreated control group. Several relatively large diameter blood vessels can be seen associated with the tumors. FIG. 25 provides similar photographs taken of mice in a group treated only with the nutritional supplement. The number of blood vessels associated with the tumors is reduced relative to those of the untreated control group, as is their diameter. FIG. 26 and FIG. 27 provide photographs of typical tumors taken from mice in a group treated with Taxol and treated with Taxol in combination with a nutritional supplement containing fish oil and selenium ("N"), respectively. Surprisingly, treatment with Taxol alone was found to reduce the number of blood vessels associated with the tumor and also reduce their diameter, which is not a known effect of treatment with this chemotherapeutic drug (see FIG. 26). As shown in FIG. 27, cotreatment with Taxol and a nutritional supplement containing fish oil and selenium resulted in a dramatic reduction in tumor-associated blood vessels. Similar results were found in the studies shown in FIG. 28.

Figure 29:
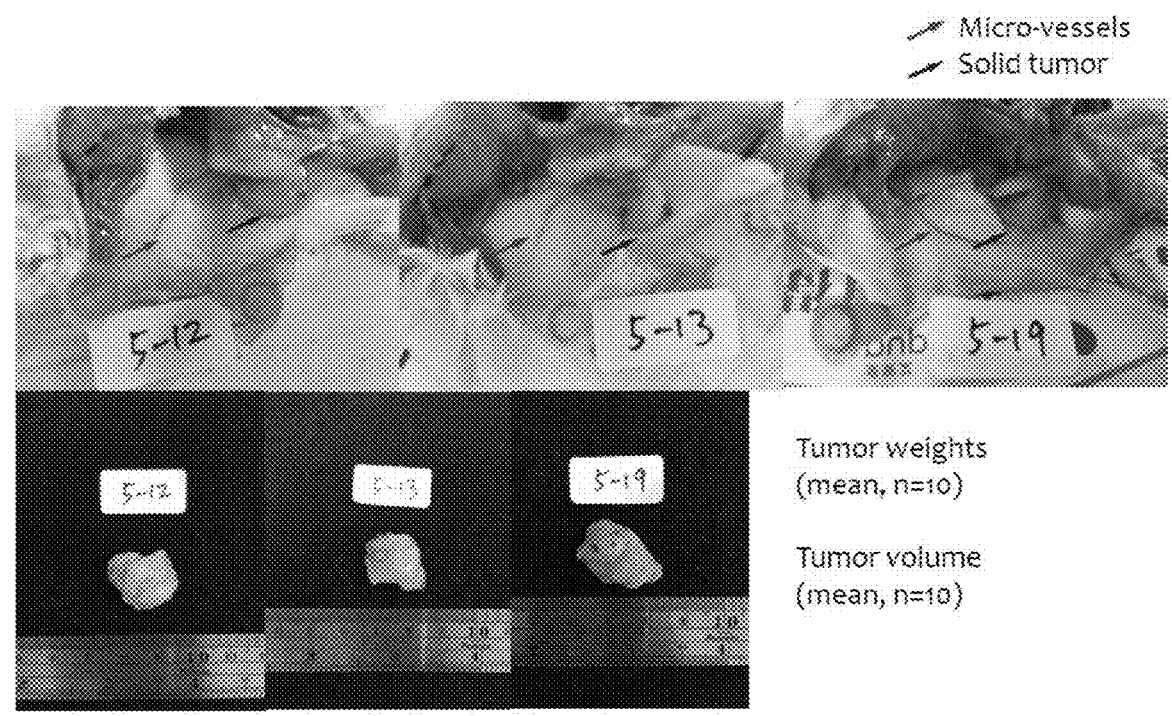
FIG. 29: Photographs showing tumors and associated blood vessels from mice treated with Adriamycin.
Figure 30:
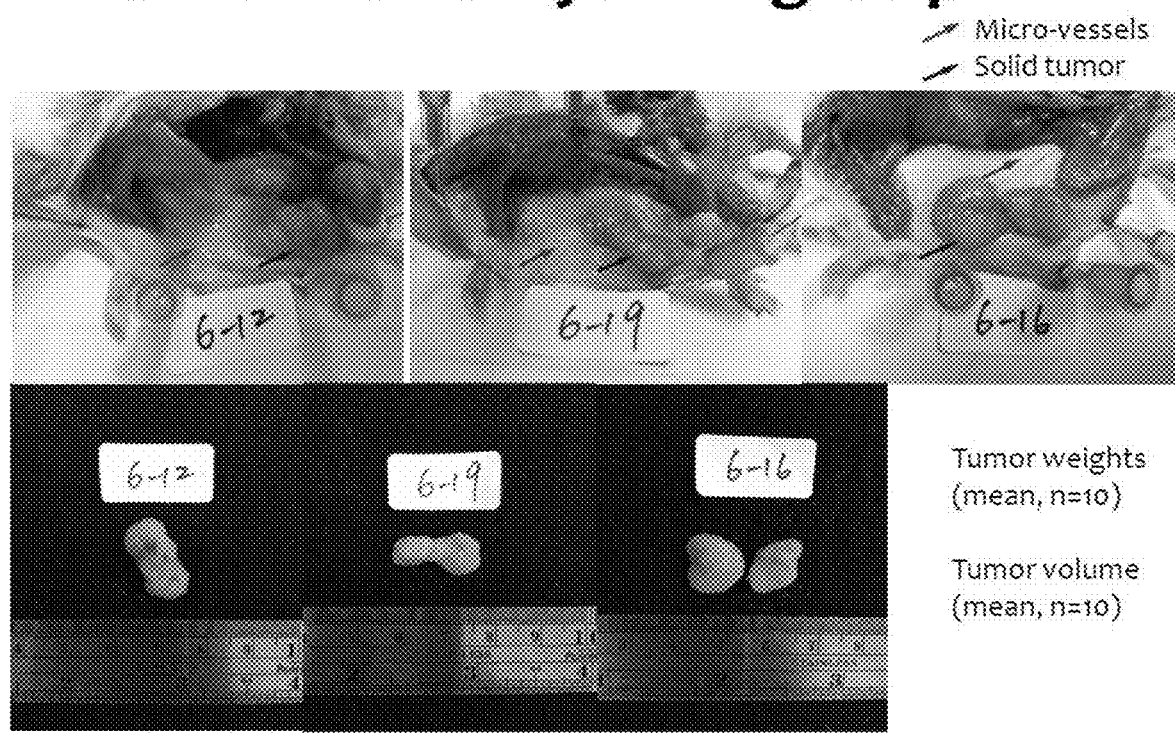
FIG. 30: Photographs showing tumors and associated blood vessels from mice treated with a combination of Adriamycin and a nutritional supplement containing fish oil and selenium.
Figure 31:
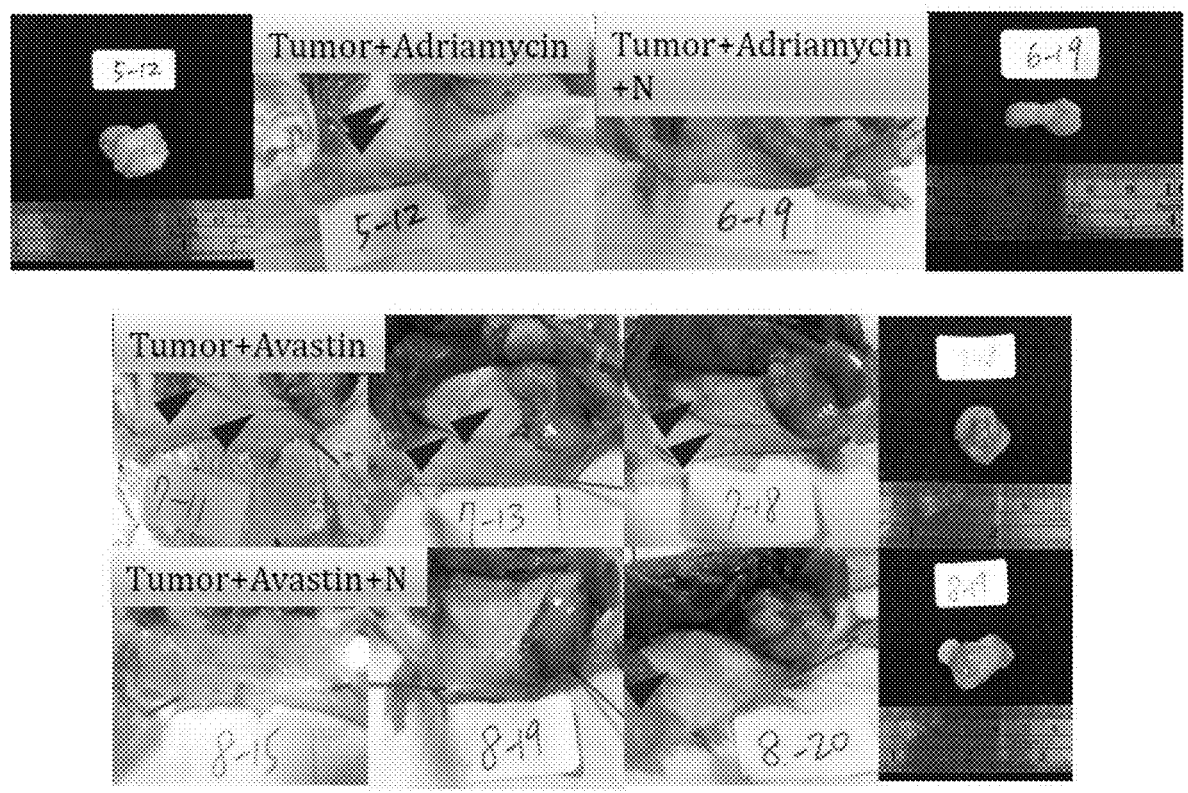
FIG. 31: Comparative photographs showing tumors and associated blood vessels from mice treated with a combination of Adriamycin or a combination of Adriamycin and a nutritional supplement containing fish oil and selenium.

FIG. 29 and FIG. 30 provide photographs of typical tumors taken from mice in a group treated with Adriamycin and with Adriamycin in combination with a nutritional containing fish oil and selenium, respectively, in a similar study. Similar results were found in separate but similar studies on the effects of a nutritional supplement containing fish oil and selenium in combination with either Adriamycin or Avastin, as shown in FIG. 31. In all instances treatment with a nutritional supplement containing fish oil and selenium significantly reduced vascularization of the tumors and significantly reduced tumor volume relative to similar treatment without the nutritional supplement. It is evident that nutritional supplements can reduce vascularization of solid tumors, and can enhance the reduction in vascularization of solid tumors seen in treatment with conventional chemotherapeutic agents.

Figure 32:
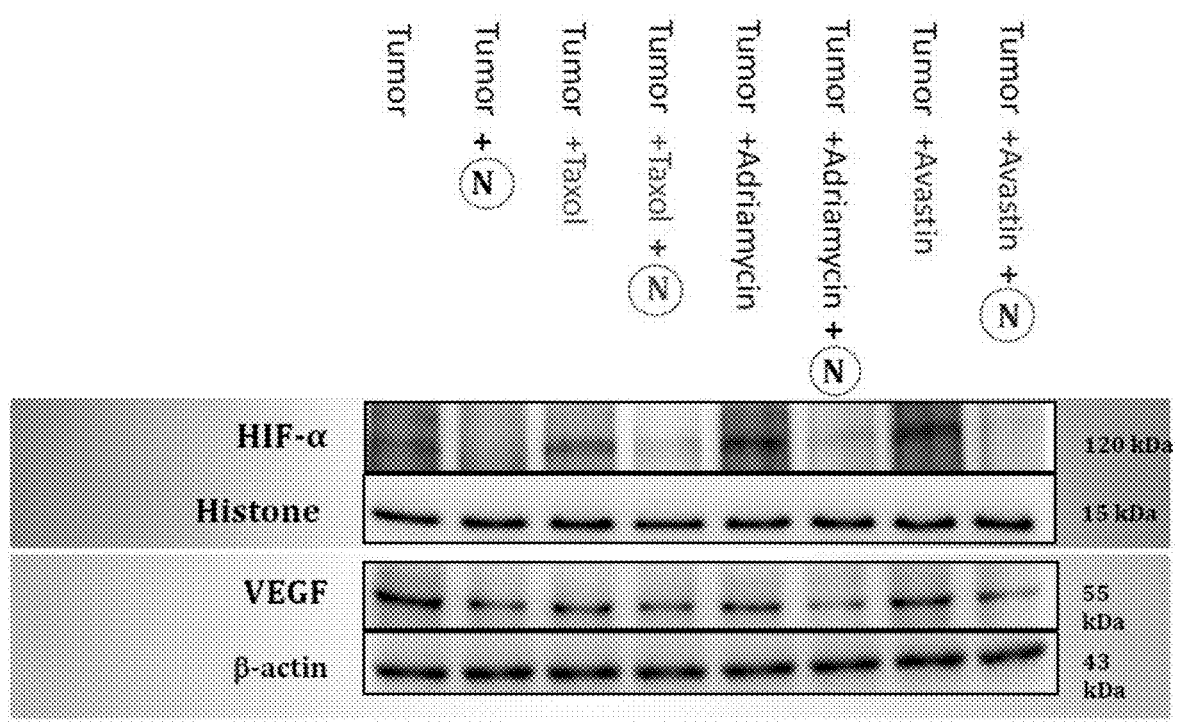
FIG. 32: Western blots showing the effect of a nutritional supplement containing fish oil and selenium in combination with chemotherapeutic agents on tumor expression of oxidative stress (i.e. HIF-$\alpha$) and angiogenesis (i.e. VEGF) markers in an in vivo model of human cancer. Actin is included as a control.
Figure 33:
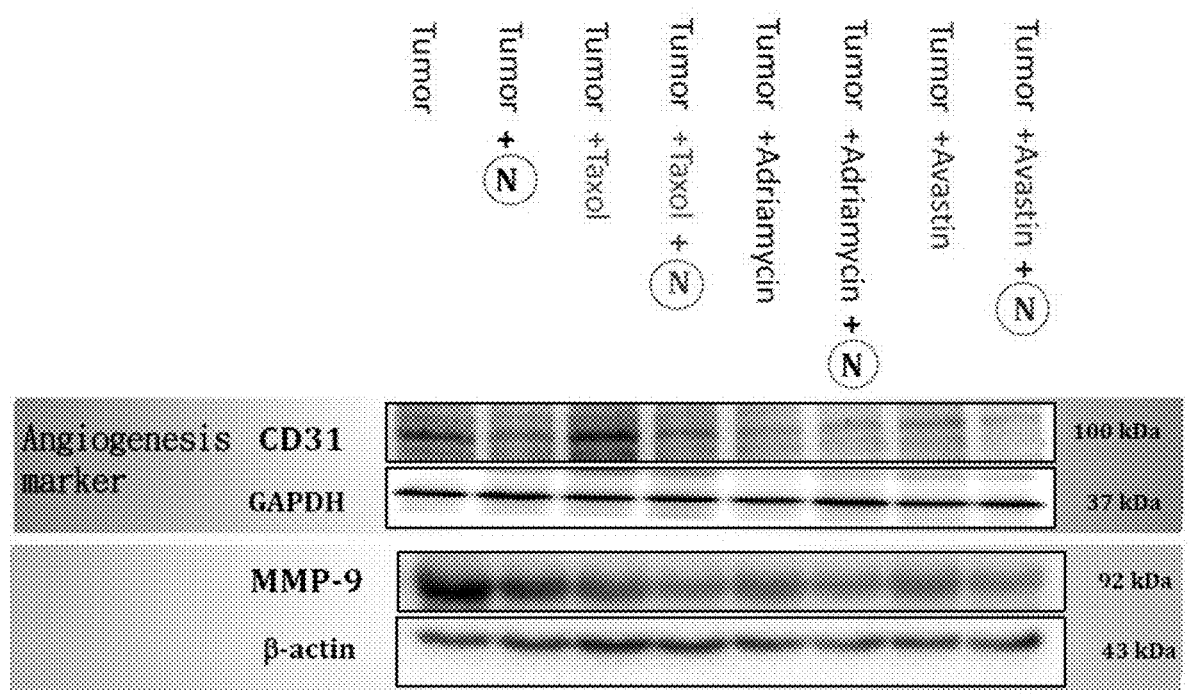
FIG. 33: Western blots showing the effect of a nutritional supplement containing fish oil and selenium in combination with chemotherapeutic agents on tumor expression of angiogenesis (i.e. CD31) and metastasis (i.e. MMP-9) markers in an in vivo model of human cancer. Actin is included as a control.

The effects on angiogenesis/neovascularization of treatment with a supplement containing fish oil and selenium and chemotherapeutic agents can also be observed on a molecular level. VEGF and CD31 are markers related to tumor angiogenesis, via the HIF-α pathway. FIG. 32 shows a Western blot of HIF-α and VEGF in tumors treated with a nutritional supplement containing fish oil and selenium ("N"), Taxol, Adriamycin, Avastin, and the nutritional supplement in combination with these chemotherapeutic agents. As shown, the nutritional supplement reduces HIF-α levels, where chemotherapeutic agents have relatively little effect. Similar reductions are seen in VEGF for both a nutritional supplement containing fish oil and selenium and, to a lesser extent, Taxol and Adriamycin. In all instances the combination of the nutritional supplement and a chemotherapeutic agent provides a dramatic reduction in HIF-α and in VEGF. Results of similar studies in which CD31 is characterized are shown in FIG. 33. Nutritional supplement containing fish oil and selenium provides a dramatic reduction in CD31, with similar reductions seen following treatment with Adriamycin and Avastin. Even greater reductions in CD31 are found following cotherapy with the nutritional supplement and the chemotherapeutic agents.

Effects on Cell Cycle Phase Distribution

Figure 34:
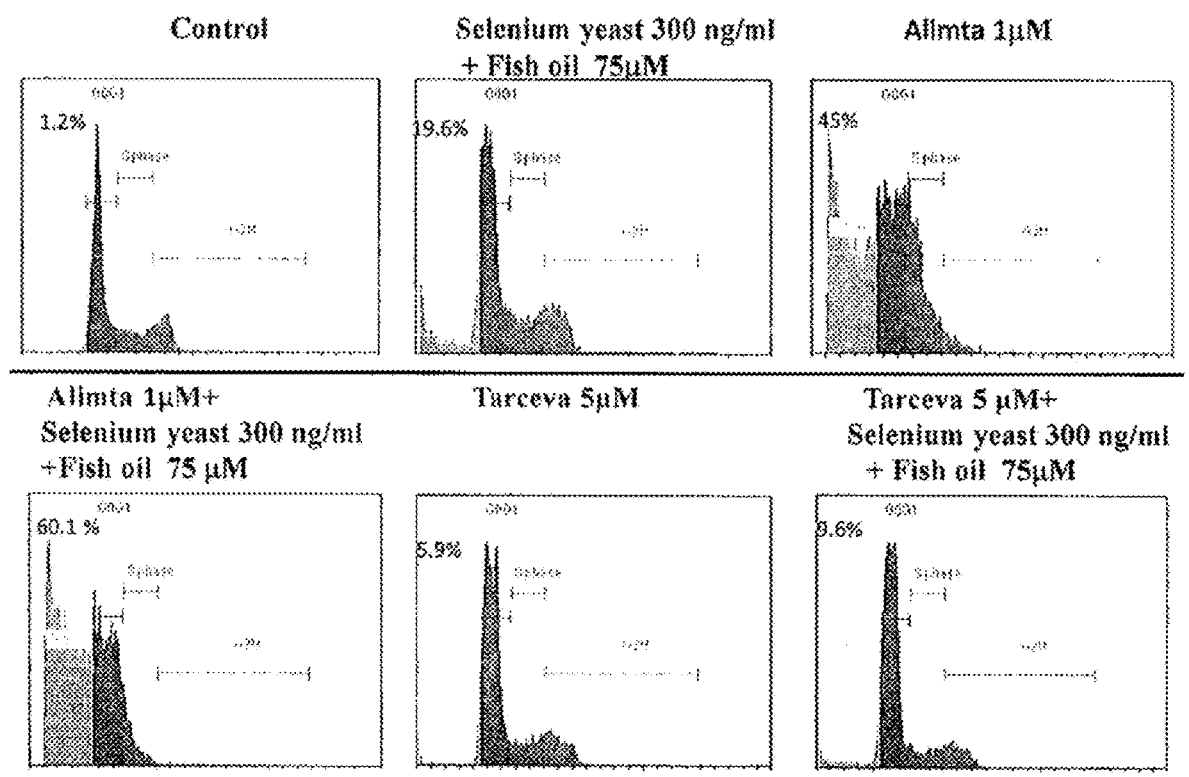
FIG. 34: Distribution of cell cycle phases of A549 tumor cells treated with a chemotherapeutic agent (Alimta, 1 µM or Tarceva, 5 µM) and a nutritional supplement containing fish oil and selenium.

The Inventor has found that cotherapy with a nutritional supplement containing fish oil and selenium and chemotherapy drugs also has a profound effect on the cell cycle phase distribution of cancer cells, both in vivo and in vitro. As shown in FIG. 34, A549 lung cancer cells show a slight shift to sub-G1 when treated with a supplement containing fish oil and selenium, and a moderate shift to sub-G1 when treated with Alimta. Cotreatment with both the nutritional supplement and Alimta shows a greater than additive shift to sub-G1, indicating a synergistic effect. Treatment with Tarceva alone shows almost no effect on cell cycle distribution relative to untreated control cells, however a significant shift to sub-G1 is found when used in combination with a nutritional supplement containing fish oil and selenium. Results of a similar study with the chemotherapeutic drug Tarceva are shown in 8FIG. 3B. Results are summarized in Table 3.

TABLE 3

| | SubG1 | G0/G1 | S | G2/M |
|---|---|---|---|---|
| Control | 1.2% | 62.1% | 17.6% | 20.3% |
| Selenium 300 ng/ml + Fish oil 75 μM | 19.6% | 60.6% | 19.2% | 20.3% |
| Alimta 1 μM | 45% | 58.4% | 36.3% | 5.3% |
| Alimta 1 μM + Fish oil 75 μM Selenium 300 ng/mL | 60.1% | 80.9% | 17.2% | 1.8% |
| Tarceva 5 μM | 5.9% | 70.9% | 14.2% | 14.8% |
| Tarceva 5 μM + Fish oil 75 μM Selenium 300 ng/mL | 9.6% | 77.5% | 11% | 11.6% |

The concentration of fish oil represents its DHA content
Each gram of fish oil contains 220 mg DHA and 330 mg EPA It is apparent that treatment with a supplement containing fish oil and selenium in combination with various chemotherapeutic drugs can shift the cell cycle distribution of cancer cells towards sub-G1 phase. It should be appreciated that sub-G1 phase is associated with apoptosis; as such combined therapy with a chemotherapeutic drug and a supplement containing fish oil and selenium can be useful in inducing apoptosis and/or apoptic events in cancer cells.

Apoptosis/Autophagy

Figure 35:
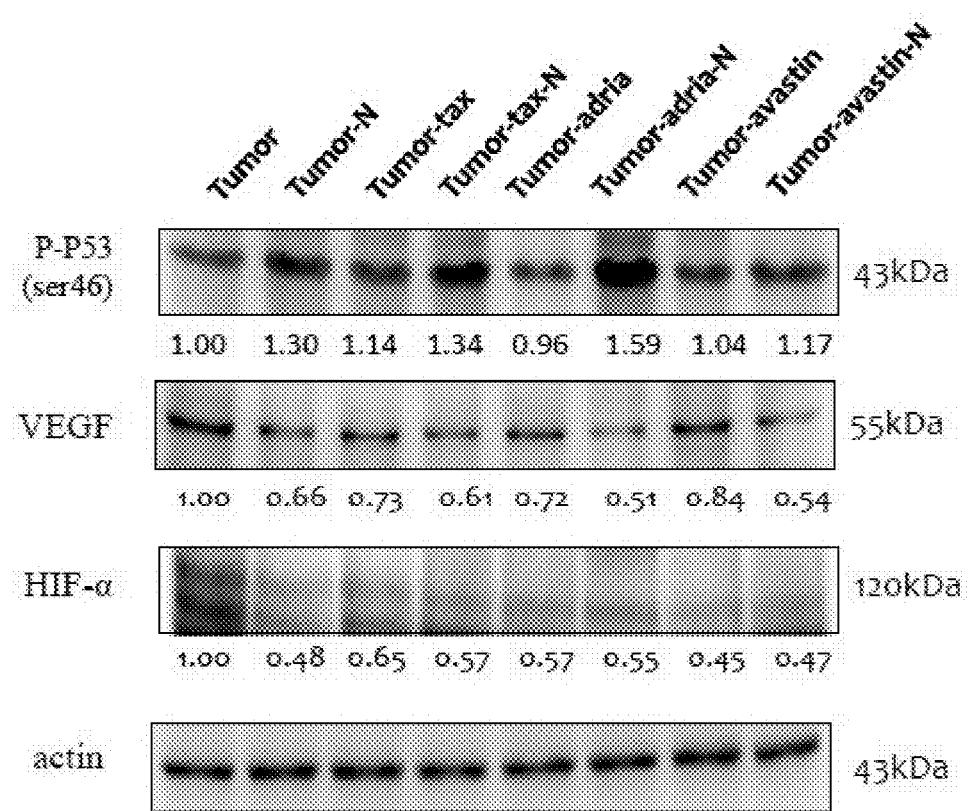
FIG. 35: Western blots showing the effect of a nutritional supplement containing fish oil and selenium in combination with chemotherapeutic agents on tumor expression of various apoptosis markers in an in vivo model of breast cancer. Actin is included as a control.

As noted above, studies of cell cycle phase distribution suggest that cotherapy with a supplement containing fish oil and selenium in combination with a chemotherapy drug can induce apoptosis and/or apoptic events in cancer cells. Inventors have found that nutritional supplements containing fish oil and selenium are effective in enhancing apoptosis in tumors in in vivo models for breast cancer. For example, FIG. 35 shows the effect of use of such a nutritional supplement, chemotherapeutic agents Taxol, Avastin, or Adriamycin, and these chemotherapeutic agents in combination with the nutritional supplement on expression of apoptosis markers (specifically VEGF, p53, and HIF-α) in advanced tumors in mouse injected with breast cancer cells.

As shown, the use of the nutritional supplement increases the expression of p53, while decreasing the expression of VEGF and HIF-α. This effect is seen when the nutritional supplement is used alone or in combination with a chemotherapeutic agent, with combination providing an enhanced effect.

Figure 36:
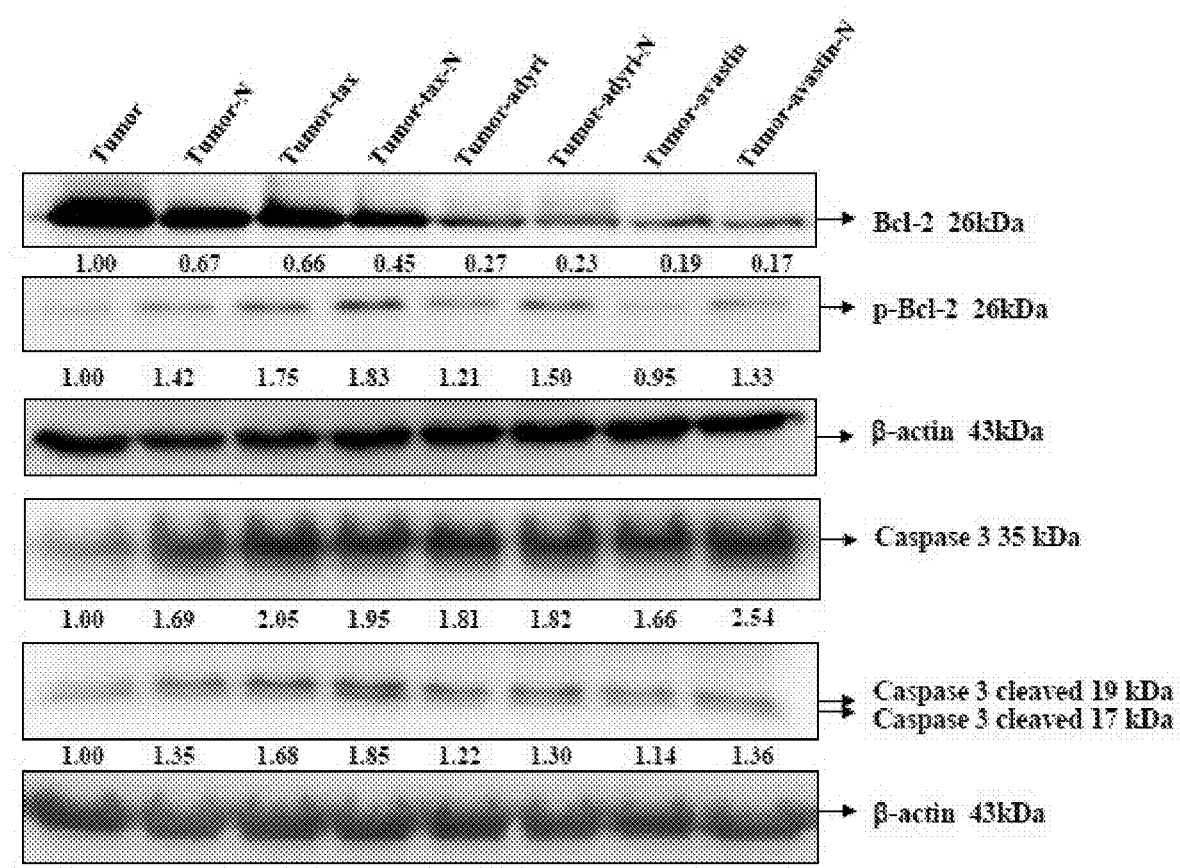
FIG. 36: Western blots showing the effect of a nutritional supplement containing fish oil and selenium in combination with chemotherapeutic agents on tumor expression of Bcl-2, p-Bcl-2, and Caspase 3 apoptosis markers in an in vivo model of breast cancer. Actin is included as a control
Figure 37:
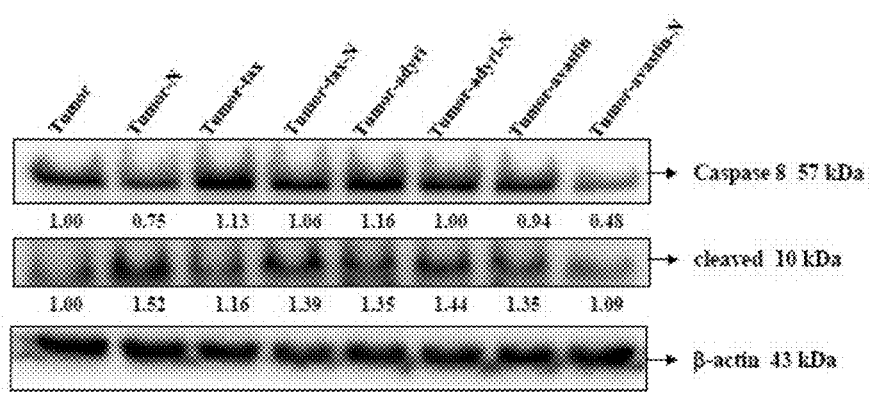
FIG. 37: Western blots showing the effect of a nutritional supplement containing fish oil and selenium in combination with chemotherapeutic agents on tumor expression of Caspase 8 apoptosis marker in an in vivo model of breast cancer. Actin is included as a control.
Figure 38:
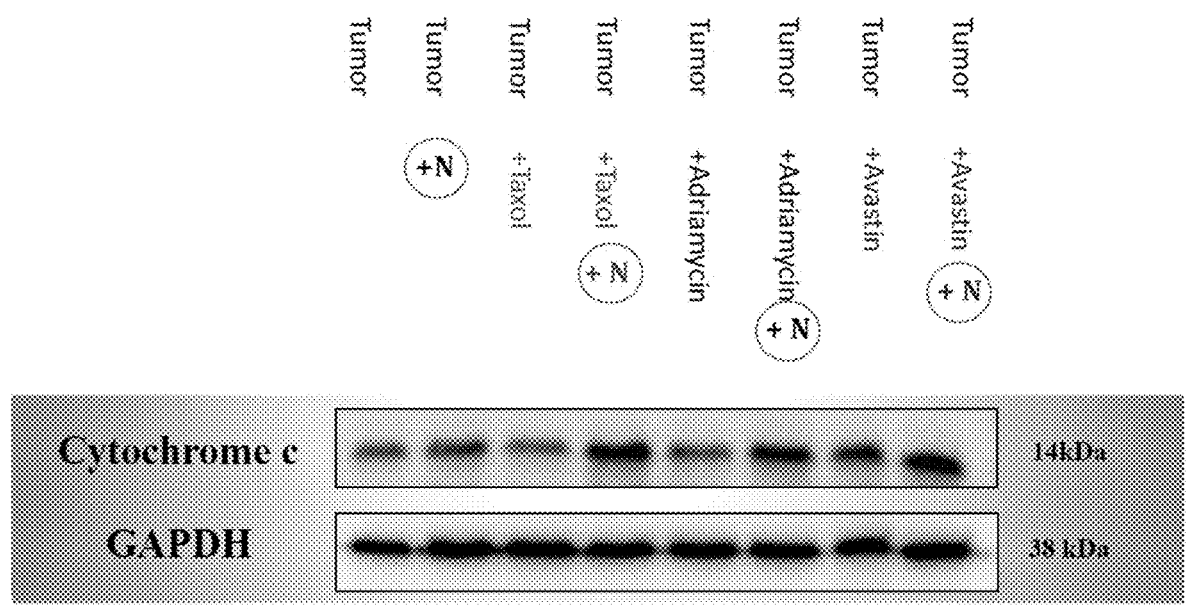
FIG. 38: Western blots showing the effect of a nutritional supplement containing fish oil and selenium in combination with chemotherapeutic agents on expression of Cytochrome C in an in vivo model of breast cancer. Actin is included as a control.

Results of similar studies directed to Bcl-2, p-Bcl-2, and Caspase 3 are shown in FIG. 36; results for similar studies directed to Caspase 8 are shown in FIG. 37. As shown, use of a nutritional supplement containing fish oil and selenium decreases expression of Bcl-2 and increases expression of p-Bcl-2 and Caspase 3, both when used in isolation and when used in combination with chemotherapeutic drugs. Expression of Caspase 8 is reduced, both when used in isolation and when used in combination with chemotherapeutic drugs. FIG. 38 shows the effects treatment with a nutritional supplement containing fish oil and selenium ("N"), Taxol, Adriamycin, Avastin, and combined treatment on Cytochrome C. As shown, treatment with the supplement provides a slight increase in Cytochrome C, with little to no increase found on treatment with Taxol or with Adriamycin. These effects are enhanced, in several instances synergistically, when a nutritional supplement containing fish oil and selenium is used in combination with a chemotherapeutic drug.

Figure 39:
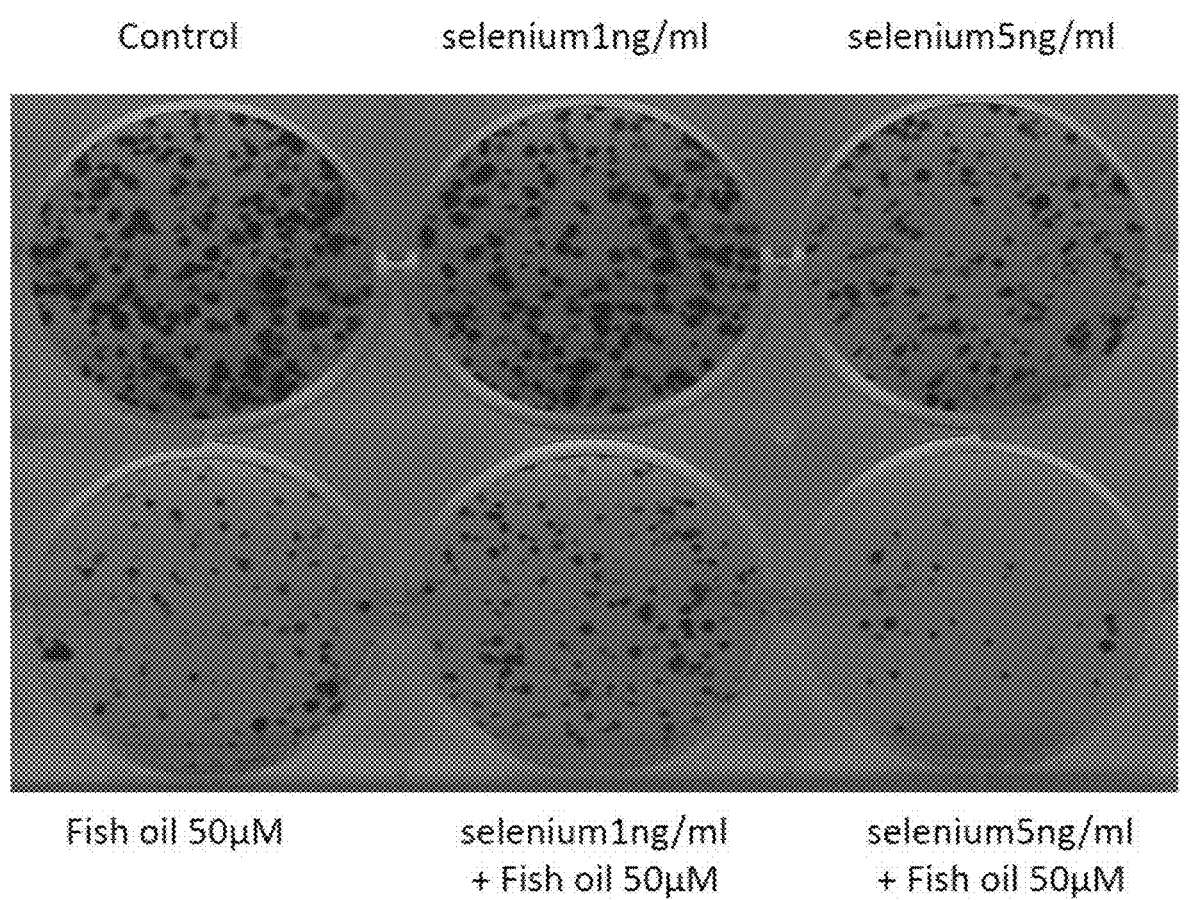
FIG. 39: Photographs of cell culture plates showing apoptosis in A549 lung cancer cells treated with a supplement containing fish oil and selenium.
Figure 40:
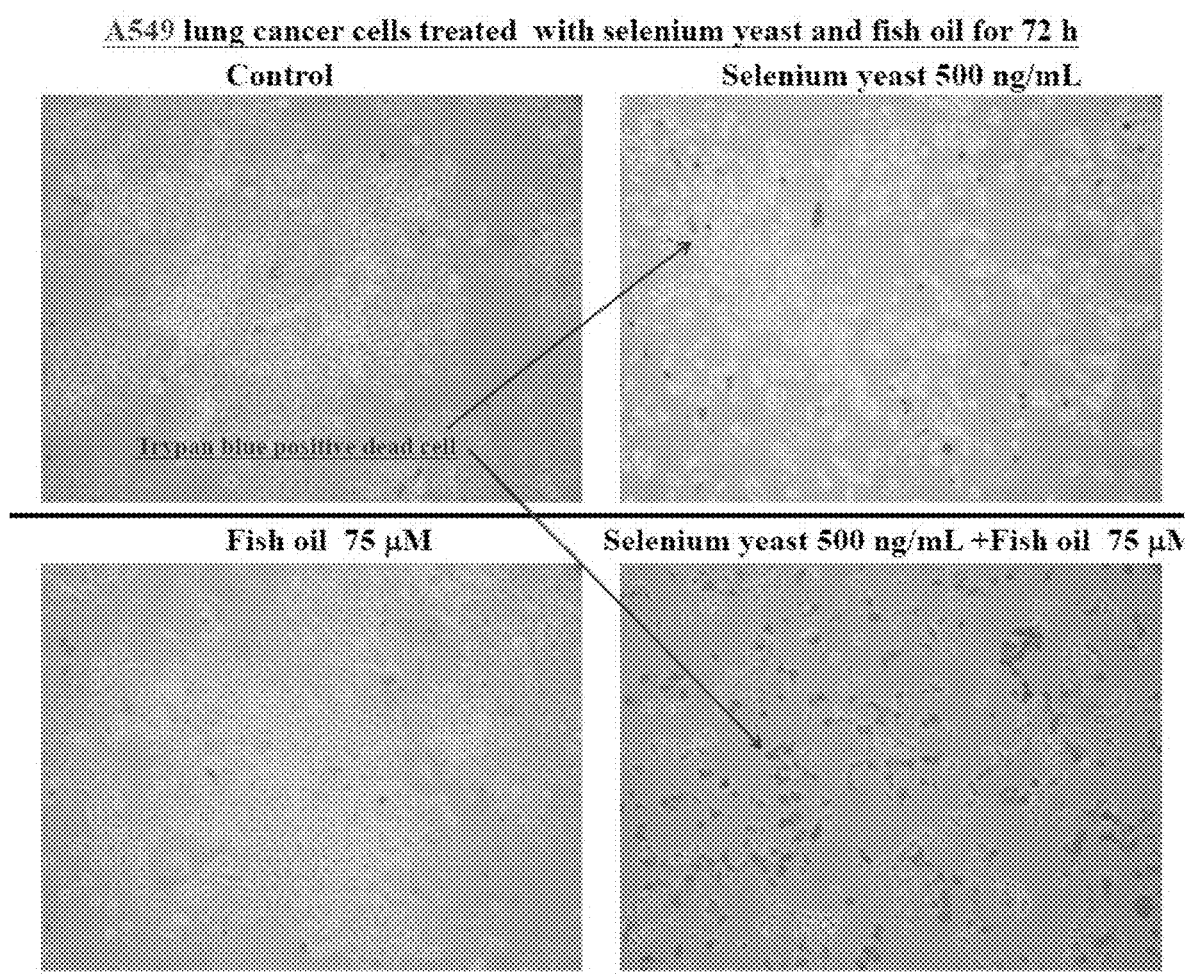
FIG. 40: Trypan blue staining of A549 lung cancer cells treated with a supplement containing fish oil and selenium.

In addition to biochemical markers of apoptosis, apoptic effects can be observed directly. For example, as shown in FIG. 39, growth of A549 cells in culture is slightly impacted by exposure to a supplement containing selenium or a supplement containing fish oil, but is dramatically impacted by a supplement containing both fish oil and selenium. Similarly, trypan blue staining of A549 cells in culture show only slight effects in inducing cell death when exposed to a supplement containing selenium or a supplement containing fish oil, but shows a dramatic increase in cell death when exposed to a supplement containing both fish oil and selenium, as shown in FIG. 40. While either of selenium or fish oil shows some effect the effects of these in combination is clearly greater than additive (i.e. synergistic).

Oxidative Stress/Hypoxia

Figure 41:
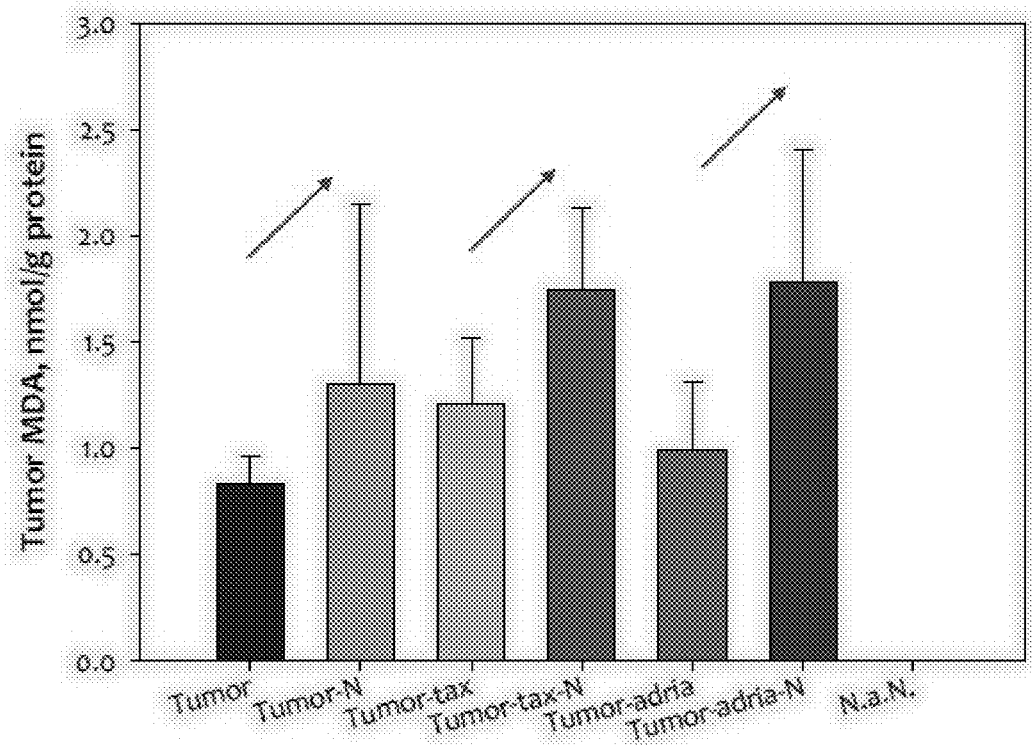
FIG. 41: Histogram of the effect of a nutritional supplement containing fish oil and selenium in combination with chemotherapeutic agents on plasma concentrations of tumor MDA in an in vivo model of breast cancer.
Figure 42:
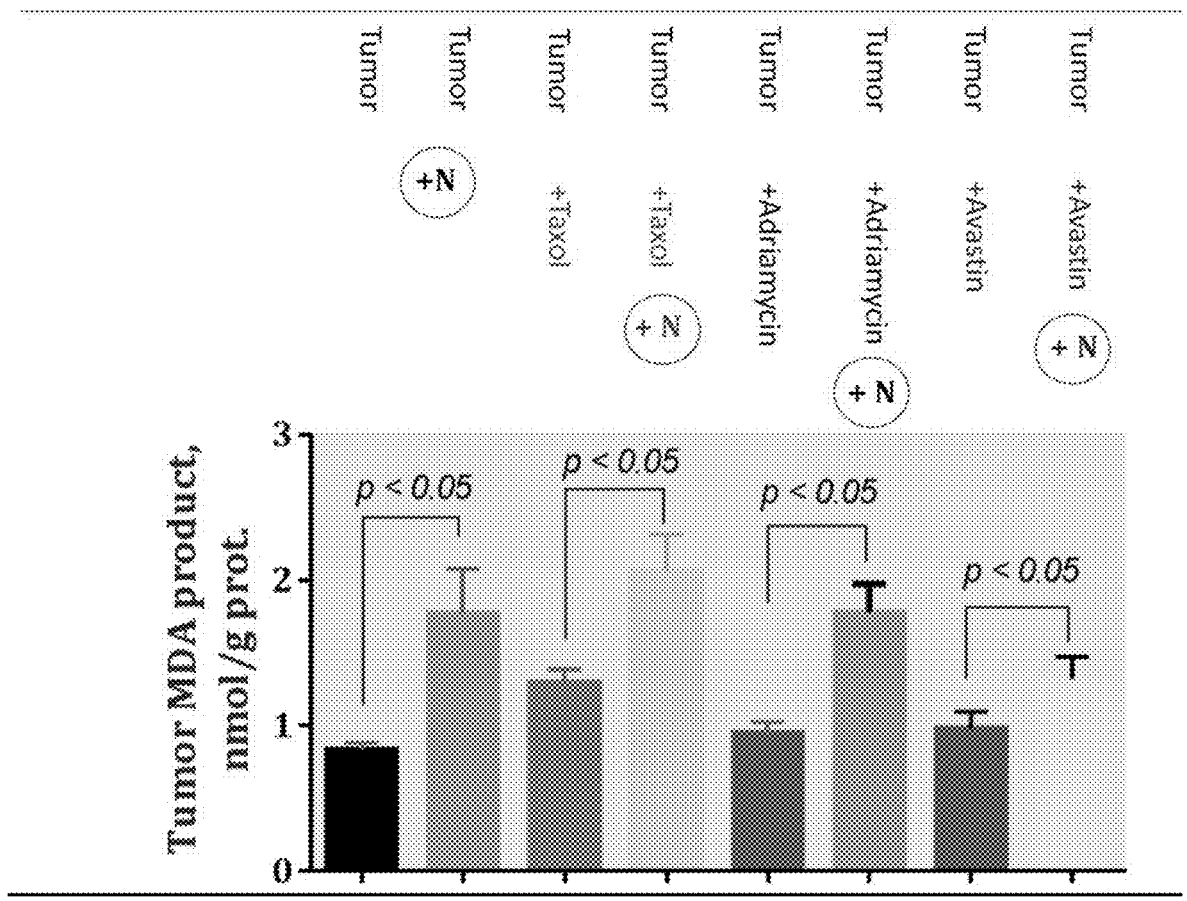
FIG. 42: Histogram of the effect of a nutritional supplement containing fish oil and selenium in combination with chemotherapeutic agents on concentrations of tumor MDA in an in vivo model of breast cancer.

The Inventor have found that nutritional supplements of the inventive concept are effective in enhancing oxidative stress of tumors in in vivo models for breast cancer (e.g. inhibiting the ability of a tumor to respond to oxidative stress). For example, FIG. 41 shows the effect of use of a nutritional supplement containing fish oil and selenium, chemotherapeutic agents Taxol or Adriamycin, and these chemotherapeutic agents in combination with the nutritional supplement on levels of malondialdehyde (MDA) in tumors of mice injected with breast cancer cells. As shown, use of the nutritional supplement (either alone or on combination with a chemotherapeutic drug) is effective in increasing the relative concentration of MDA, indicating an enhancement of oxidative stress in the tumor. Similar effects are seen in Avastin (see FIG. 42). A synergistic effect (for example, when the nutritional supplement is used in combination with Adriamycin) is also found. This is consistent with the results found for HIF-α, which is a marker for hypoxia, as shown in FIG. 32. It should be appreciated that such effects are complementary to the reduction in neovascularization described above and shown in FIGS. 24 and 25.

Sphere/Stem Cell Characteristics

The Inventor has also found that a nutritional supplement containing fish oil and selenium in combination with chemotherapeutic drugs can be effective in reducing stem cell characteristics of cancer cells. Development of cancer cells showing such characteristics is thought to be involved in both metastasis and in the development of resistance to chemotherapeutic drugs. It should be appreciated that sphere cells that form in cell culture are thought to replicate, at least in part, the development of cancer stem cells in vivo.

Figure 43:
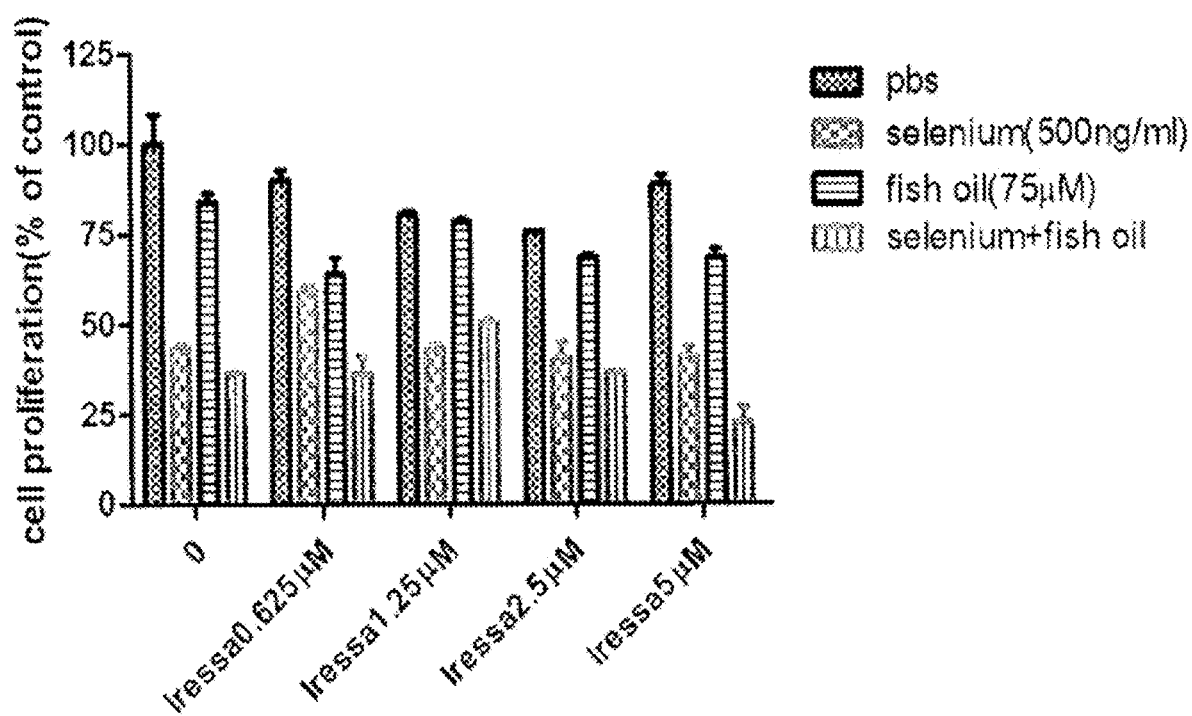
FIG. 43: Histogram of the effect of treatment with Iressa (0.625 µM to 5 µM) in combination with PBS or various supplements on proliferation of A549 tumor sphere (i.e. stem) cells.
Figure 44:
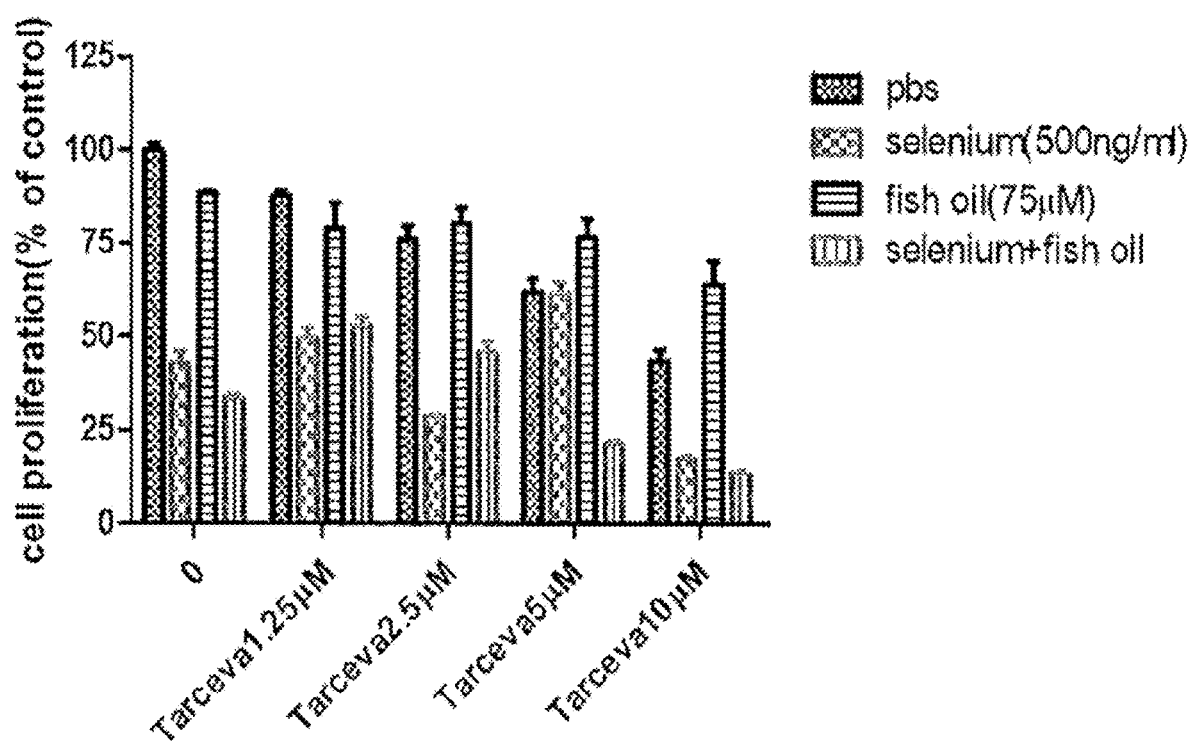
FIG. 44: Histogram of the effect of treatment with Tarceva (1.25 µM to 10 µM) in combination with PBS or various supplements on proliferation of A549 tumor sphere (i.e. stem) cells.

As shown in FIG. 43, A549 sphere cells are relatively resistant to treatment with Iressa, but show decreased proliferation in the presence of a supplement containing fish oil and selenium. When Iressa and the supplement are used in combination the effect is enhanced, and can be synergistic (for example, at higher Iressa concentrations). A549 lung cancer sphere cells are similarly resistant to Tarceva, with a synergistic reduction in proliferation being observed when the cells are treated with a combination of Tarceva (for example, at 10 μM) and a supplement containing fish oil and selenium (see FIG. 44).

Figure 45:
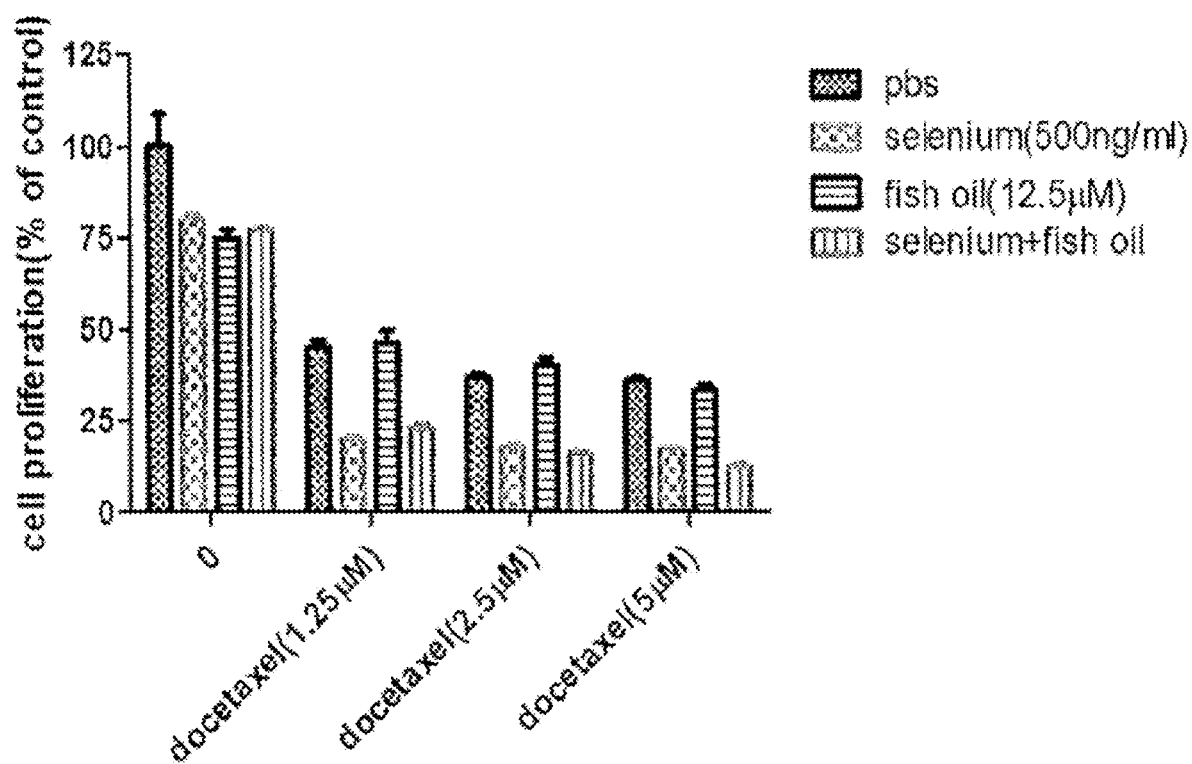
FIG. 45: Histogram of the effect of treatment with Docetaxel (1.25 µM to 5 µM) in combination with PBS or various supplements on proliferation of MDA-MB-231 tumor sphere (i.e. stem) cells.
Figure 46:
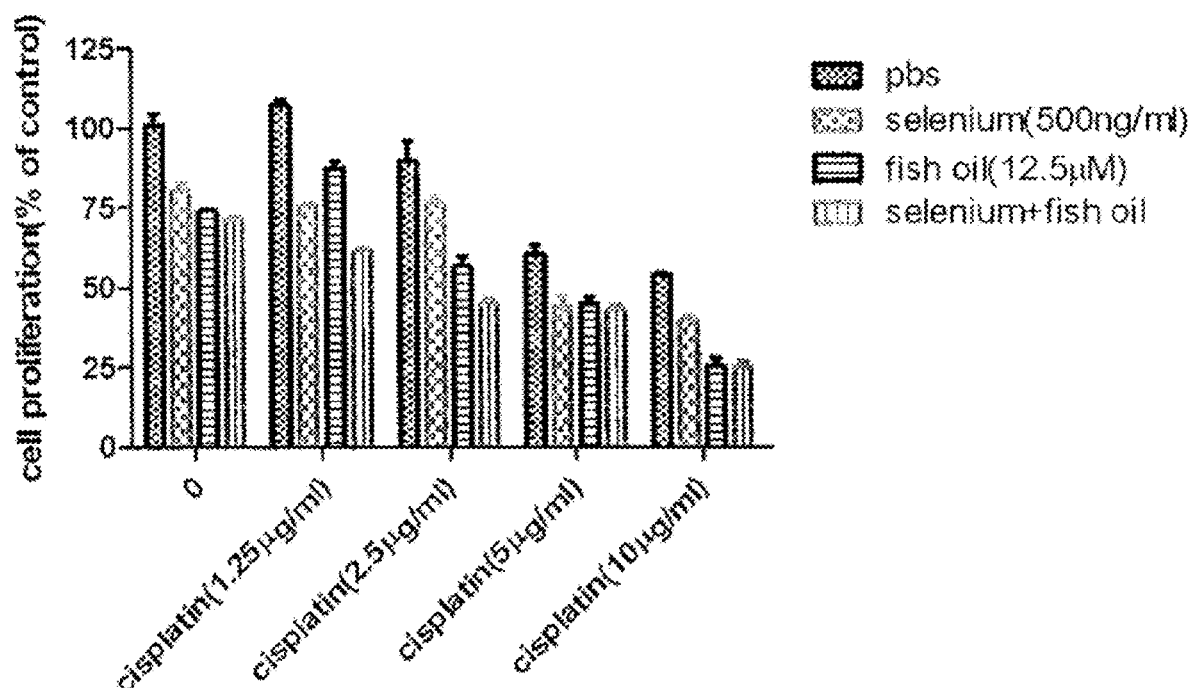
FIG. 46: Histogram of the effect of treatment with Cisplatin (1.25 µg/mL to 10 µg/mL) in combination with PBS or various supplements on proliferation of MDA-MB-231 tumor sphere (i.e. stem) cells.

A similar effect is observed in MDA-MB-231 breast cancer sphere cells. As shown in FIG. 45, these cells show a small drop in proliferation when exposed to a supplement containing fish oil and selenium, and show moderate sensitivity to Docetaxel, whereas a synergistic effect leading to a large decrease in proliferation is found when Docetaxel and the supplement are used in combination. MDA-MB-231 breast cancer sphere cells are relatively resistant to both Cisplatin and a supplement containing fish oil and selenium, however a large decrease in proliferation is found when Cisplatin and such a supplement are used in combination (see FIG. 46).

The effects of Cisplatin, selenium, fish oil, selenium and fish oil in combination, and Cisplatin with the combined supplement on cell cycle phase distribution are shown in 8FIG. 3C. As shown selenium and fish oil alone provide a very modest shift towards sub-G1, whereas selenium and fish oil in combination provide a relatively large shift. Cisplatin alone provides a modest shift toward sub-G1, which is enhanced when used in combination with a supplement containing fish oil and selenium. Results are tabulated in Table 4.

TABLE 4

|  | SubG1 | G0/G1 | S | G2/M |
| --- | --- | --- | --- | --- |
| Control | 5.2% | 67.4% | 9.8% | 22.8% |
| Selenium 500 ng/mL | 12.3% | 60.3% | 13.9% | 25.7% |
| Fish oil 75 μM | 13.6% | 66.3% | 14.3% | 19.4% |
| Fish oil 75 μM Selenium 500 ng/mL | 39.1% | 57.9% | 28.9% | 13.1% |
| Cisplatin 5 μg/mL | 11.7% | 48.5% | 45.4% | 6.1% |
| Cisplatin 5 μg/mL + Fish oil 75 μM Selenium 500 ng/mL | 14.2% | 30.9% | 52.7% | 16.4% |

Figure 47:
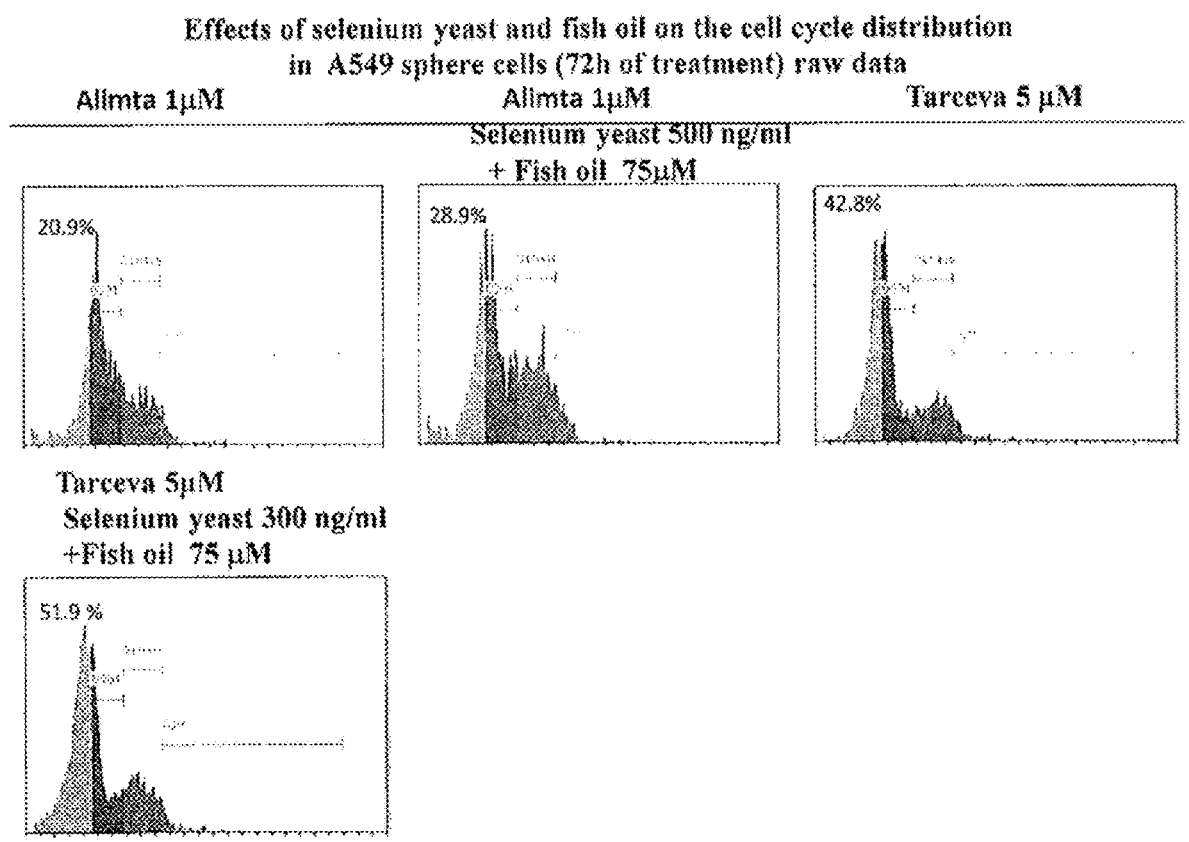
FIG. 47: Distribution of cell cycle phases of A549 tumor sphere cells (i.e. stem cells) treated with a chemotherapeutic agent (Alimta, 1 µM or Tarceva, 5 µM) and a nutritional supplement containing fish oil and selenium.

The concentration of fish oil represents its DHA content
Each gram of fish oil contains 220 mg DHA and 330 mg EPA Similar results are found for A549 lung cancer sphere cells treated with Alimta, Tarceva, and these chemotherapeutic agents in combination with a supplement containing fish oil and selenium, as shown in FIG. 47. Results from these studies are summarized in Table 5.

TABLE 5

|  | SubG1 | G0/G1 | S | G2/M |
| --- | --- | --- | --- | --- |
| Alimta 1 μM | 20.9% | 62.4% | 30.4% | 7.2% |
| Alimta 1 μM + Fish oil 75 μM Selenium 300 ng/mL | 28.9% | 50.1% | 40.4% | 9.6% |

TABLE 5-continued

|  | SubG1 | G0/G1 | S | G2/M |
| --- | --- | --- | --- | --- |
| Tarceva 5 μM | 42.8% | 58.3% | 32.7% | 8.9% |
| Tarceva 5 μM + Fish oil 75 μM Selenium 300 ng/mL | 51.9% | 50.7% | 41.2% | 8.1% |

It should be appreciated that sub-G1 is associated with apoptosis. As such, the Inventor believes that use of a combination of a supplement containing fish oil and selenium in combination with a chemotherapeutic agent can be effective in inducing apoptosis in cancer sphere or stem cells, even when such cells are resistant to the chemotherapeutic agent.

Figure 48:
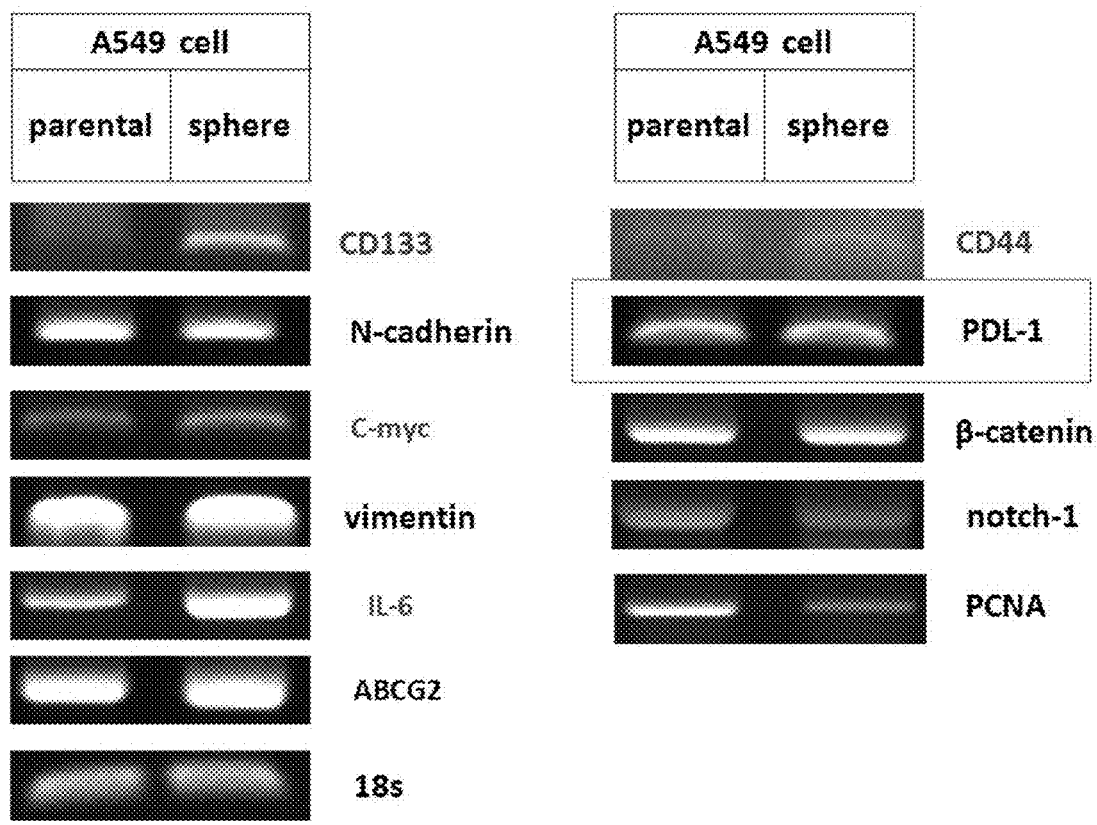
FIG. 48: Western blots showing expression of various proteins in parental and sphere (i.e. stem) A549 cells.
Figure 49:
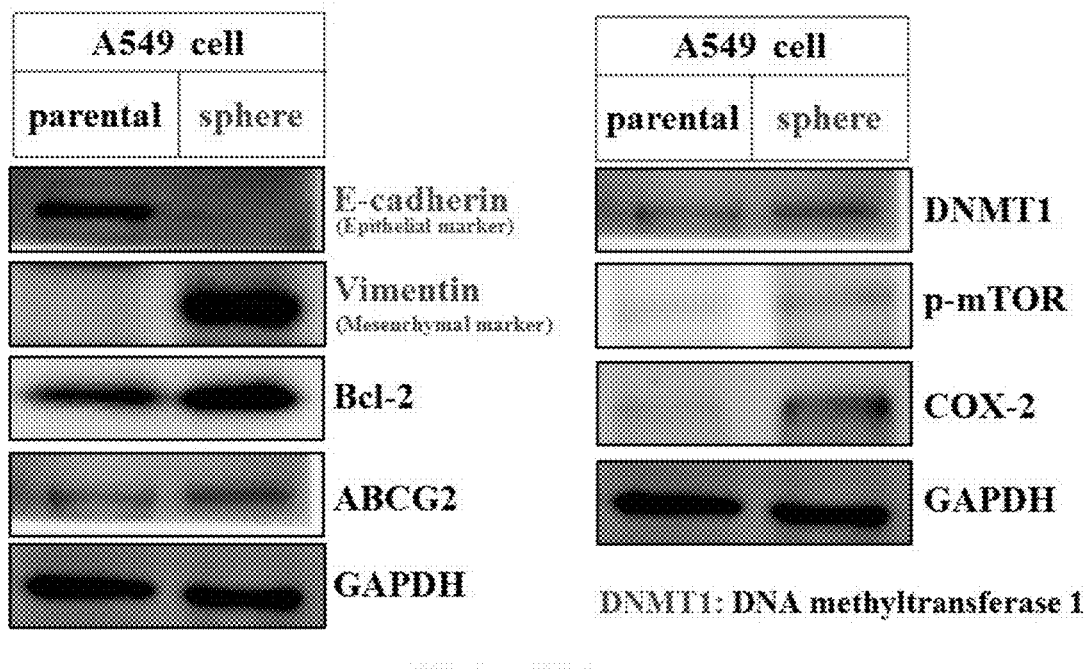
FIG. 49: Western blots showing elevated expression of stem-cell related proteins in A549 sphere (i.e. stem) cells.

The Inventor has also found that the use of a supplement containing fish oil and selenium in combination with a chemotherapeutic agent can modify expression of biochemical markers associate with cancer sphere or stem cells, bringing them into accordance with levels associated with non-stem cancer cells. As shown in FIG. 48, expression of various biochemical markers (notably CD133, C-myc, IL-6, and CD44) differs between parental A549 lung cancer cells and sphere cells derived from the same cell line. FIG. 49 shows expression levels of markers associated with stem cells (i.e. associated with "stemness") in such A549 sphere cells, notably E-cadherin (an epithelial marker) and Vimentin (a mesenchymal marker), relative to parental A549 cells.

Figure 50:
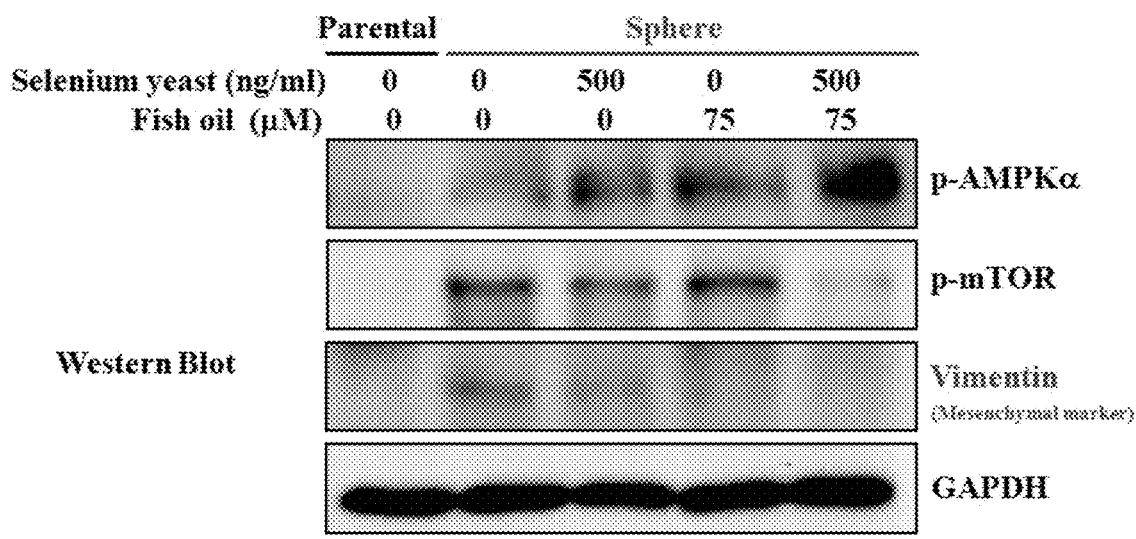
FIG. 50: Western blots showing a reduction of stem cell characteristics in A549 sphere (i.e. stem) cells treated with a nutritional supplement containing fish oil and selenium.
Figure 51:
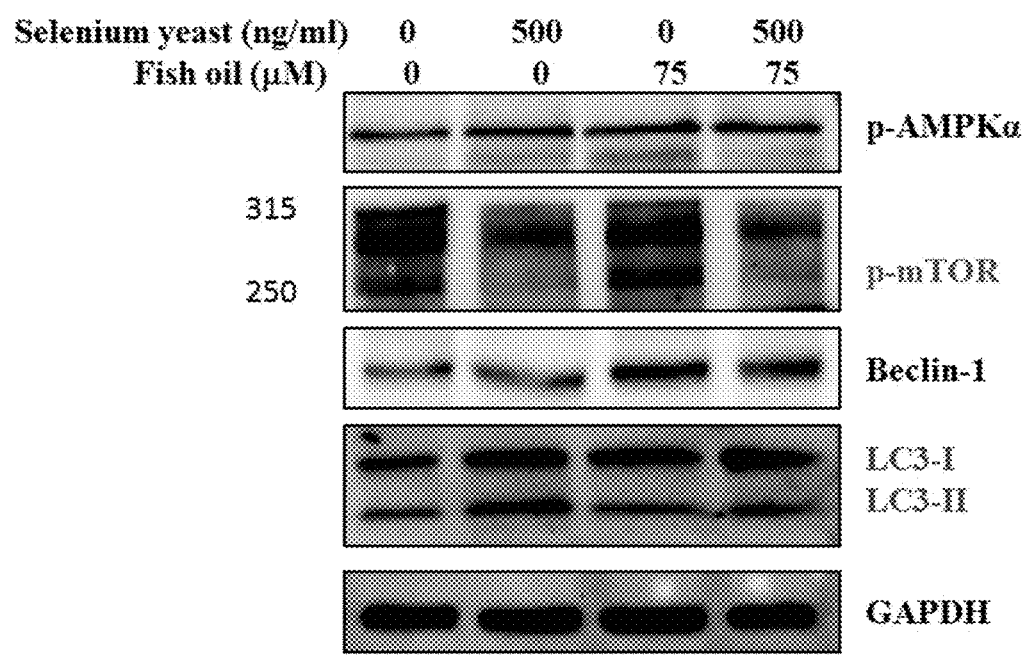
FIG. 51: Western blots showing a reduction of stem cell characteristics in A549 sphere (i.e. stem) cells treated with a nutritional supplement containing fish oil and selenium.
Figure 52:
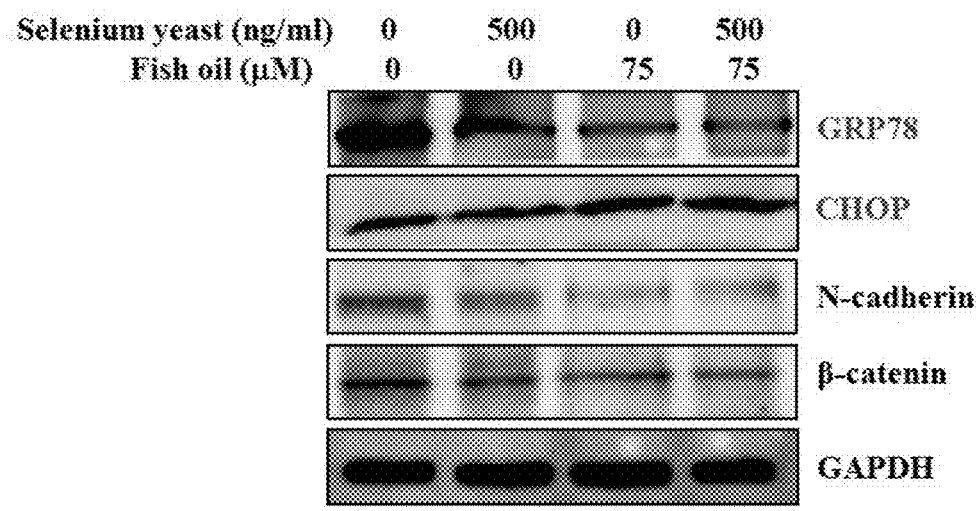
FIG. 52: Western blots showing a reduction of stem cell characteristics in A549 sphere (i.e. stem) cells treated with a nutritional supplement containing fish oil and selenium.

As shown in FIG. 50 the use of a supplement containing fish oil and selenium modifies levels of various biochemical markers in A549 sphere cells, notably p-AMPKα, p-mTOR, and Vimentin. It should be appreciated that p-mTOR and Vimentin are elevated in A549 sphere cells, and reduced to levels similar to those of the parental A549 cells on exposure to a supplement containing both fish oil and selenium, indicating a reduction in stem cell characteristics. Results of a similar study performed on A549 sphere cells are shown in FIG. 51, which shows an increase in LC3-I and LC3II on exposure to a supplement containing both fish oil and selenium. Similar studies show a reduction in GRP78, N-cadherin, and P-catenin (see FIG. 52).

Figure 53:
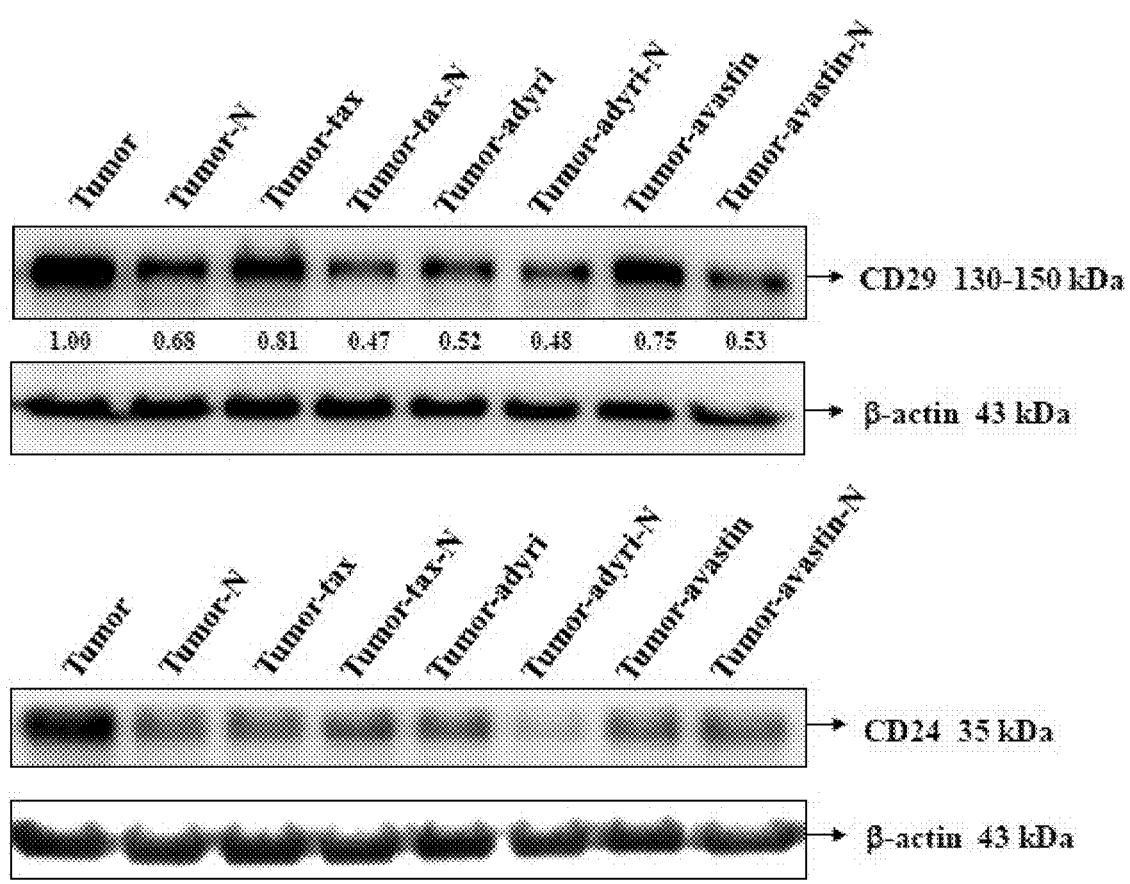
FIG. 53: Western blots showing the effect of a nutritional supplement containing fish oil and selenium in combination with chemotherapeutic agents on cancer stem cell markers in an in vivo model of breast cancer. Actin is included as a control.

While the above studies focused on A549 sphere cells, similar results were obtained from in vivo studies of animal models of human breast cancer. FIG. 53 shows the results of studies characterizing expression of CD29 and CD24 in tumors of animals treated with a nutritional supplement containing fish oil and selenium ("N"), Taxol, Adriamycin, Avastin, and these chemotherapeutic agents in combination with the nutritional supplement. As shown, treatment with a nutritional supplement containing fish oil and selenium produces a moderate reduction in CD29 expression, whereas treatment with the chemotherapeutic drugs has very little effect. Combined therapy, however, was found to strongly reduce CD29 levels, indicating that such combinations provide a synergistic effect in reducing stem cell characteristics of tumors in vivo. Expression of CD24 is more responsive to treatment with the nutritional supplement containing fish oil and selenium, however synergistic effects in reducing CD24 levels when used in combination with chemotherapeutic agents (notably Avastin) are apparent.

Overall, the Inventor has found that use of a nutritional supplement that includes fish oil and selenium can reduce stem cell characteristics and/or "stemness" in cancer cells, and can do so in a synergistic manner when used in combination with chemotherapeutic drugs.

Reversal of Drug Resistance

Figure 54:
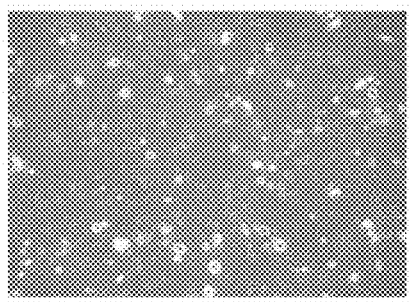
FIG. 54: Photomicrographs of Iressa-resistant cancer cells treated with a nutritional supplement containing fish oil and selenium and/or Iressa.
Figure 54:
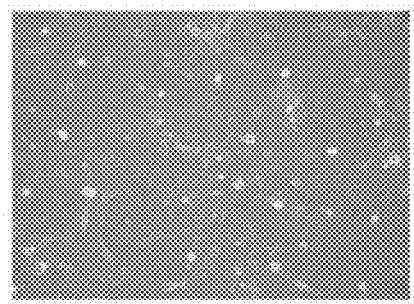
Figure 54:
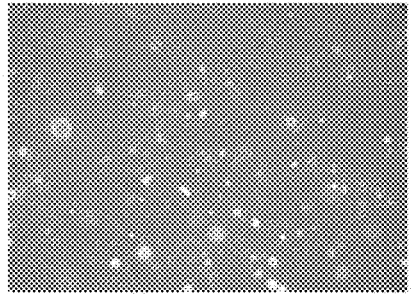
Figure 54:
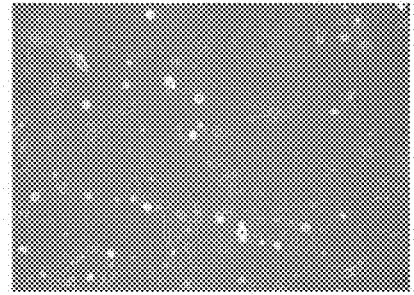

As noted above, development of stem cell characteristics (e.g. "stemness") in cancer cells has been associated with the development of drug resistance. Surprisingly, the Inventor has found that a nutritional supplement that includes fish oil and selenium is effective in sensitizing drug-resistant cancer cells to chemotherapeutic drugs to which they have demonstrated resistance. For example, HCC827Gr cells are human lung cancer-derived cells that have developed resistance to chemotherapeutic agents, such as Iressa. The result of exposure of such cells in culture to Iressa in the presence and absence of a selenium+fish oil supplement are shown in FIG. 54. As shown in FIG. 54, exposure to Iressa does not significantly decrease the number of viable resistant HCC827Gr cells, however a significant reduction in the number of viable cells is found when Iressa is used in combination with a selenium+fish oil supplement.

Figure 55:
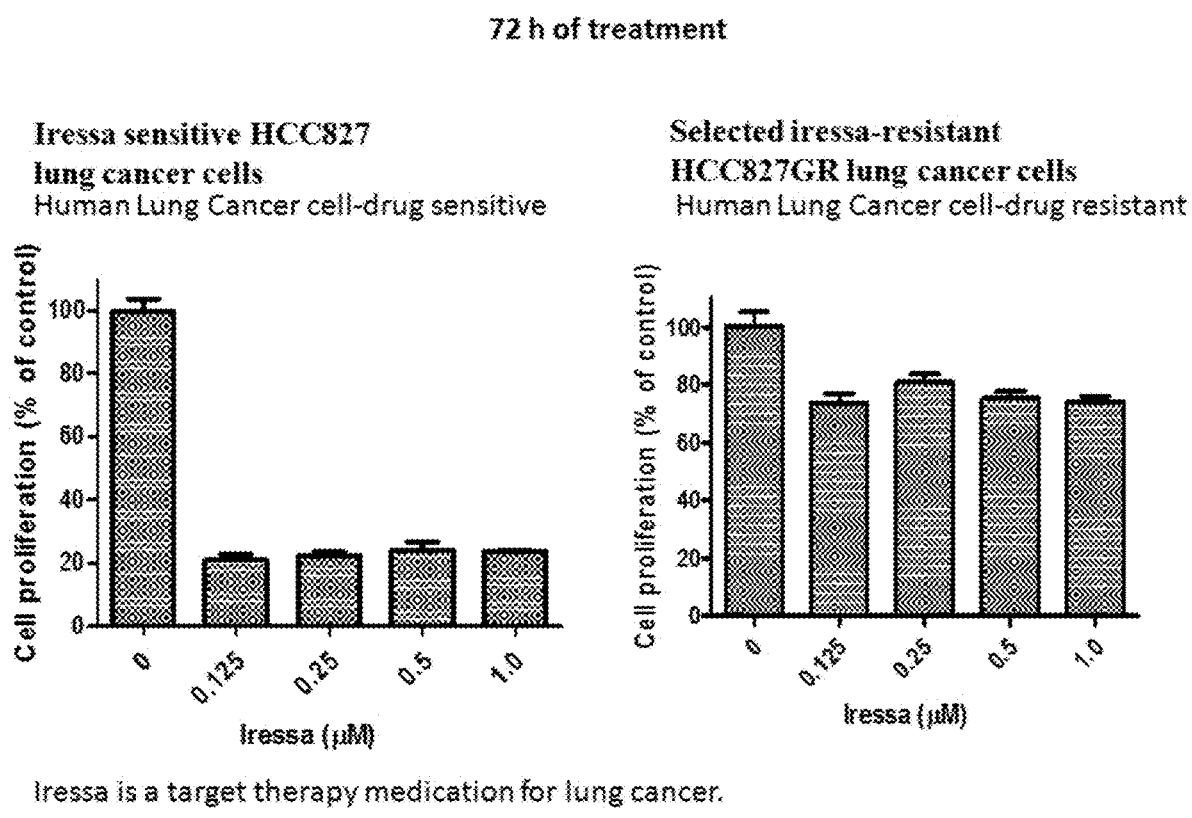
FIG. 55: Histograms of the response of HCC827 and resistant HCC827Gr cell lines to Iressa.
Figure 56:
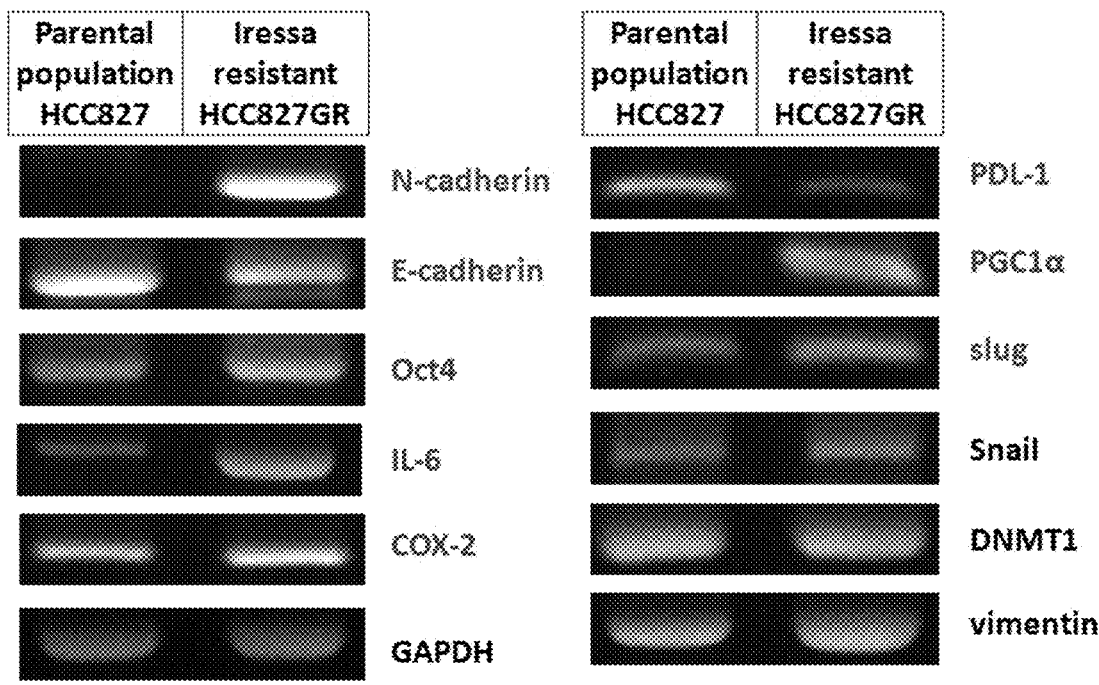
FIG. 56: Western blots showing differences in expression of various markers between HCC827 and resistant HCC287Gr cells. The resistant HCC287Gr cells show stem cell characteristics.
Figure 56:
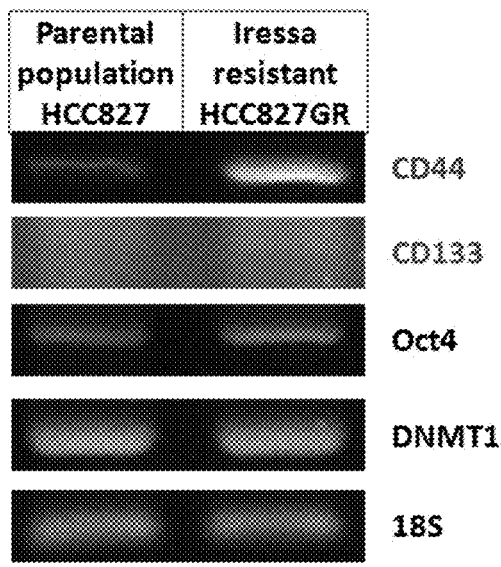

This sensitization effect is also found when cell proliferation is characterized. As shown in FIG. 55 a parental HCC827 lung cancer cell line (left panel) is sensitive to Iressa, with proliferation reduced by over 80% at 0.125 μM Iressa. In contrast, drug resistant HCC827Gr lung cancer cells (right panel) continue to proliferate at almost 80% of control values even in the presence of 1 μM Iressa. Differences between the drug sensitive parental cell line and the drug resistant cell line are also evident in the expression of several biochemical markers. As shown in FIG. 56, differences in gene expression (shown as mRNA) for a variety of stem cell, metabolic, and epithelial-mescenchymal transition (EMT) genes are apparent between susceptible parental HCC827 cells and resistant HCC287Gr cells.

Figure 57:
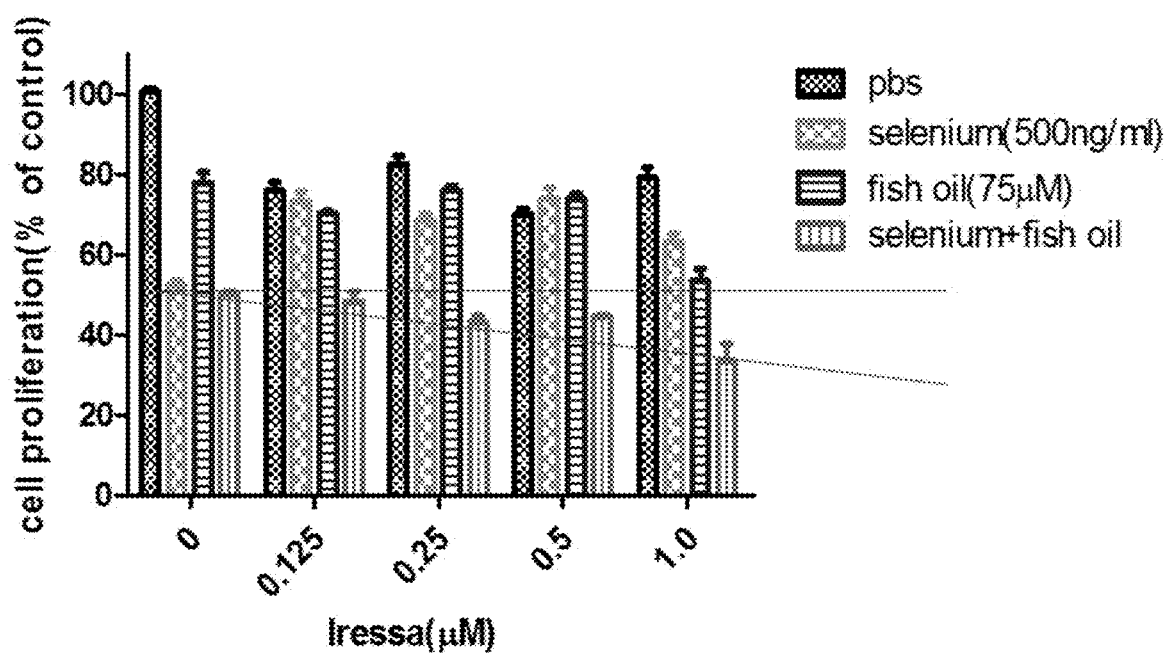
FIG. 57: Histogram showing sensitization of resistant HCC827Gr cells to up to 1 µM Iressa on cotreatment with a nutritional supplement containing fish oil and selenium.
Figure 58:
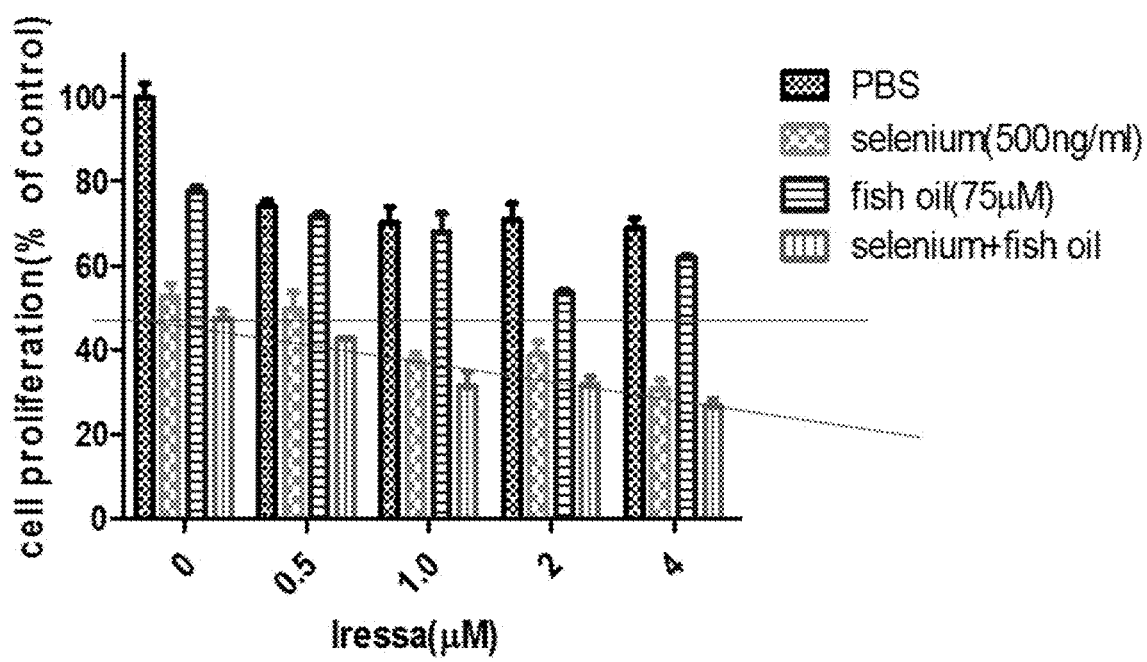
FIG. 58: Histogram showing sensitization of resistant HCC827Gr cells to up to 4 µM Iressa on cotreatment with a nutritional supplement containing fish oil and selenium.

FIG. 57 and FIG. 58 show the effects of cotreatment of resistant HCC827Gr cells with Iressa with a selenium, fish oil, or selenium and fish oil containing supplement. As shown, in the absence of supplementation Iressa produces, at most, only a 20% reduction in cell proliferation. Treatment with a supplement containing both fish oil and selenium results in a modest reduction in proliferation (about 50%). Treatment with a supplement containing both selenium and fish oil, however, reduces cell proliferation to levels similar to those seen with the sensitive HCC827 parental cell line (i.e. approximately 20% of untreated control). It is apparent that use of a supplement containing fish oil and selenium is effective in sensitizing drug-resistant cancer cells to chemotherapeutic drugs, including drugs to which they have demonstrated resistance.

Figure 59:
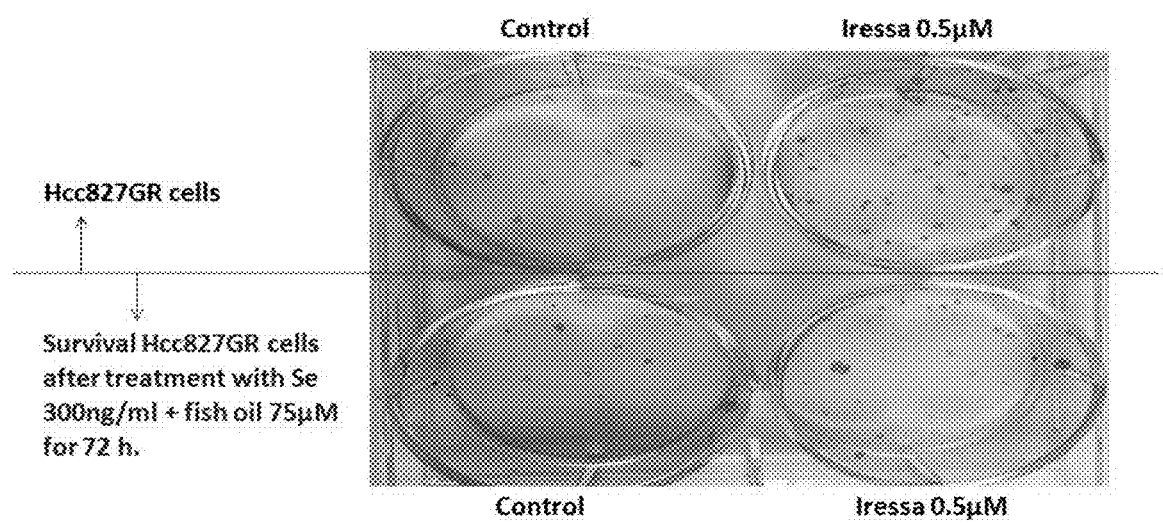
FIG. 59: Inhibition of colony formation by resistant HCC827Gr cells by treatment with Iressa in combination with a nutritional supplement containing fish oil and selenium.
Figure 60:
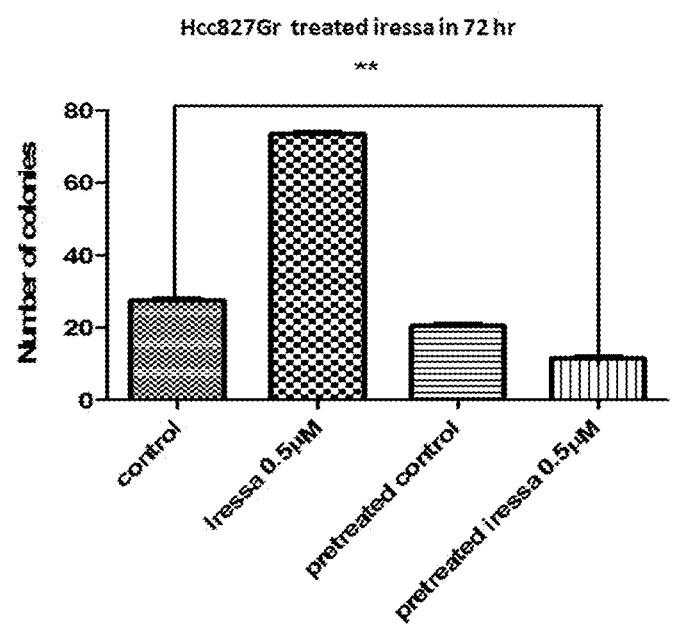
FIG. 60: Histogram showing inhibition of colony formation by resistant HCC827Gr cells by treatment with Iressa in combination with a nutritional supplement containing fish oil and selenium.

As shown in FIG. 59 and FIG. 60, similar sensitization in regards to reducing colony formation is found on treatment with a supplement that includes selenium and fish oil. Significant colony formation by HCC827Gr cells is found in the presence of 0.5 μM Iressa, but is greatly reduced in cells treated with a combination of selenium and fish oil. The synergistic effect between Iressa (which does not prevent an increase colony formation by resistant HCC827Gr cells) and the selenium+fish oil supplement in suppressing colony formation by these resistant cancer cells is apparent, as colony formation is reduced to below that of cells treated with the selenium+fish oil supplement alone.

Figure 61:
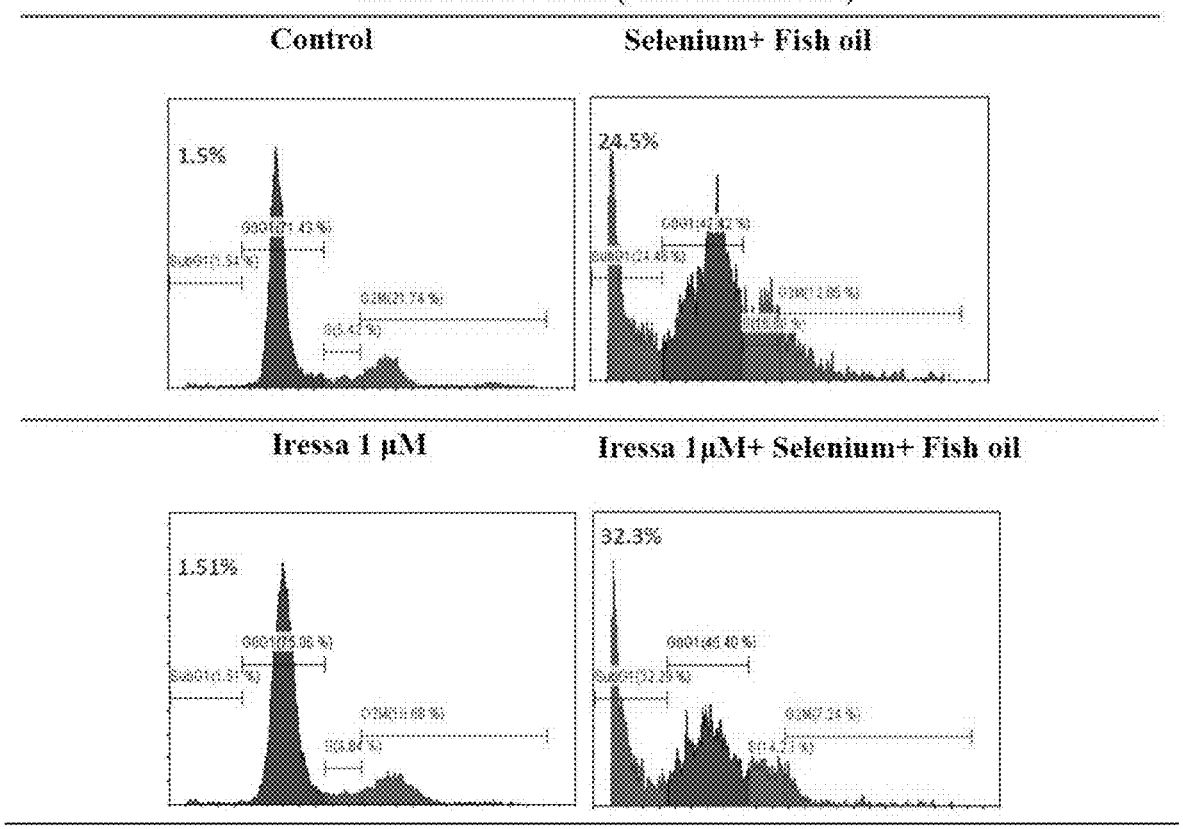
FIG. 61: Frequency distribution of cell cycle phases on treatment of Iressa-resistant HCC827GR cells with Iressa, a nutritional supplement containing fish oil and selenium, and combined treatment.

The Inventor has also found that treatment of such resistant cancer cells with fish oil and selenium yeast modifies the cell cycle phase distribution of these cells, as shown in FIG. 61. Numerical results are summarized in Table 6. As shown, treatment with Iressa alone has little to no effect on the cell cycle phase distribution of resistant HCC827GR cells. Treatment of such cells with a combination of fish oil and selenium yeast, however, shifts the cell cycle distribution strongly towards S and SubG1 phases. Similar results are seen with co-treatment using Iressa and the nutritional supplement, with a significant increase in the percentage of cells in SubG1 and a concomitant decrease in cells in G2/M phase. This indicates that a nutritional supplement containing fish oil and selenium yeast has an unexpected synergistic effect on cell cycle distribution in such chemotherapy-resistant cells.

TABLE 6

|  | SubG1 | G0/G1 | S | G2/M |
| --- | --- | --- | --- | --- |
| Control | 1.5% | 72.45% | 5.49% | 22.05% |
| Selenium + Fish oil | 24.5% | 62.6% | 20.5% | 16.9% |
| Iressa 1 μM | 1.51% | 76.1% | 4.9% | 18.9% |
| Iressa 1 μM + Selenium + Fish oil | 32.3% | 68.4% | 20.9% | 10.7% |

Inventors have found, surprisingly, that pre-treatment of chemotherapy resistant cells (such as HCC827GR) with a nutritional supplement containing fish oil and selenium yeast can have the effect of sensitizing these resistant cells to subsequent exposure to a chemotherapeutic agent to which they have demonstrated resistance. FIG. 4 shows the results of pre-treatment of Iressa-resistant HCC827GR cells with a nutritional supplement containing fish oil and selenium for 72 hours prior to exposure of the cells to Iressa. As shown, such pre-treated cells show a significant decrease in cell proliferation relative to cells pre-treated with PBS.

Figure 62:
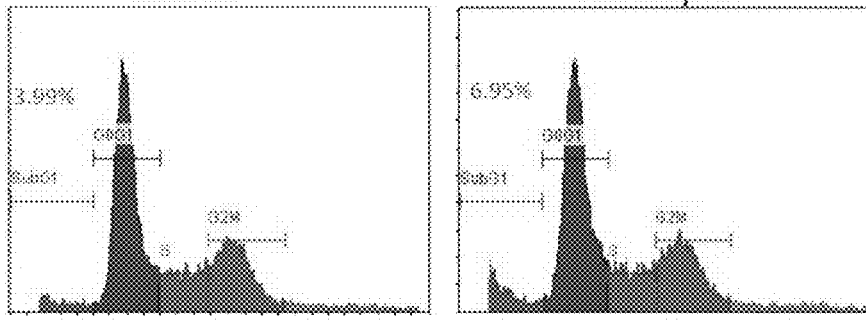
FIG. 62: Frequency distribution of cell cycle phases following pre-treatment with a nutritional supplement of the inventive concept, with and without the addition of Iressa, in Iressa-resistant HCC827GR cells.
Figure 62:
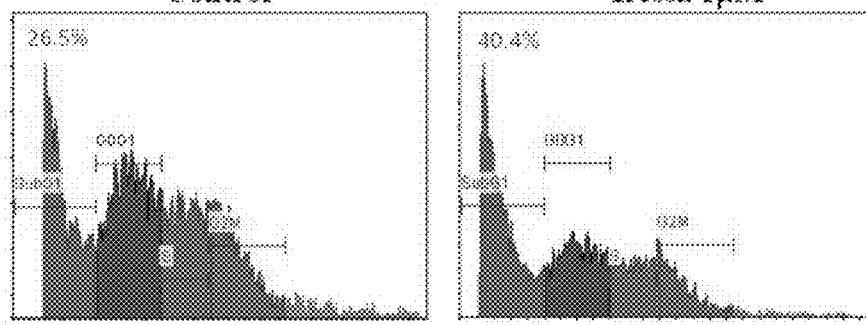

As shown in FIG. 62, such pre-treatment with a nutritional supplement containing fish oil and selenium yeast also impacts cell cycle phase distribution relative to untreated cells. Numerical results of such a study are summarized in Table 7.

Pretreated with Selenium and Fish Oil for 72 h

TABLE 7

| 72 h-pretreatment |  | SubG1 | G0/G1 | S | G2/M |
| --- | --- | --- | --- | --- | --- |
| None | Control | 3.99% | 55.7% | 16.6% | 27.7% |
| None | Iressa 1 μM | 6.95% | 56.5% | 16.2% | 27.3% |
| Selenium + Fish oil | Control | 26.5% | 46.2% | 28.6% | 25.2% |
| Selenium + Fish oil | Iressa 1 μM | 40.4% | 47.3% | 29.2% | 23.5% |

As shown, pre-treatment with a nutritional supplement containing fish oil and selenium yeast alters the cell cycle phase distribution of these Iressa-resistant cells towards a significantly higher proportion of SubG1 and S phase cells. Application of Iressa to such pre-treated cells provides a still higher percentage of cells in Sub-G1 phase. It should be appreciated that the sub-G1 phase is associated with apoptosis.

Reduction in Progression/Metastasis

Figure 63:
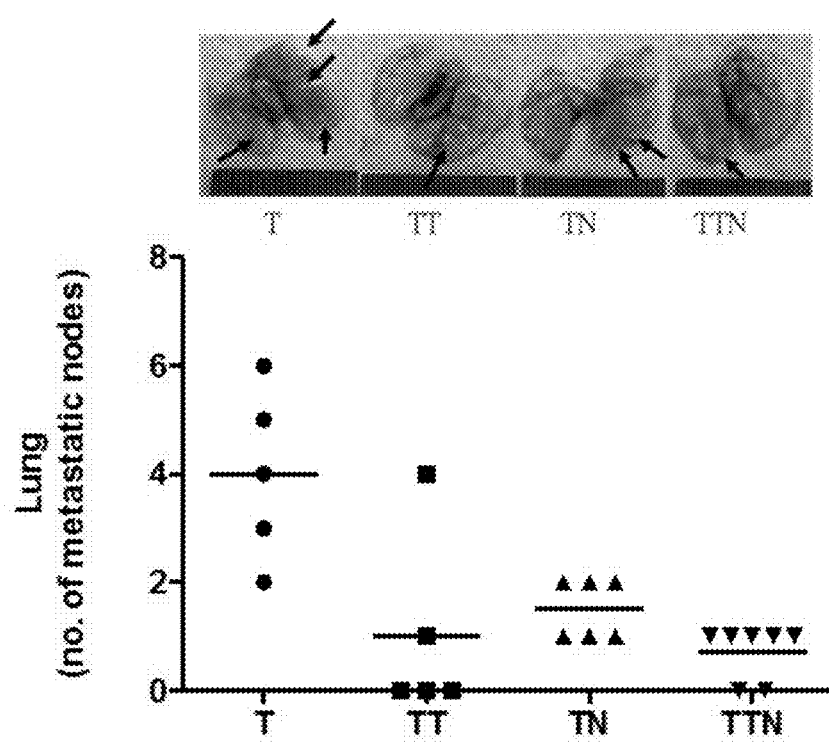
FIG. 63: Frequency of lung cancer metastasis in animal models treated with a nutritional supplement containing fish oil and selenium and/or a chemotherapeutic agent.

The Inventor has found that a supplement containing fish oil and selenium can effectively reduce tumor metastasis and/or progression, particularly when used in combination with a chemotherapeutic agent. For example, Inventors have found that use of a nutritional supplement containing fish oil and selenium in combination with a chemotherapeutic agent can reduce metastasis from a primary tumor site. As shown in FIG. 63, untreated mice show extensive metastasis of tumor cells from the implantation site of lung cancer cells. Metastatic sites are indicated by arrows in the upper panel of FIG. 63, whereas findings are enumerated in the lower panel. This is reduced to some extent by treatment with Tarceva ("TT") or the supplement containing fish oil and selenium ("TN"), however the degree of lymph node metastasis is most pronounced using a combination of the two ("TTN").

Figure 64:
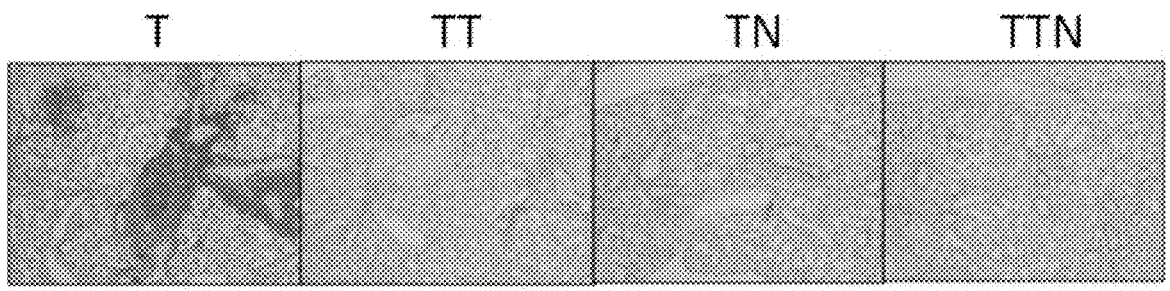
FIG. 64: Photomicrographs showing the results of immunohistochemical staining for cells bearing tumor markers in implanted mice treated with Tarceva, a nutritional supplement containing fish oil and selenium, and a combination of Tarceva and the supplement.
Figure 64:
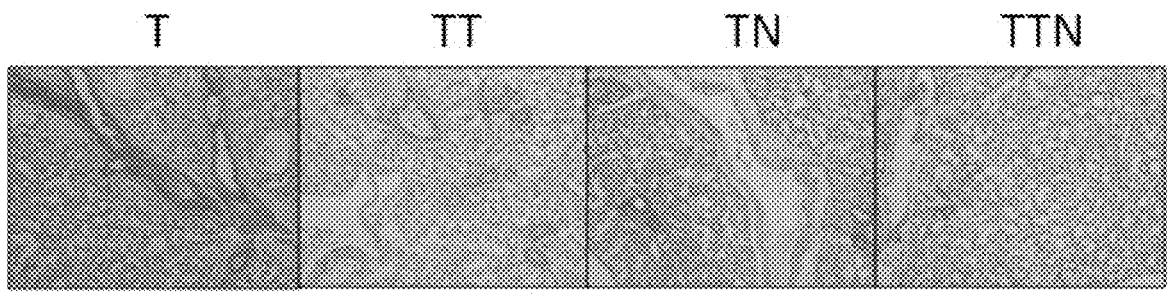
Figure 65:
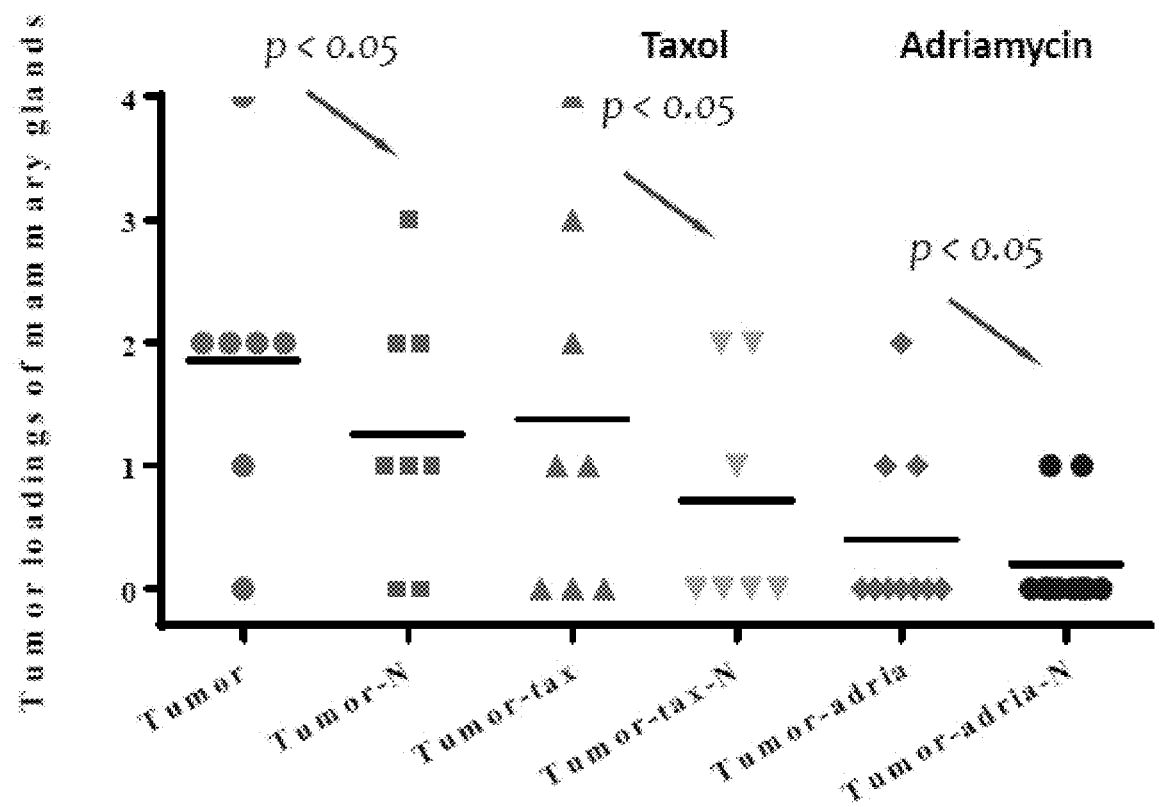
FIG. 65: Graph of the effect of a nutritional supplement containing fish oil and selenium on metastatic tumor load when used in combination Taxol or Adriamycin in an in vivo breast cancer model.

Without wishing to be bound by theory, the Inventors believe that this may be due to sensitization of cancer stem cells to the effects of Tarceva by the supplement containing fish oil and selenium, and/or by a reduction in stem cell characteristics that facilitate metastasis. This reduction in metastasis can also be seen on a microscopic level in the reduction in the number of cells identified by immunohistochemistry as expressing EGFR and VEGF, which is characteristic of the implanted tumor cells. As shown in FIG. 64, there is a dramatic reduction in the number of such cells identified in lung tissue sections taken from mice treated with both a supplement containing fish oil and selenium and a chemotherapeutic agent. Similar results were observed for the use of a nutritional supplement containing fish oil and selenium in reducing metastatic tumor load in the mammary glands of the test animals implanted with breast cancer cells, as shown in FIG. 65. As shown, use of the nutritional supplement containing fish oil and selenium (N) or Taxol provided a modest reduction in tumor loading of mammary glands, while a dramatic reduction is found when Taxol and the supplement are used in combination. Adriamycin was found to be more effective than Taxol in reducing metastatic tumor load, however cotherapy with a nutritional supplement containing fish oil and selenium provided an even greater reduction in metastasis.

Figure 66:
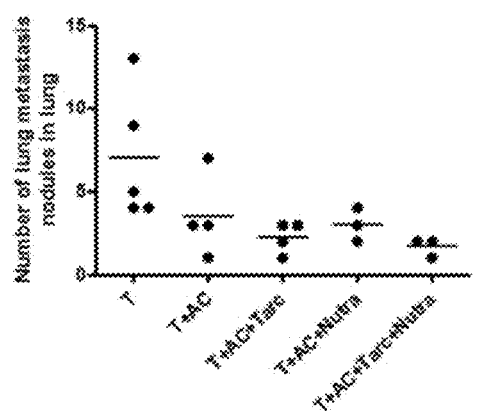
FIG. 66: Frequency of metastasis in tumor-bearing mice treated with a nutritional supplement containing fish oil and selenium and/or multiple chemotherapy drugs.

A reduction in metastasis when a nutritional supplement containing fish oil and selenium was used in combination with multiple chemotherapeutic drug therapies was also found. Cotherapy with a nutritional supplement containing fish oil and selenium and chemotherapeutic drugs can also reduce the incidence of metastasis relative to the use of chemotherapeutic drugs alone. As shown in FIG. 66 lung metastasis occurred in all tumor-bearing mice that did not receive treatment, with liver metastasis occurring in 40% of such mice. This is reduced in tumor-bearing mice receiving combination chemotherapy with multiple drugs (AC=Adriamycin/Cisplatin, Tarc=Tarceva), however 80% of such mice still developed lung metastasis. Cotherapy with a nutritional supplement containing fish oil and selenium ("Nutra"), however, reduced the incidence of lung metastasis by 40% relative to untreated control mice.

Figure 67:
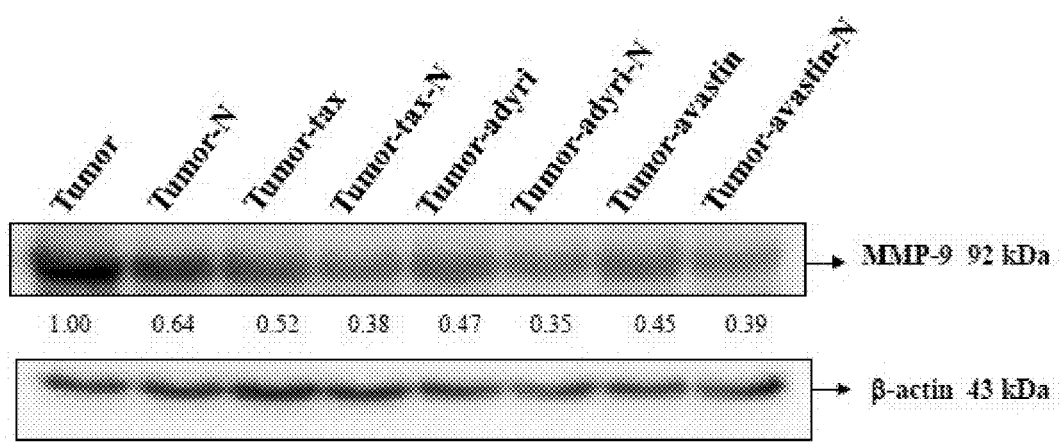
FIG. 67: Western blots showing the effect of a nutritional supplement containing fish oil and selenium in combination with chemotherapeutic agents on tumor expression of MMP-9 in an in vivo model of breast cancer. Actin is included as a control.

In addition to observation of a reduction in metastatic tumors and tumor cells, a reduction in biochemical markers associated with tumor metastasis and progression was also found on treatment with a nutritional supplement containing fish oil and selenium, which was potentiated by cotherapy with chemotherapeutic agents. As shown in FIG. 67, use of the nutritional supplement markedly reduced expression of MMP-9, a tumor associated protein associated with tumor progression in breast cancer cells. This is particularly found when used in combination with a chemotherapeutic agent (e.g. Taxol ("tax"), Adriamycin ("adyri"), Avastin). Loss of MMP-9 is associated with a reduction in tumor malignancy.

Figure 68:
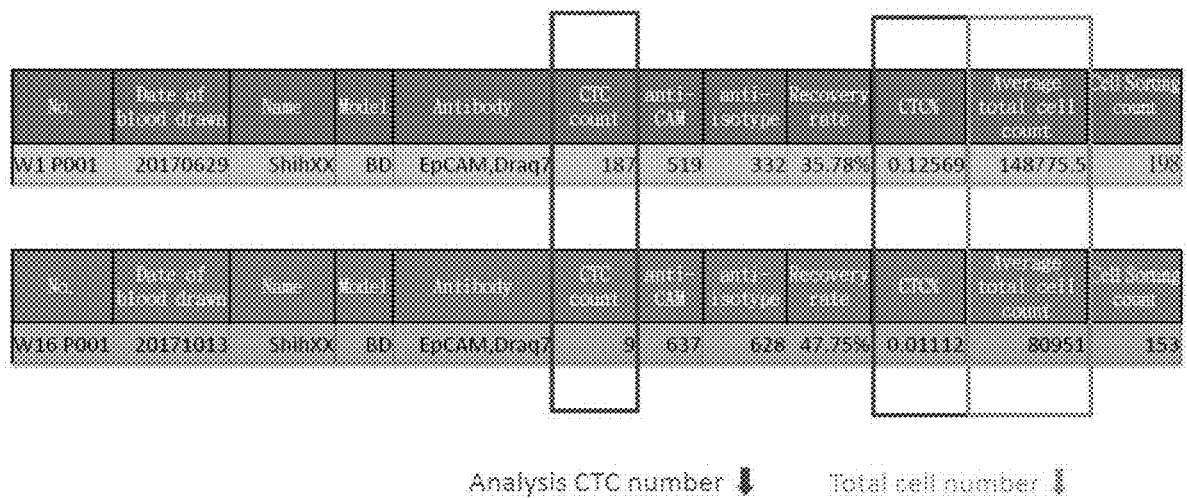
FIG. 68: Reduction in circulating tumor cells in a clinical patient treated with a nutritional supplement containing fish oil and selenium.

Surprisingly, the Inventor has also found that use of a nutritional supplement containing fish oil and selenium can reduce the number of circulating cancer cells in human patients. Data from a patient treated for 16 weeks with a nutritional supplement containing fish oil and selenium is shown in FIG. 68. The upper panel shows results from Week 1, with a circulating tumor cell "CTC" count of 187. The lower panel shows results from Week 16, with a CTC count of 9 (essentially background). The Inventor believes that treatment with a nutritional supplement containing fish oil and selenium can provide a dramatic reduction in circulating tumor cells, for example reducing apparent CTC counts to essentially background or normal levels (or less) thereby reducing the chances and/or extent of metastasis. The Inventor believes that this effect can be enhanced by cotherapy with one or more chemotherapeutic agents.

Immune Checkpoint/Immunotherapy

Figure 69:
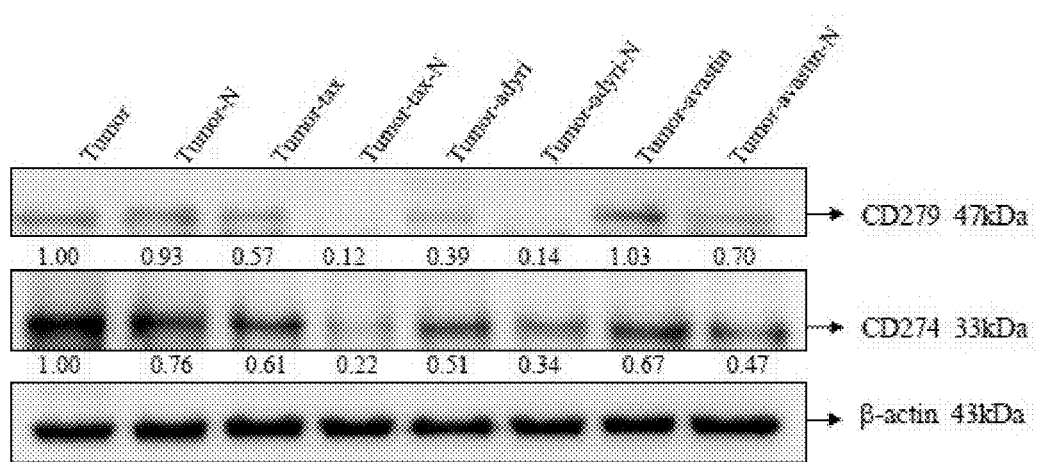
FIG. 69: Western blots showing the effect of a nutritional supplement containing fish oil and selenium in combination with chemotherapeutic agents on immune checkpoint proteins CD279 and CD274 in an in vivo model of breast cancer. Actin is included as a control.

While chemotherapeutic agents have long been used in treating cancer, more recently immunological approaches have been explored. Often such approaches are directed to the modulation of immune checkpoint molecules, providing activation of components of the immune system and/or inhibition of components that reduce immune response to tumor cells. Surprisingly, the Inventor has found that a nutritional supplement containing fish oil and selenium can modify the expression of such immune checkpoint molecules. For example, the Inventor has found that nutritional supplements containing fish oil and selenium are effective in reducing immune checkpoint proteins (e.g. CD279, CD274), and are also capable of doing so when used in combination with conventional chemotherapy drugs (e.g. Taxol ("tax"), Adriamycin ("adyri"), Avastin), as shown in FIG. 69.

Figure 70:
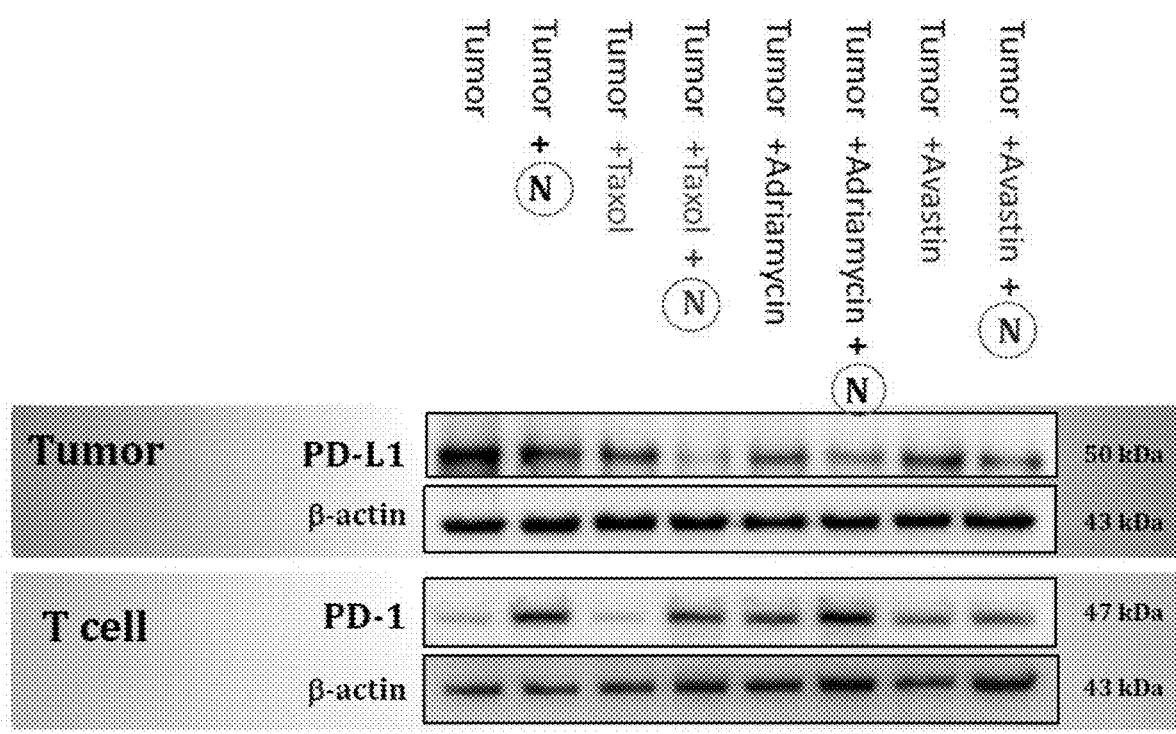
FIG. 70: Western blots showing the effect of a nutritional supplement containing fish oil and selenium in combination with chemotherapeutic agents on primary tumor PD-L1 and T cell PD-1 in an in vivo model of human cancer. Actin is included as a control.
Figure 71:
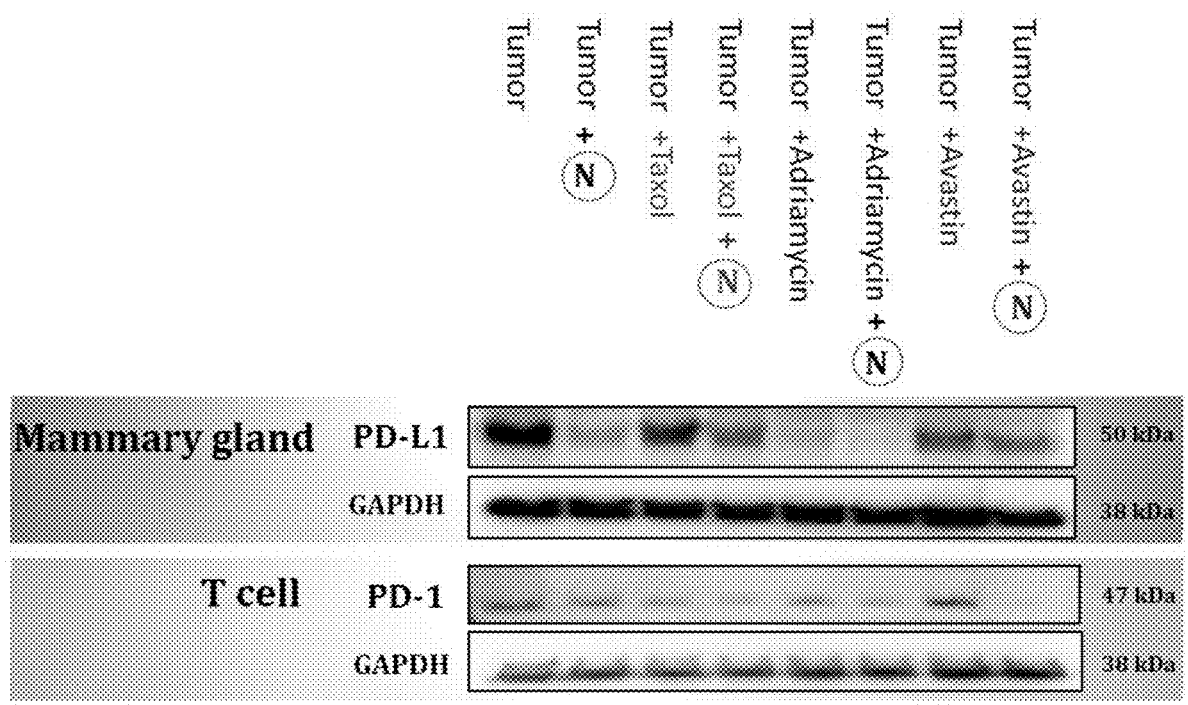
FIG. 71: Western blots showing the effect of a nutritional supplement containing fish oil and selenium in combination with chemotherapeutic agents on metastatic tumor (i.e. mammary gland) PD-L1 and T cell PD-1 in an in vivo model of metastasized human cancer. Actin is included as a control.
Figure 72:
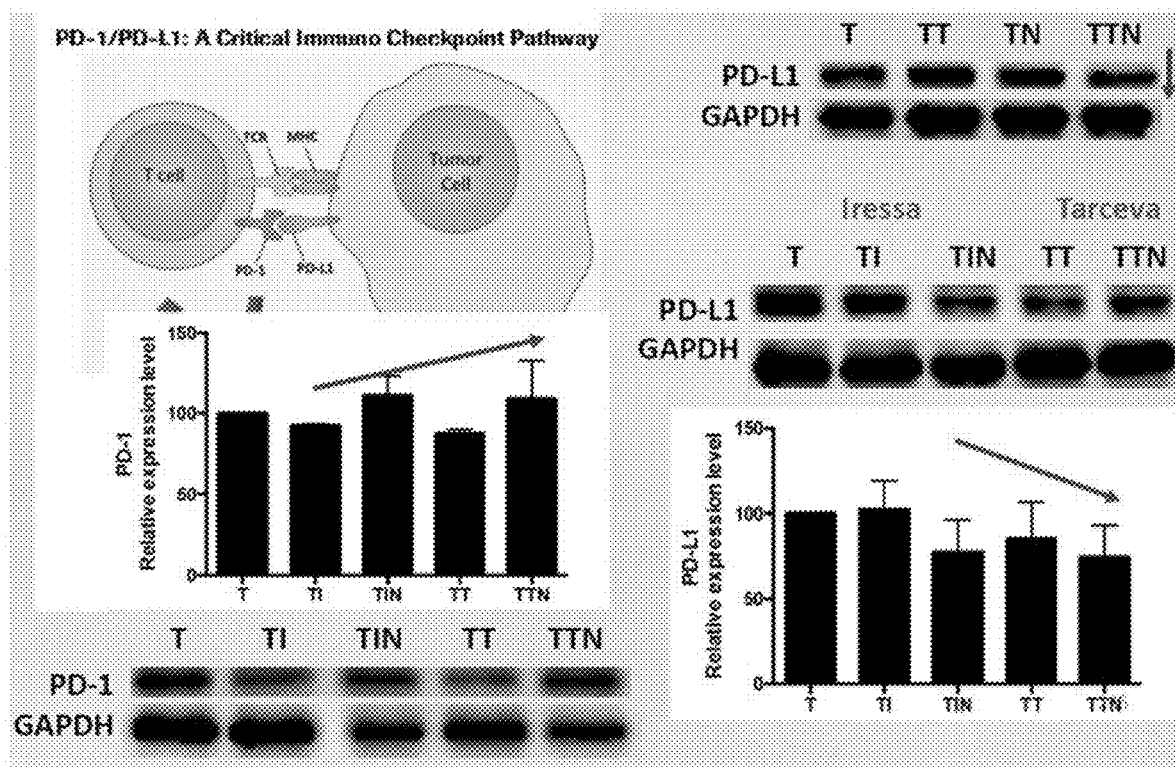
FIG. 72: Histograms and Western blots showing the effect of a nutritional supplement containing fish oil and selenium in combination with chemotherapeutic agents on tumor PD-L1 and T cell PD-1 in an in vivo model of human cancer. Actin is included as a control.

Modulation of PD-L1 in tumor cells and PD-1 in T cells in animal models treated with a nutritional supplement containing fish oil and selenium, either alone or in combination with various chemotherapeutic agents (Taxol, Adriamycin, Avastin) is shown for lung cancer cells in FIG. 70 and breast cancer in FIG. 71. As shown, tumor associated PD-L1 is reduced to some extent by treatment with the nutritional supplement and each of the chemotherapeutic agents, but is dramatically reduced by their use in combination (indicating a synergistic effect). PD-1 expression in T cells of the same animals can also be modulated by treatment with a supplement containing fish oil and selenium, with the effects being enhanced by cotherapy with chemotherapeutic agents. Results of similar studies using a nutritional supplement containing fish oil and selenium ("N") in combination with Iressa ("I") or Tarceva ("T") are shown in FIG. 72. As shown PD-1 expression in T cells (left panel) is marginally reduced by treatment with Iressa or Tarceva (TI and TT, respectively), but returned to approximately normal levels by cotherapy with the nutritional supplement (TIN and TTN, respectively). Conversely, expression of PD-L1 in tumor cells is essentially unaffected by chemotherapeutic agents alone, but reduced by cotherapy with a nutritional supplement containing fish oil and selenium. Overall, this suggests that treatment with a supplement containing fish oil and selenium, chemotherapeutic agents, or a combination of treatment with such a supplement and one or more chemotherapeutic agents can potentiate or improve the outcome of immunotherapy in patients with cancer.

Figure 73:
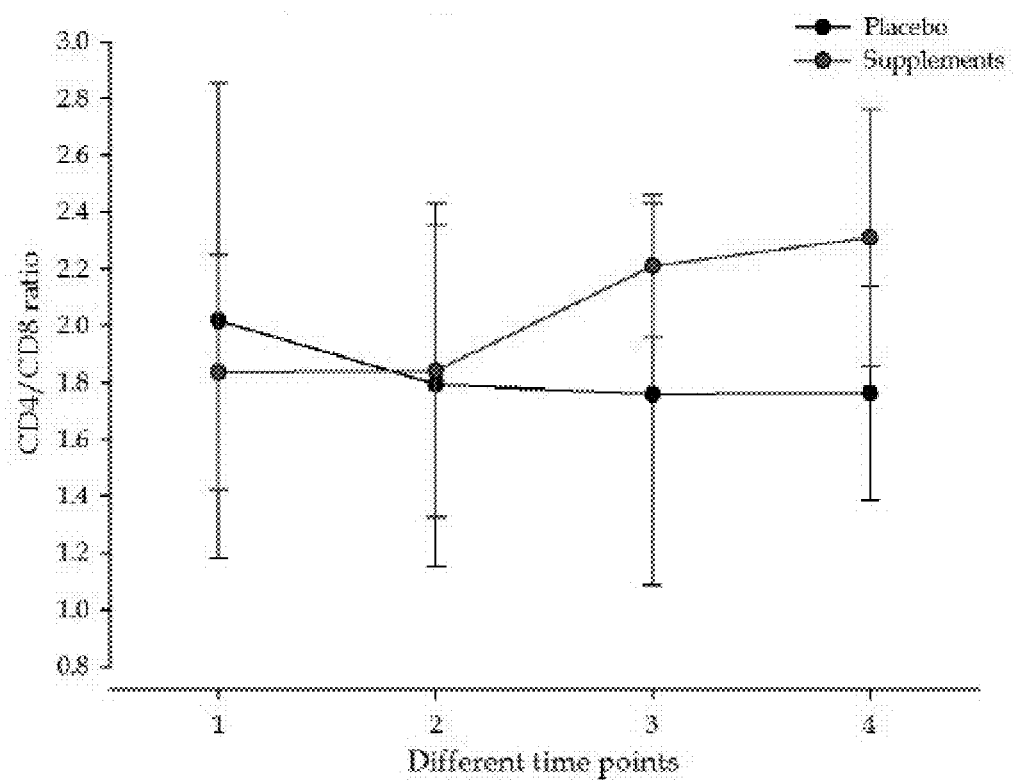
FIG. 73: Graph showing CD4/CD8 ratios of breast cancer patients receiving a nutritional supplement containing fish oil and selenium.
Figure 74:
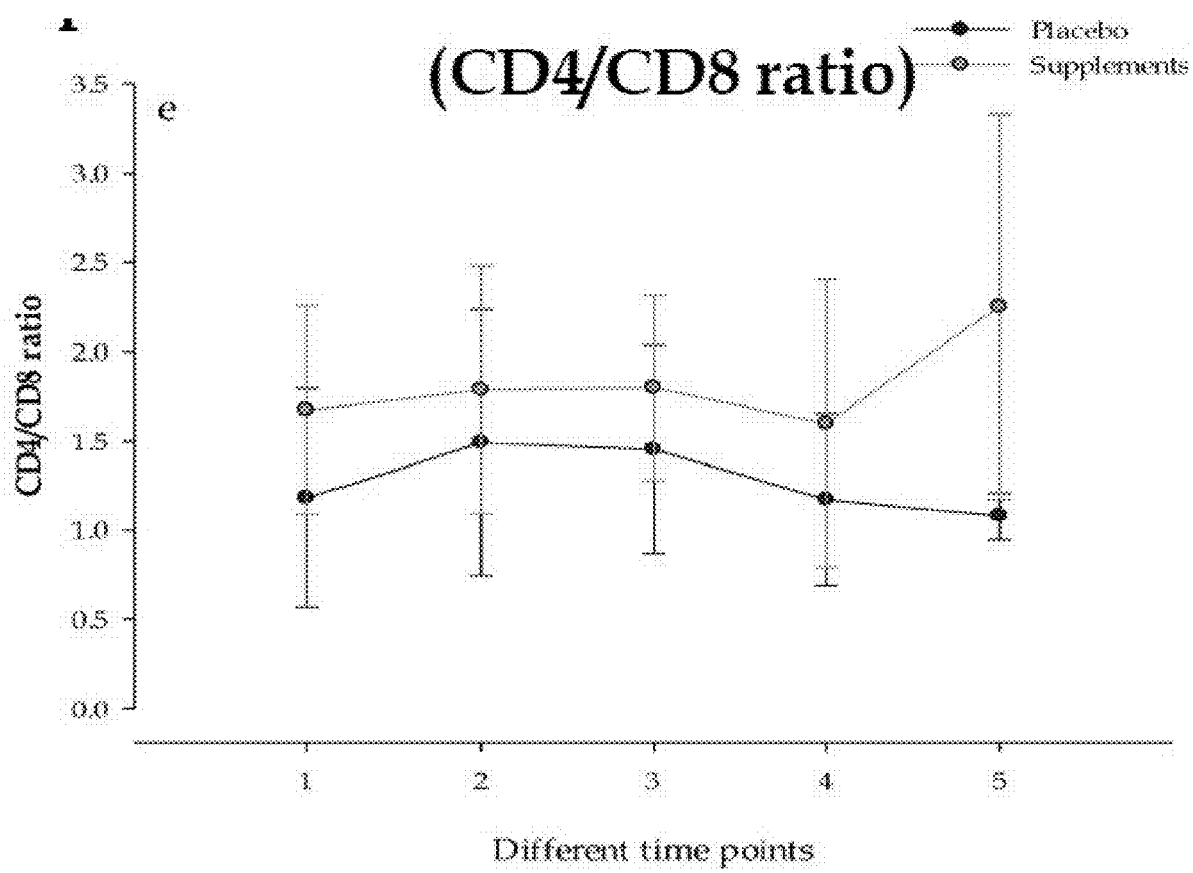
FIG. 74: Graph showing CD4/CD8 ratios of patients with lymphoma receiving a nutritional supplement containing fish oil and selenium.

Clinical data also demonstrate improved immune function in cancer patients receiving a nutritional supplement containing fish oil and selenium. For example, as shown in FIG. 73 and FIG. 74, CD4/CD8 ratios in breast cancer patients and lymphoma patients so treated are improved over patients receiving a placebo.

Overall, the Inventor believes that this indicates that nutritional supplements containing fish oil and selenium can enhance, in a complementary, additive, or synergistic manner, immunotherapeutic approaches to cancer treatment. The Inventor believes that this indicates that nutritional supplements containing fish oil and selenium can enhance, in a complementary, additive, or synergistic manner, immunotherapeutic approaches to cancer treatment.

Wasting/Cachexis

Figure 75:
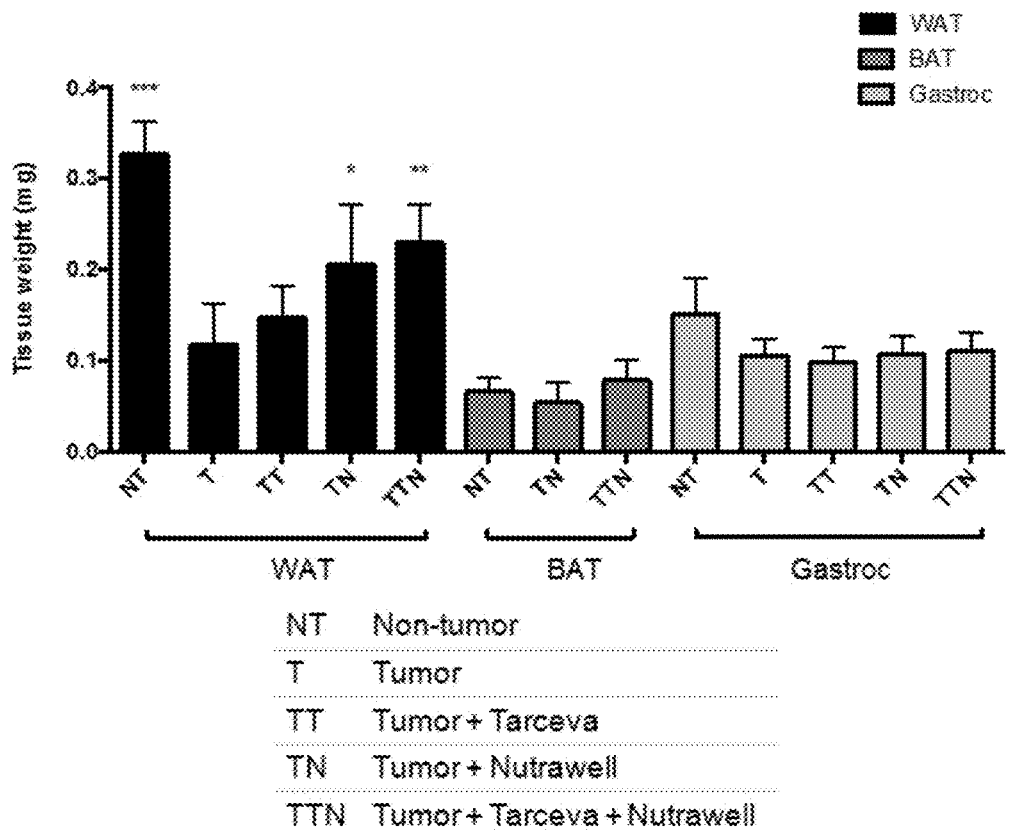
FIG. 75: Histogram of showing relative loss of adipose tissue and muscle mass in tumor implanted mice treated with a nutritional supplement containing fish oil and selenium and/or a chemotherapeutic agent.

Individuals with cancer frequently present with weight loss, due to loss of fatty tissue and muscle wasting (cachexis). This weight loss can result in serious health issues in addition to those resulting directly from tumor growth and progression. The Inventor has found that a nutritional supplement that includes fish oil and selenium can reduce cachectic symptoms, particularly when used in combination with one or more chemotherapeutic agents. Mice having tumors, with or without treatment with chemotherapeutic agents also experience cachexis. Using such an animal model the Inventor has found, surprisingly, that treatment with a nutritional supplement that includes fish oil and selenium can reduce these effects. As shown in FIG. 75, loss of white adipose tissue (WAT), brown adipose tissue (BAT), and muscle mass (gastroc) is consistent with cachexis is observed in tumor bearing mice, and is only slightly relieved by chemotherapy with Tarceva. Treatment with a nutritional supplement that includes fish oil and selenium ("Nutrawell"), with or without co-treatment with the chemotherapy, improves retention of adipose tissue and muscle.

Figure 76:
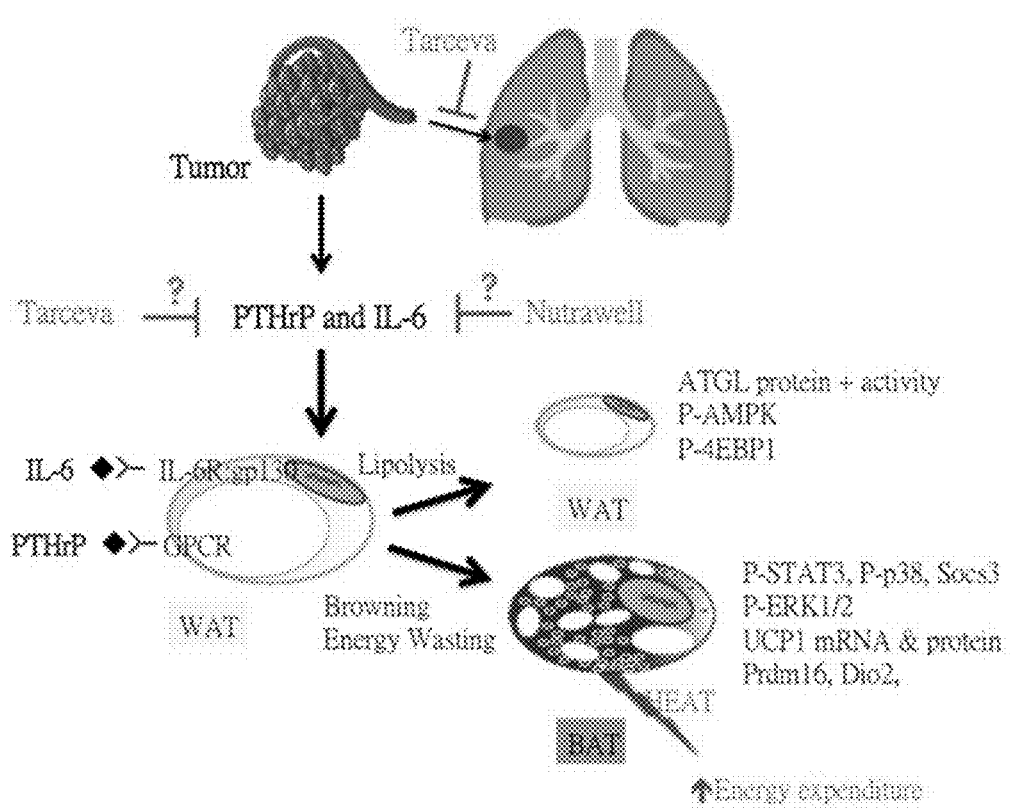
FIG. 76: Schematic depiction of the influence of tumor gene products on energy expenditure.
Figure 77:
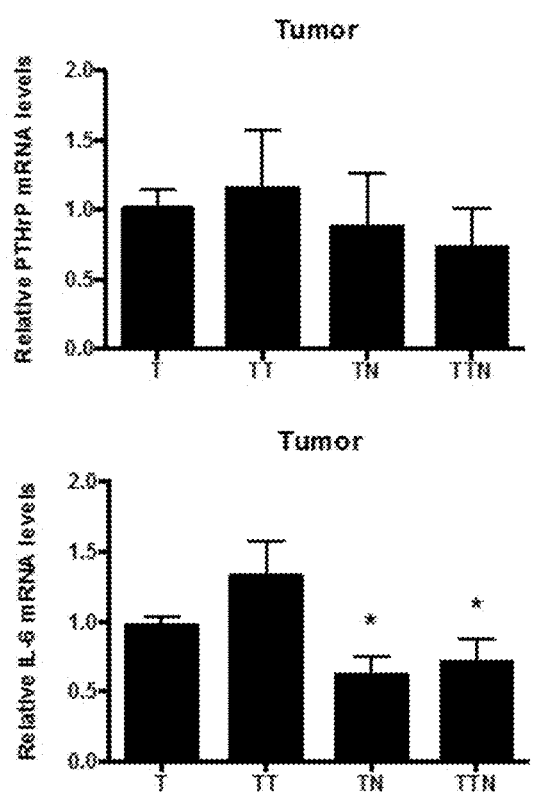
FIG. 77: Histograms showing the effects of treatment with a nutritional supplement containing fish oil and selenium and co-treatment with such a supplement and a chemotherapeutic agent in PTHrP and IL-6 expression in tumors.

As shown in FIG. 76, tumor cells can express gene products (such as PTHrP and IL-6) that can result in excessive cellular energy expenditure and waste. Some of these gene products (such as IL-6) are also associated with inflammation. These processes are thought to be associated with the development of cachexis. As shown in FIG. 77, treatment with a chemotherapy agent such as Tarceva can actually increase expression of such gene products. Surprisingly, treatment or chemotherapy-cotreatment with a nutritional supplement that includes fish oil and selenium ("Nutrawell") reduces the expression of such genes. This reduction in excess energy expenditure can beneficially help reduce inflammation and wasting, and provide more energy for recovery and immune response to a tumor.

Figure 78:
FIG. 78: Typical study design for characterizing the effects of cotherapy using a nutritional supplement containing fish oil and selenium with various chemotherapeutic drugs in tumor implanted mice.
Figure 79:
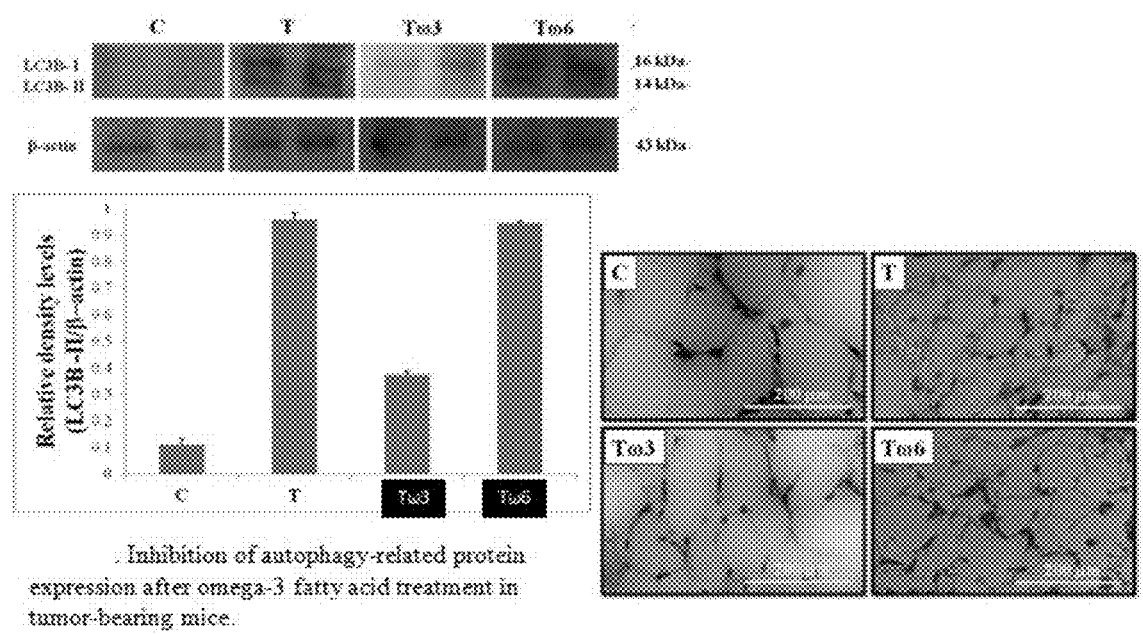
FIG. 79: Western blots, histograms, and photomicrographs showing expression of autophagy-related protein expression in tumor bearing mice treated with omega-3 fatty acid.
Figure 80:
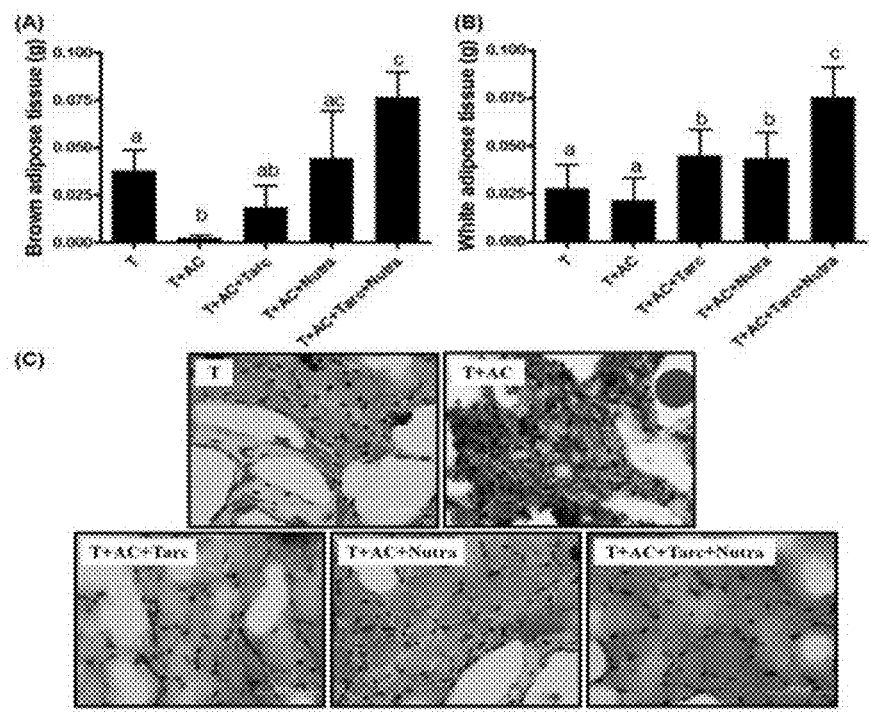
FIG. 80: Histograms and photomicrographs showing retention of adipose tissues in tumor-bearing mice treated with a nutritional supplement containing fish oil and selenium and/or chemotherapeutic agents.
Figure 81:
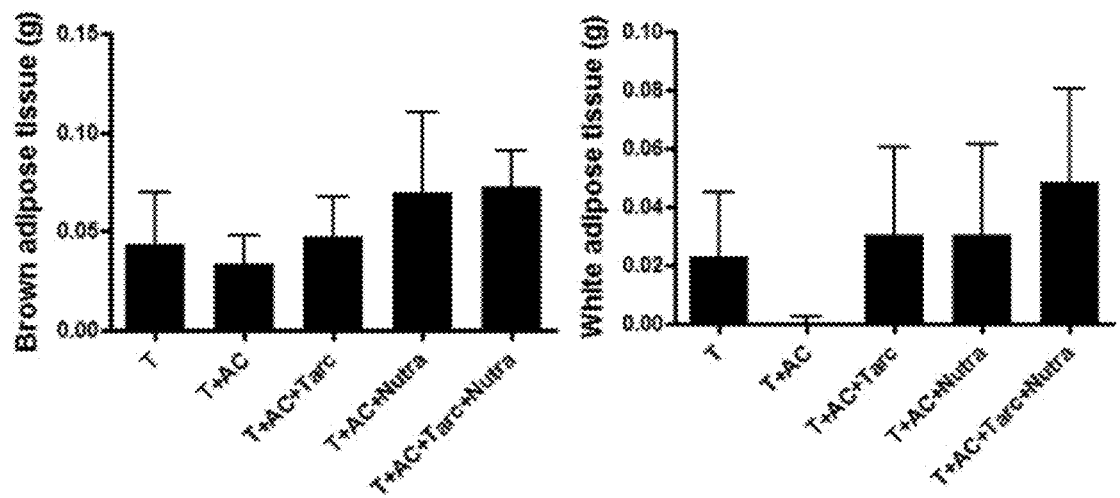
FIG. 81: Histograms showing effects of treatment with a nutritional supplement containing fish oil and selenium and/or chemotherapeutic agents on retention of white and brown adipose tissue in tumor-bearing mice.

In addition to the burden provided by a tumor, chemotherapy itself is associated with a variety of unpleasant and potentially dangerous cachectic effects. Surprisingly, the Inventor has found that these cachectic effects can be reduced or eliminated by providing a nutritional supplement that includes fish oil and selenium as cotherapy with chemotherapeutic drugs. An example of a typical study utilizing human tumor cells implanted in mice is shown in FIG. 78 and such a nutritional supplement that includes fish oil and selenium ("Nutrawell"). As shown, some groups of mice were treated with multiple chemotherapeutic drugs. As shown in FIG. 79, treatment with an omega-3 fatty acids (e.g. T$\omega$3, T$\omega$6), such as found in fish oil, can inhibit the expression of proteins associated with autophagy (such as LC3B-I and/or LC3B-III) in tumor-bearing mice. Such a reduction in autophagy can be associated with retention of body mass and body tissues in tumor bearing mice, particularly during chemotherapy. As shown in FIG. 80 and FIG. 81, treatment of tumor bearing mice with chemotherapeutic agents reduces adipose tissue weight beyond the effect of the tumor alone. Combination of such chemotherapy with a nutritional supplement that includes fish oil and selenium ("Nutra"), however, provides a dramatic improvement in adipose tissue weight.

Figure 82:
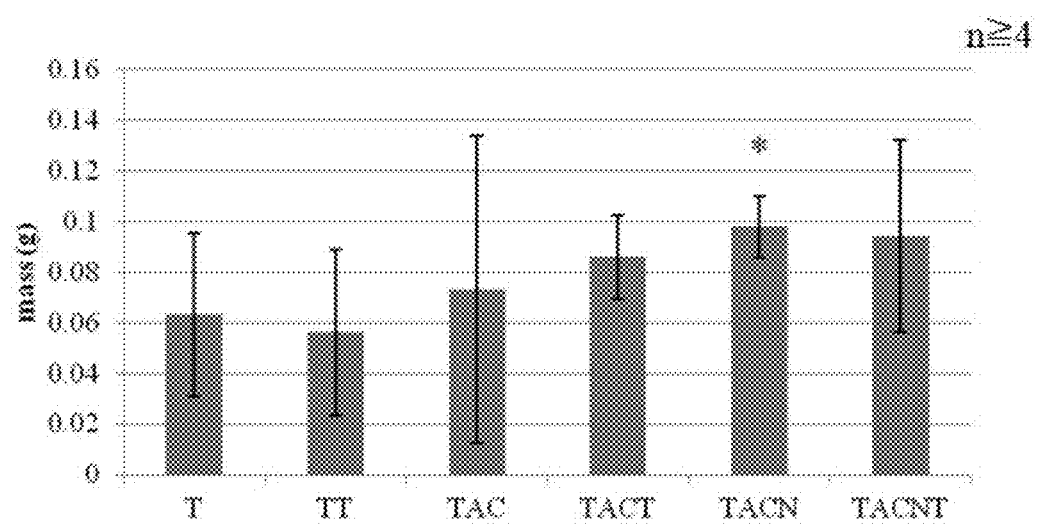
FIG. 82: Histograms showing effects of treatment with a nutritional supplement containing fish oil and selenium and/or chemotherapeutic agents on retention of gastrocnemius muscle mass in tumor-bearing mice.
Figure 83:
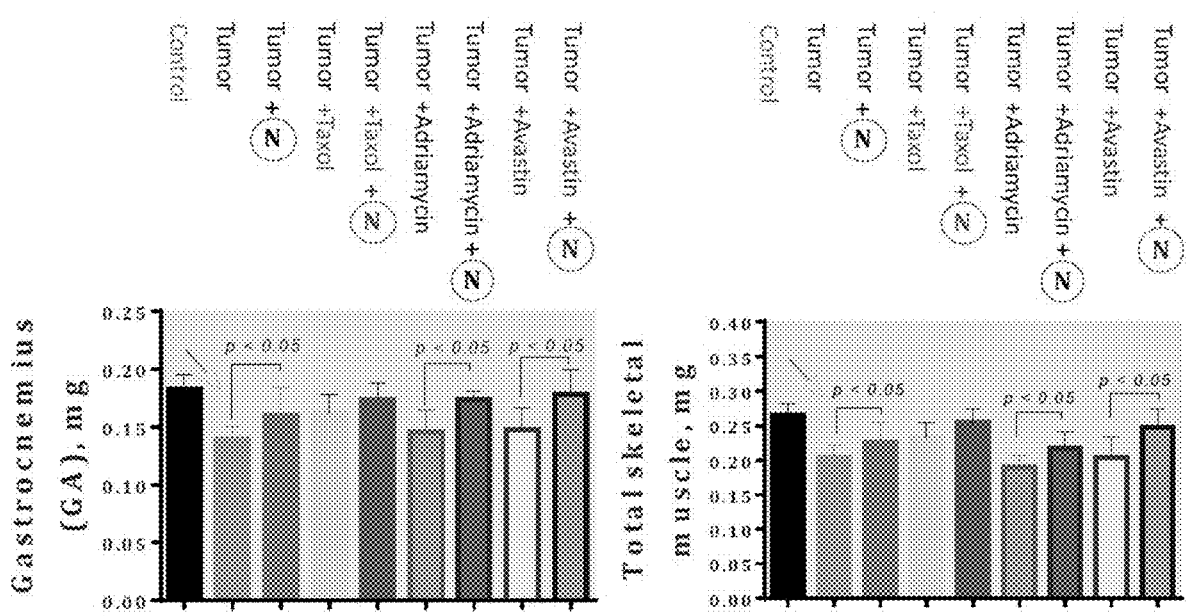
FIG. 83: Histograms showing effects of treatment with a nutritional supplement containing fish oil and selenium and/or chemotherapeutic agents on retention of gastrocnemius muscle mass and total skeletal muscle mass in tumor-bearing mice.
Figure 84:
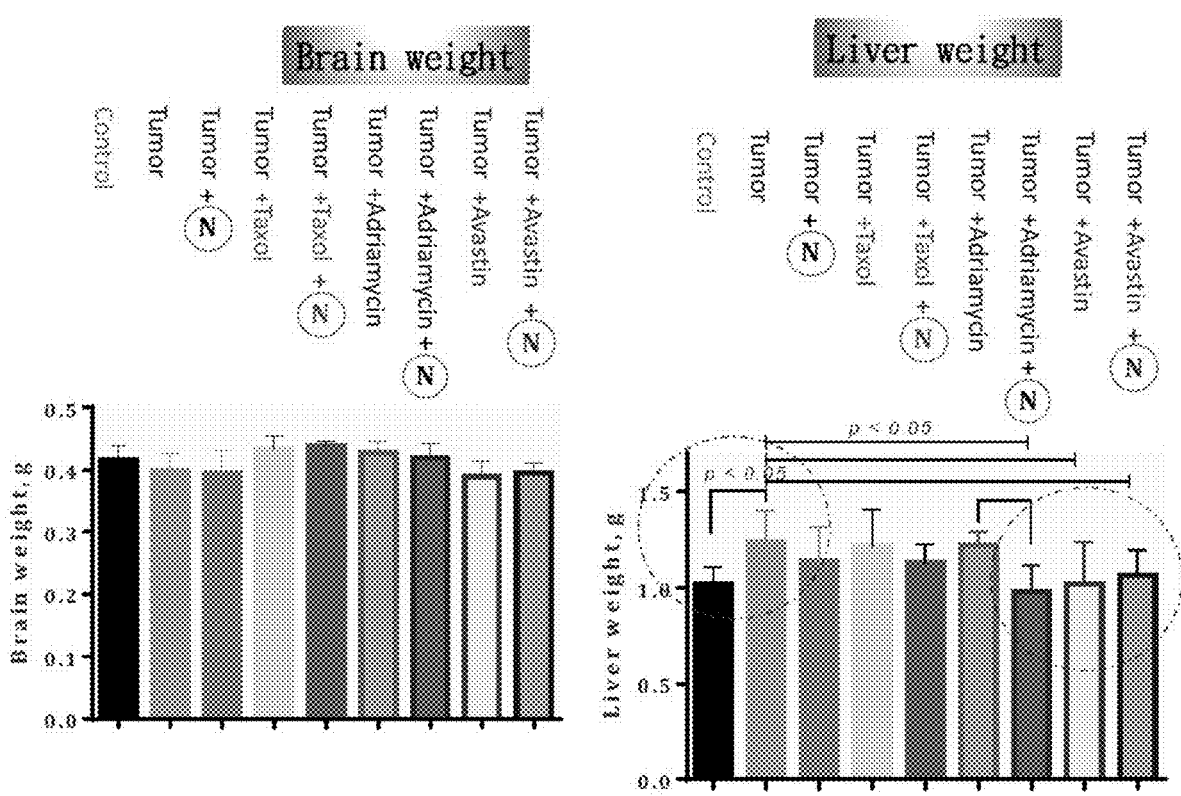
FIG. 84: Histograms showing effects of treatment with a nutritional supplement containing fish oil and selenium and/or chemotherapeutic agents on brain weight and liver weight in tumor-bearing mice.
Figure 85:
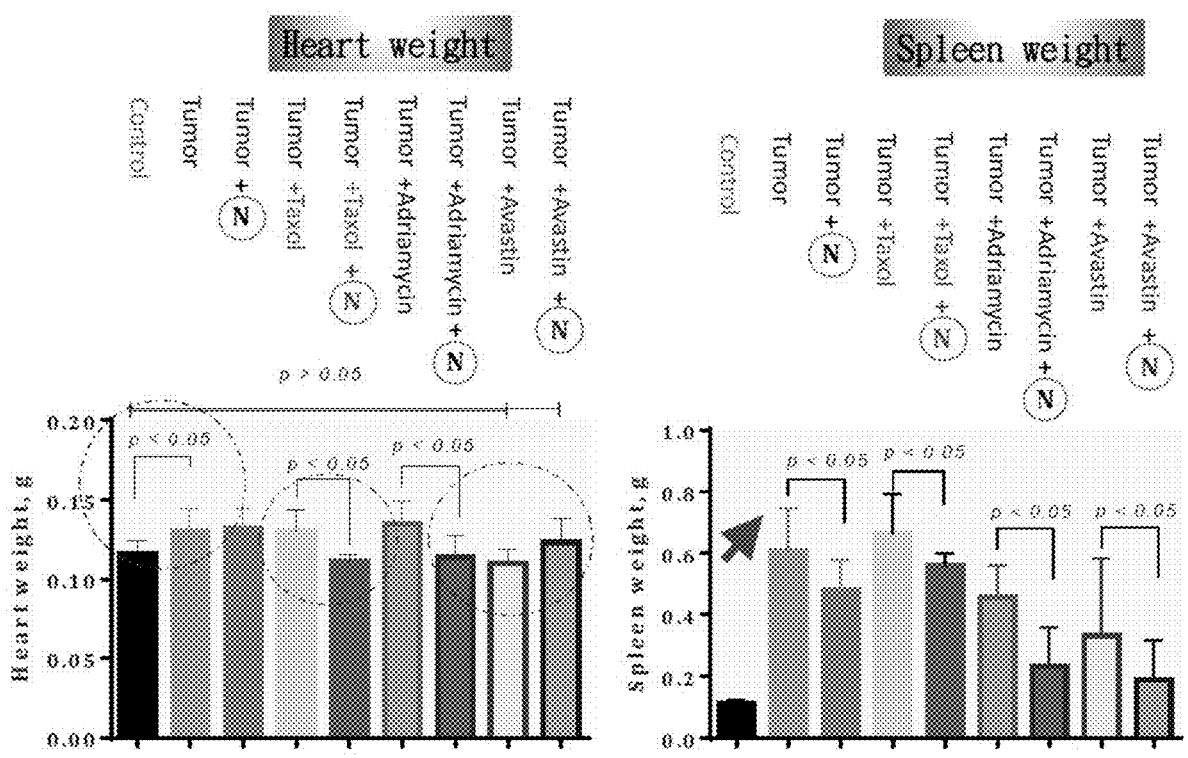
FIG. 85: Histograms showing effects of treatment with a nutritional supplement containing fish oil and selenium and/or chemotherapeutic agents on heart weight and spleen weight in tumor-bearing mice.
Figure 86:
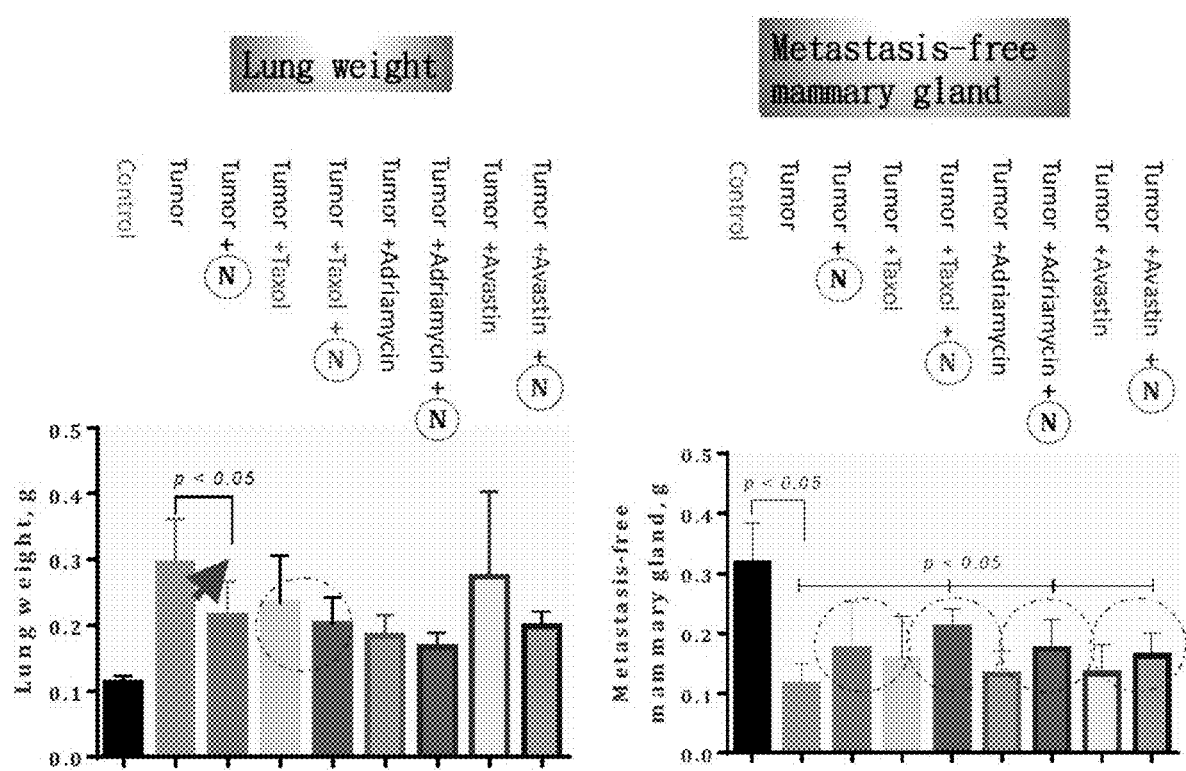
FIG. 86: Histograms showing effects of treatment with a nutritional supplement containing fish oil and selenium and/or chemotherapeutic agents on lung weight and metastasis-free mammary gland weight in tumor-bearing mice.

As shown in FIG. 82, cotherapy with a nutritional supplement that includes fish oil and selenium can also relieve muscle wasting (in this instance characterized by mass of the gastrocnemius muscle). Similar data was obtained for both gastrocnemius muscle weight and total skeletal muscle weight (see FIG. 83). As shown, cotherapy with a nutritional supplement that includes fish oil and selenium ("N") and chemotherapeutic drugs (Alimta/Cisplatin or AC, Tarceva or T) provides an improvement in the retention of muscle mass relative to that found with unsupplemented chemotherapeutic drug treatment. Similar results were found in evaluating the effect of a nutritional supplement that includes fish oil and selenium ("N") with different chemotherapeutic agents on the weights of various organs, including brain (FIG. 84, left panel), liver (FIG. 84, right panel), heart (FIG. 85, left panel), spleen (FIG. 85, right panel), lung (FIG. 86, left panel), and metastasis-free mammary gland (FIG. 86, right panel).

Figure 87:
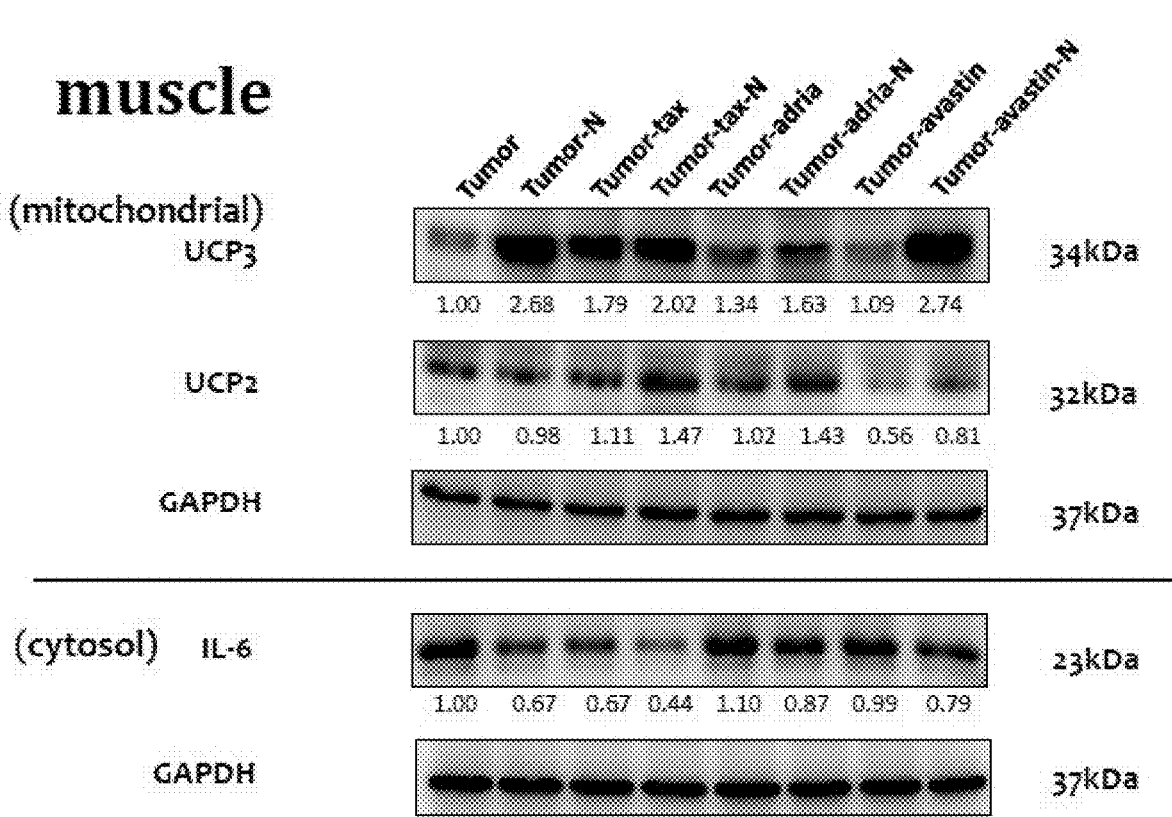
FIG. 87: Western blots showing the effect of a nutritional supplement containing fish oil and selenium in combination with chemotherapeutic agents on muscle mitochondrial and inflammation (i.e. IL6) markers in an in vivo model of breast cancer. GAPDH is included as a control.
Figure 88:
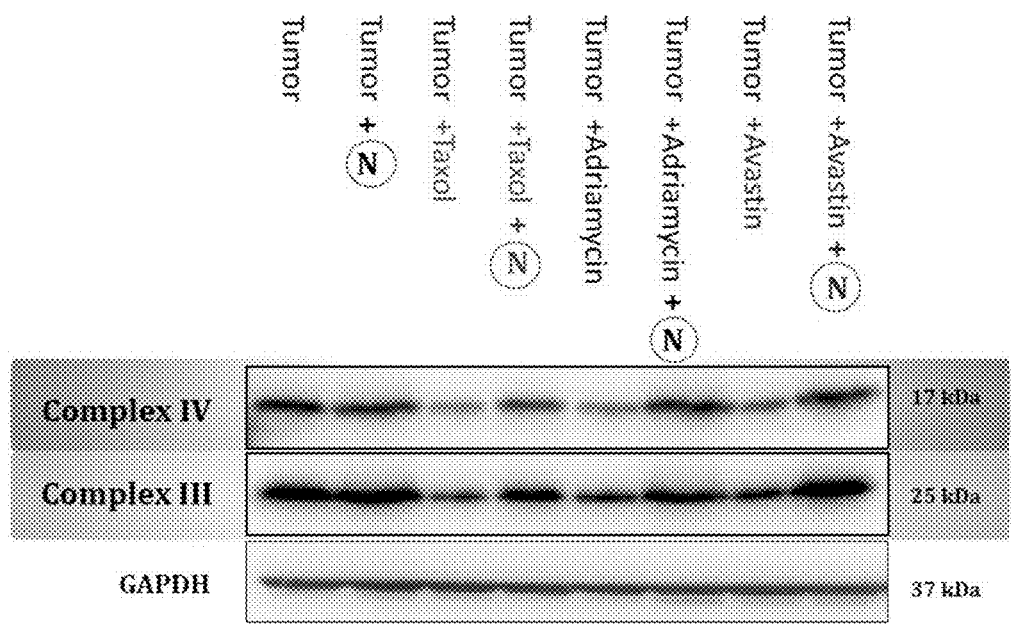
FIG. 88: Western blots showing the effect of a nutritional supplement containing fish oil and selenium in combination with chemotherapeutic agents on Complex III and Complex IV mitochondrial complex proteins in an in vivo model of human cancer. GAPDH is included as a control.

Reduction in cachectic symptoms on treatment with a nutritional supplement that includes fish oil and selenium in combination with a chemotherapeutic agent is also evident on a molecular level. The Inventor has observed that use of such a nutritional supplement is effective in preventing or reversing changes in the expression of specific biochemical markers associated with muscle wasting and inflammation, whether used in isolation or in combination with chemotherapeutic agents (e.g. Taxol, Adriamycin, Avastin). This is also apparent at the molecular level, as shown in FIG. 87. FIG. 87 shows expression of muscle-related proteins found in mitochondria (UCP3, UCP2) and an inflammation-related cytokine in cytosol (IL6). FIG. 88 shows expression of another set of mitochondrial muscle markers, Complex IV and Complex III. Use of a nutritional supplement that includes fish oil and selenium resulted in a marked increase in mitochondrial proteins, whether used in isolation or in combination with Taxol, Adriamycin, or Avastin. Conversely inflammation in muscle tissue was reduced, as indicated by a reduction in IL6, whether used in isolation or in combination with Taxol, Adriamycin, or Avastin.

Figure 89:
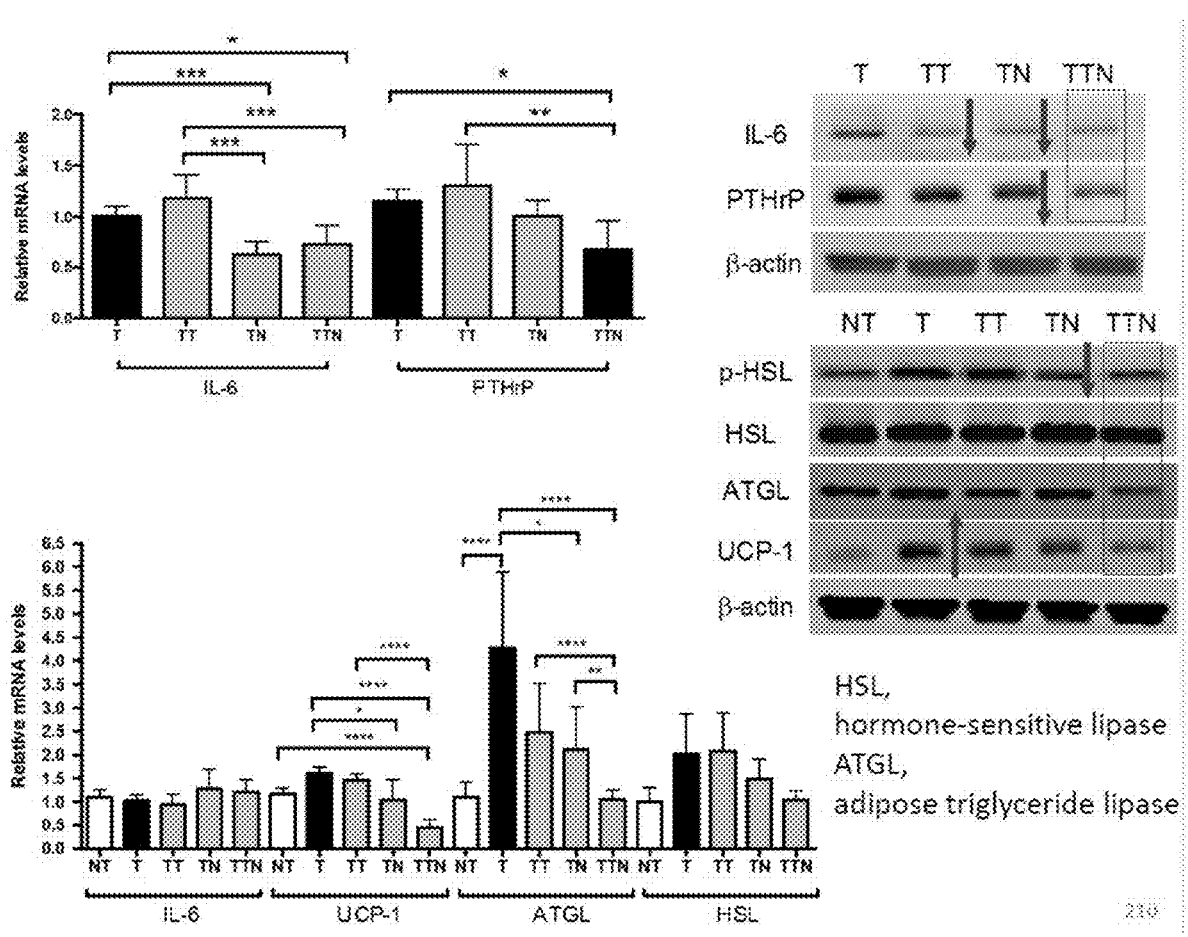
FIG. 89: Results of rtPCR and Western blot studies of IL-6, PTHrP, UCP-1, ATGL, and HSL expression in animal models of human cancer.

Treatment with a nutritional supplement containing fish oil and selenium, with or without cotherapy using chemotherapeutic agents, was also found to modulate expression of biochemical markers associated with fat tissue and metabolism. As shown in FIG. 89 (lower left panel), expression of UCP-1 and ATGL is increases in tumor tissue (T) relative to non-tumor tissue (NT). This is decreased somewhat by treatment with Taxol (TT) and by treatment with a nutritional supplement including fish oil and selenium (TN), however a marked (i.e. synergistic) reduction in expression is seen on combined treatment (TTN). Similar results are evident for hormone sensitive lipase (HLS) and adipose triglyceride lipase (ATGL) along with UCP-1 in Western blots FIG. 89, right panel).

Surprisingly, treatment with a nutritional supplement that includes fish oil and selenium was also found to reduce expression of PTHrP in tumor bearing animals (TN, see top left panel of FIG. 89). This effect was potentiated in a synergistic manner when a chemotherapeutic agent (Taxol), which actually increased expression when used alone (TT), was used in cotherapy (TTN). This indicates that supplements containing fish oil and selenium can be useful in treating mineral imbalance in cancer patients.

Figure 90:
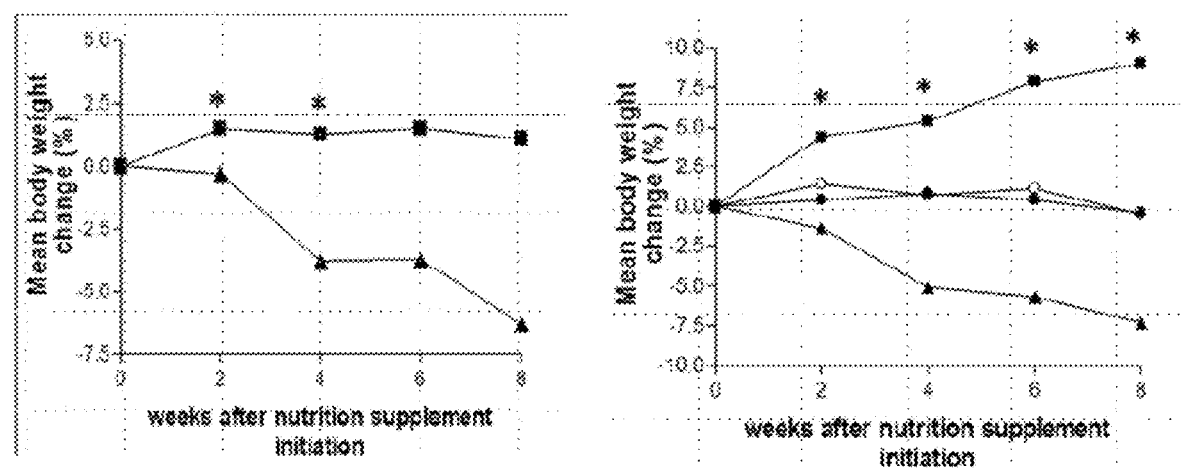
FIG. 90: Graphs showing reductions in cachexia in patients with head and neck cancers using a nutritional supplement containing fish oil and selenium. The left panel shows mean changes in body weight for patients treated with a nutritional supplement containing fish oil and selenium (squares) and a generic supplement (triangles). The right panel shows mean changes in body weight for patients having a BMI less than or equal to 19 who were treated with a nutritional supplement containing fish oil and selenium (squares), mean changes in body weight for patients having a BMI >19 who were treated with a nutritional supplement containing fish oil and selenium (open circles), patients with a BMI less than or equal to 19 treated with a generic supplement (triangles), and patients with a BMI greater than 19 treated with a generic supplement (filled circles).

Improvement in cachexia in patients with head and neck cancer on use of a nutritional supplement that includes fish oil and selenium was also observed in clinical studies. As shown in FIG. 90, such a nutritional supplement is effective in both maintaining body weight (left panel) and in some instances (e.g. having a BMI <19) increasing body weight (right panel). Similar results are seen in animal models, as shown in FIG. 22 (left panel). It should be appreciated that these effects are not due to a simple increase in caloric intake, as treatment with a conventional nutritional supplement in similar caloric amounts did not provide this effect.

Figure 91:
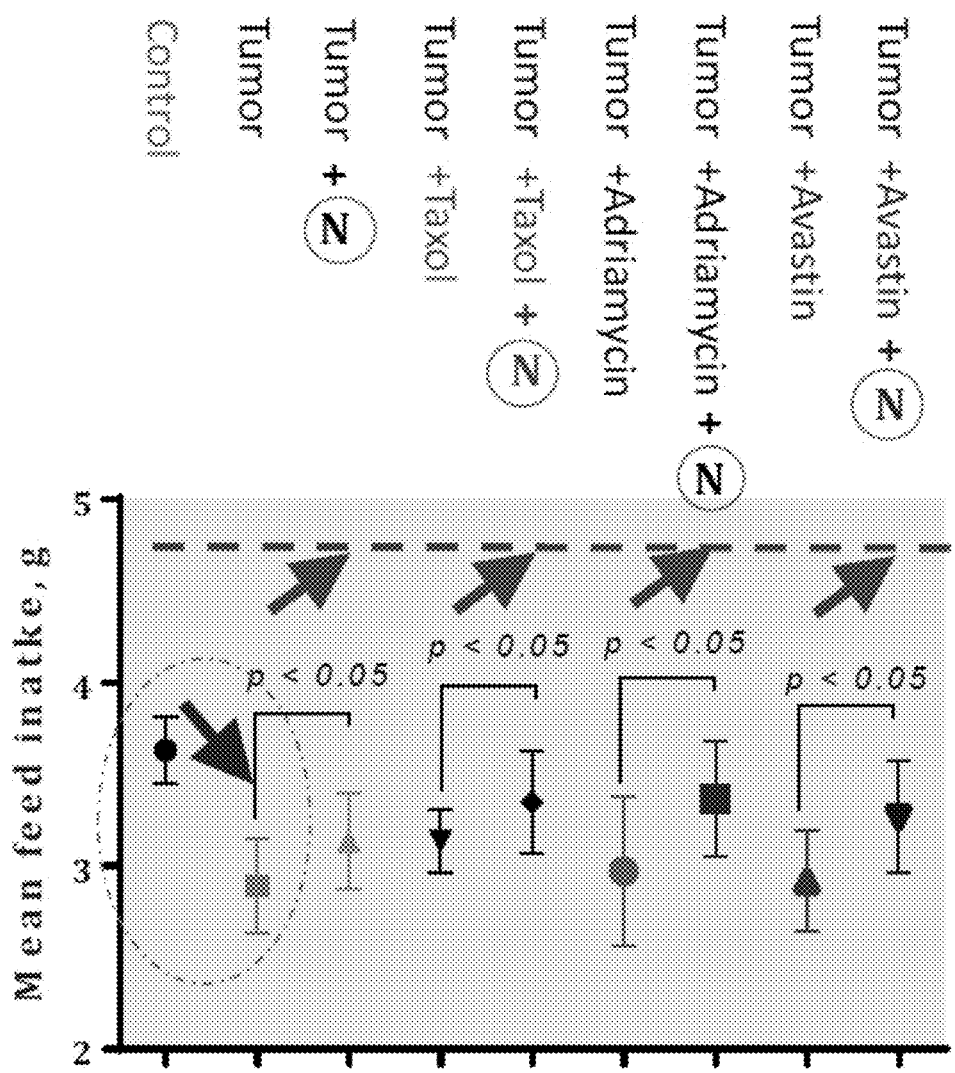
FIG. 91: Graph of the effect of a nutritional supplement containing fish oil and selenium in combination with chemotherapeutic agents on feed intake in an in vivo model of human cancer.

Presence of a tumor and use of chemotherapy is frequently associated with nausea and loss of appetite, which can contribute to cachexia. Surprisingly, the Inventor has found that use of a nutritional supplement that includes fish oil and selenium can increase feed intake in animal models, despite the additional calories provided by the supplement itself (see FIG. 91).

Cytokine Expression

Figure 92:
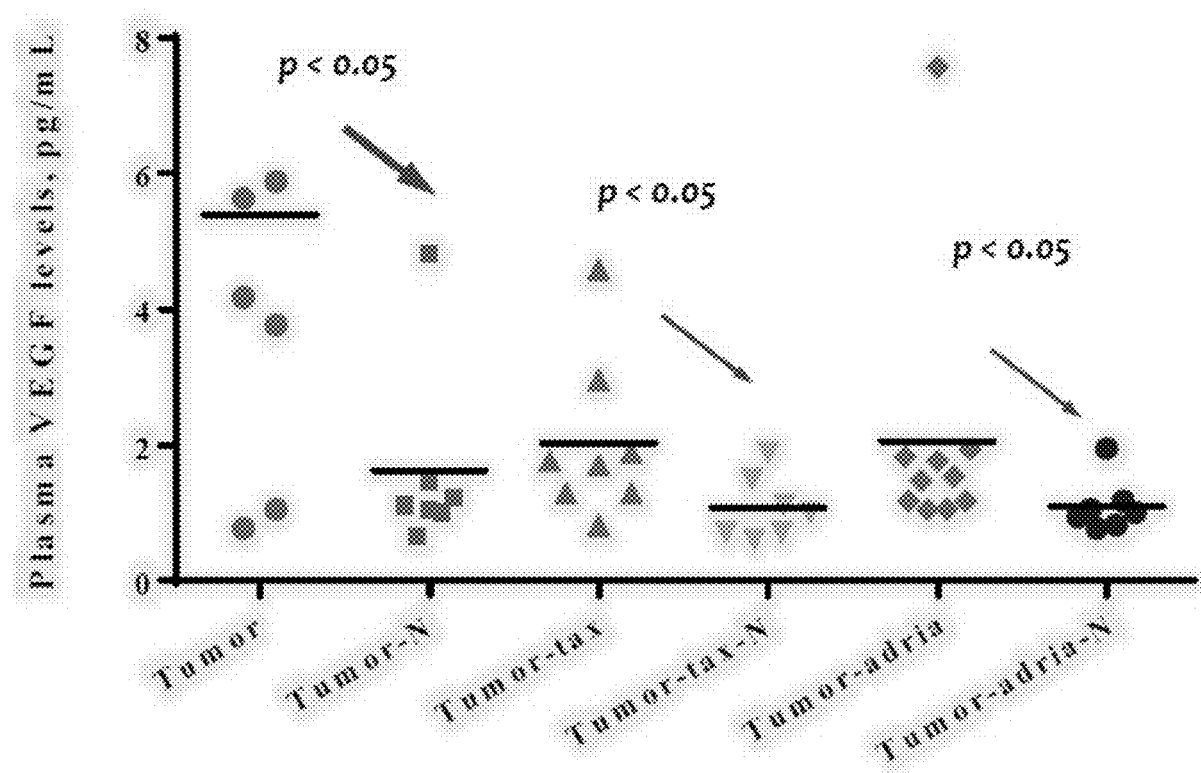
FIG. 92: Graph of the effect of a nutritional supplement containing fish oil and selenium in combination with chemotherapeutic agents on plasma concentrations of VEGF in an in vivo model of breast cancer.
Figure 93:
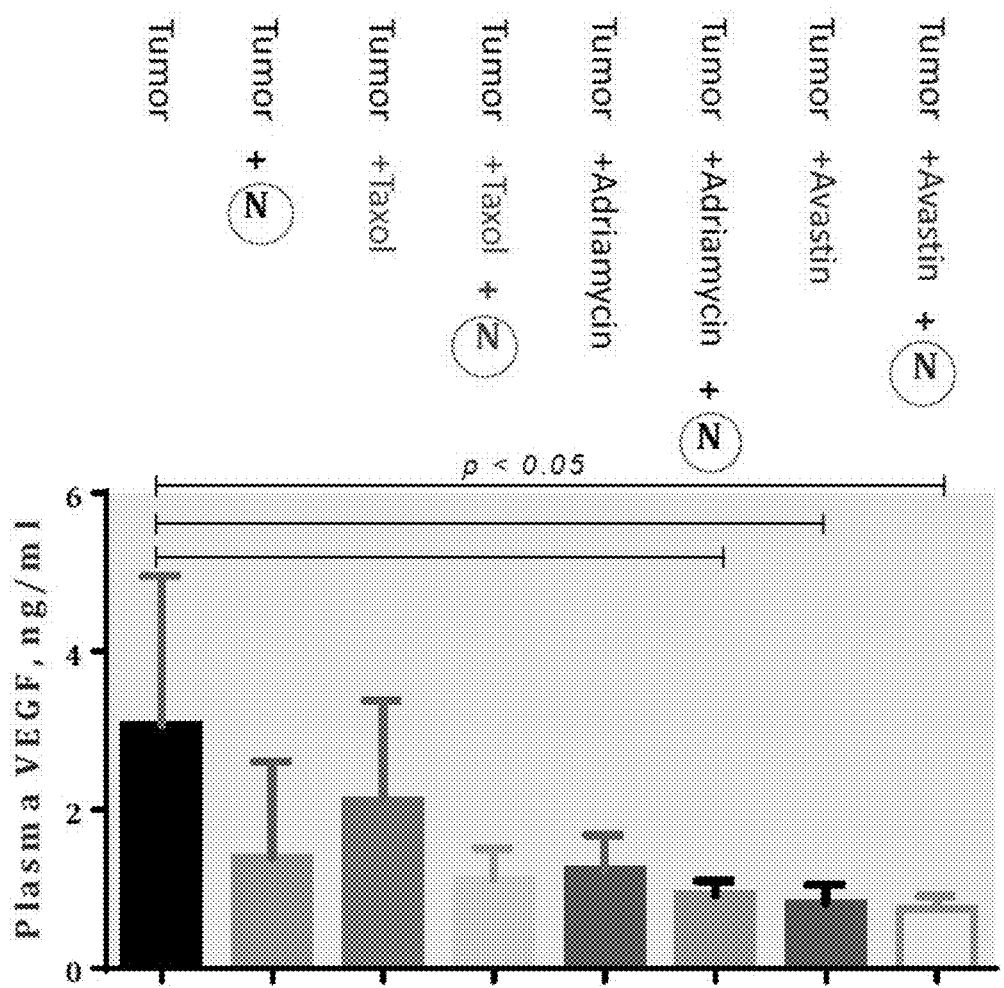
FIG. 93: Histogram of the effect of a nutritional supplement containing fish oil and selenium in combination with Taxol, Adriamycin, or Avastin agents on plasma concentrations of VEGF in an in vivo model of breast cancer.

The presence of tumors is frequently associated with inflammation, a process that is at least in part mediated by cytokines. Cytokines can also be involved in other tumor-related processes, such as angiogenesis. Surprisingly, the Inventor has found that a nutritional supplement that includes fish oil and selenium can modulate levels of various cytokines, particularly when used in combination with chemotherapeutic drugs. As shown in FIG. 92 use of such a nutritional supplement in combination with chemotherapeutic agents (Taxol, pr "tax", and Adriamycin, or "adria", in this example) in in vivo models of breast cancer was found to reduce plasma VEGF concentrations, indicating that it can provide an anti-inflammatory and anti-angiogenesis effect. Similar results are seen with Avastin (see FIG. 93). The effect is seen with the supplement alone, and cotherapy with such a supplement enhances the VEGF-lowering effects of chemotherapeutic drugs.

Figure 94:
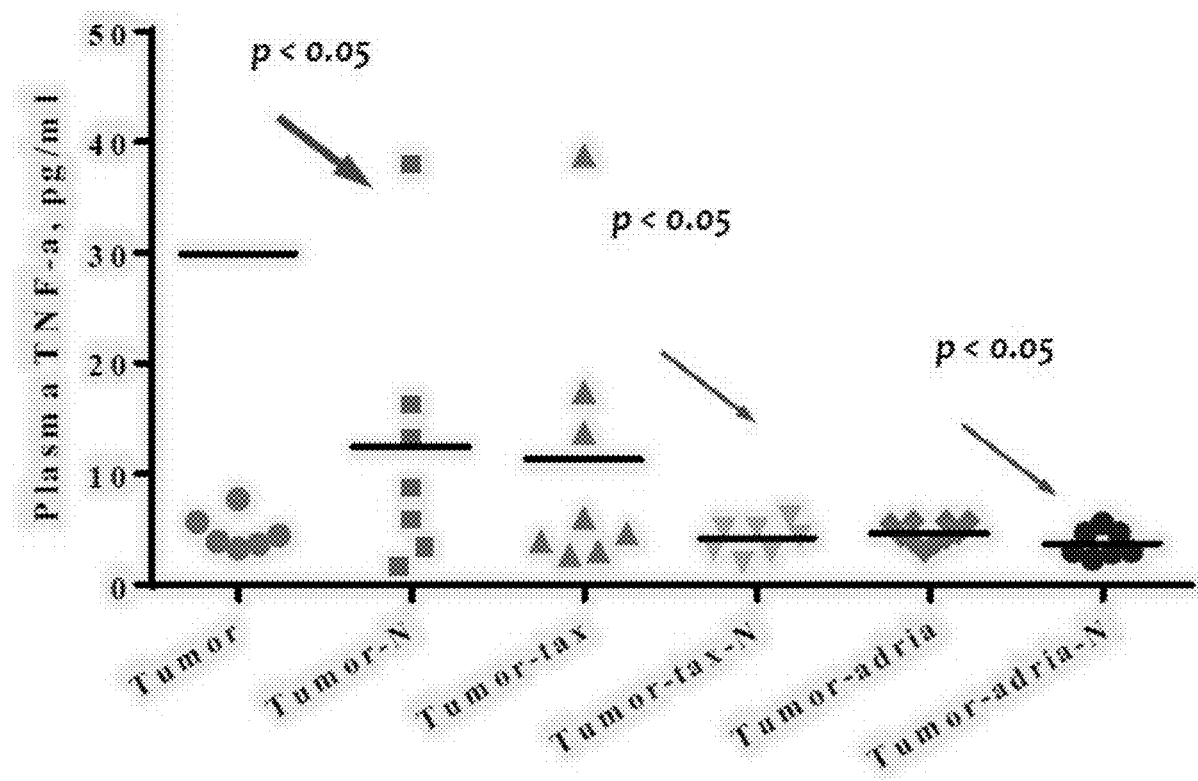
FIG. 94: Graph the effect of a nutritional supplement containing fish oil and selenium in combination with chemotherapeutic agents on plasma concentrations of TNF-α in an in vivo model of breast cancer.
Figure 95:
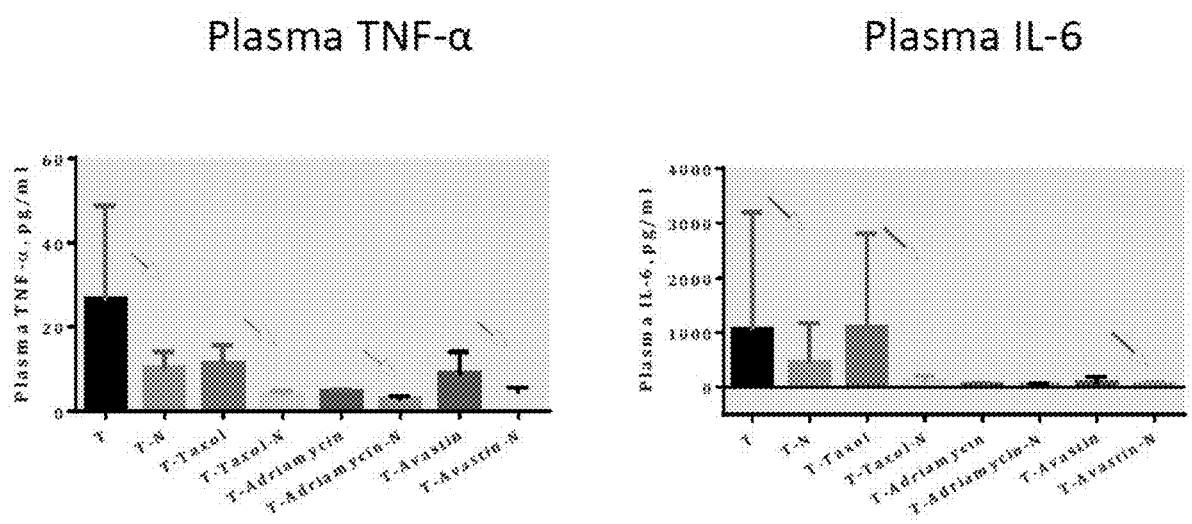
FIG. 95: Histograms of the effect of a nutritional supplement containing fish oil and selenium in combination with Taxol, Adriamycin, or Avastin agents on plasma concentrations of TNF-α and IL6 in an in vivo model of breast cancer.
Figure 96:
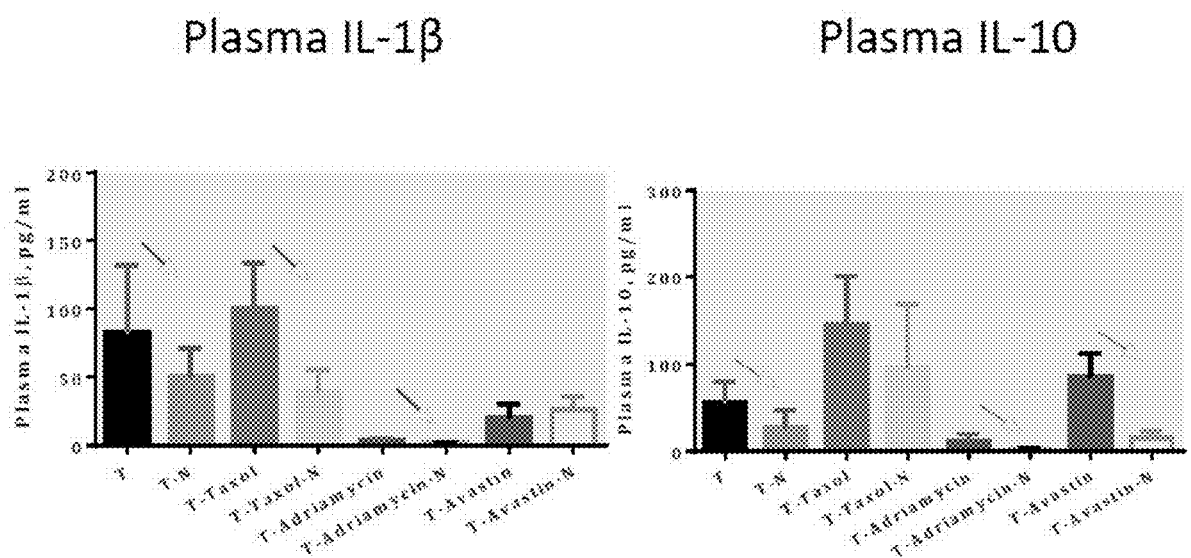
FIG. 96: Graphs of the effect of a nutritional supplement containing fish oil and selenium alone and in combination with Taxol, Adriamycin, or Avastin on plasma concentrations of m1-r3 and IL-10 in an in vivo models of human cancer.
Figure 97:
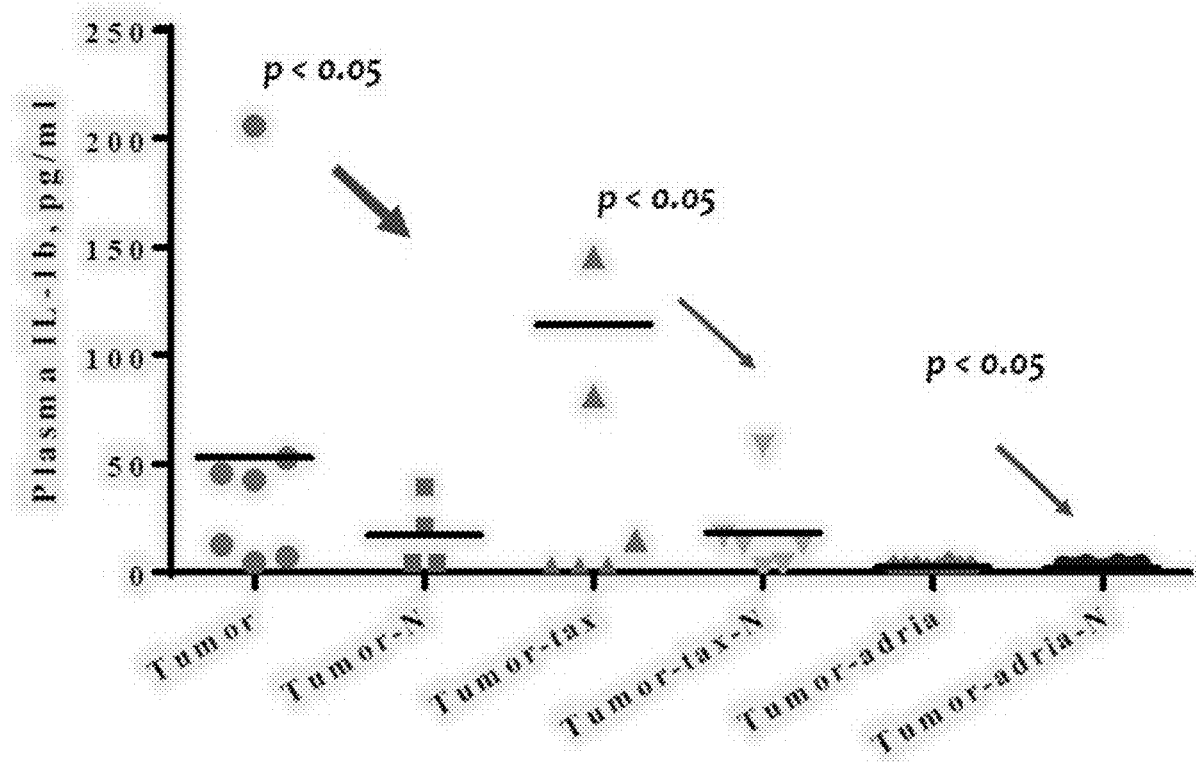
FIG. 97: Graph of the effect of a nutritional supplement containing fish oil and selenium in combination with chemotherapeutic agents on plasma concentrations of m1-r3 in an in vivo model of breast cancer.
Figure 98:
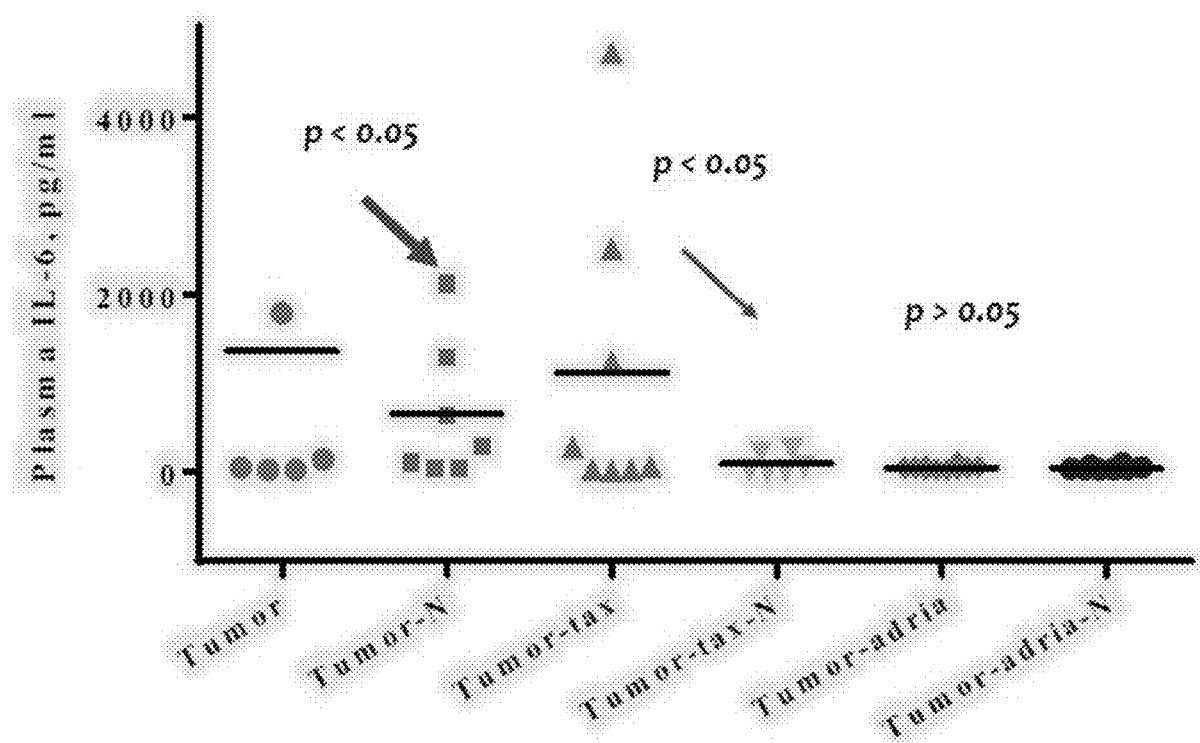
FIG. 98: Graph of the effect of a nutritional supplement containing fish oil and selenium in combination with chemotherapeutic agents on plasma concentrations of IL6 in an in vivo model of breast cancer.

As shown in FIG. 94 and FIG. 95 (left panel), similar effects are seen in the reduction of TNF-α, which is associated with tumor angiogenesis, growth, and metastasis, in an in vivo breast cancer model. Similar effects are seen in the reduction of IL1-β (see also FIG. 96, left panel), which is associated with tumor angiogenesis, growth, and metastasis. The effects of a nutritional supplement containing fish oil and selenium in combination, both alone and in combination with chemotherapy drugs, on plasma IL-1β in an in vivo model of breast cancer is shown in FIG. 97. Similar studies (see FIG. 98 and FIG. 95, right panel) show reductions in plasma IL6, which is associated with tumor angiogenesis, protection of tumors from oxidative stress, and anti-apoptotic effects. Plasma concentrations of IL-10 are similarly reduced (in some instances to nondetectable levels) in such in vivo tumor models treated with a supplement that includes fish oil and selenium (N), both alone and when used in combination with chemotherapeutic drugs—despite an elevation in concentration when such drugs are used alone (FIG. 96, right panel).

Figure 99:
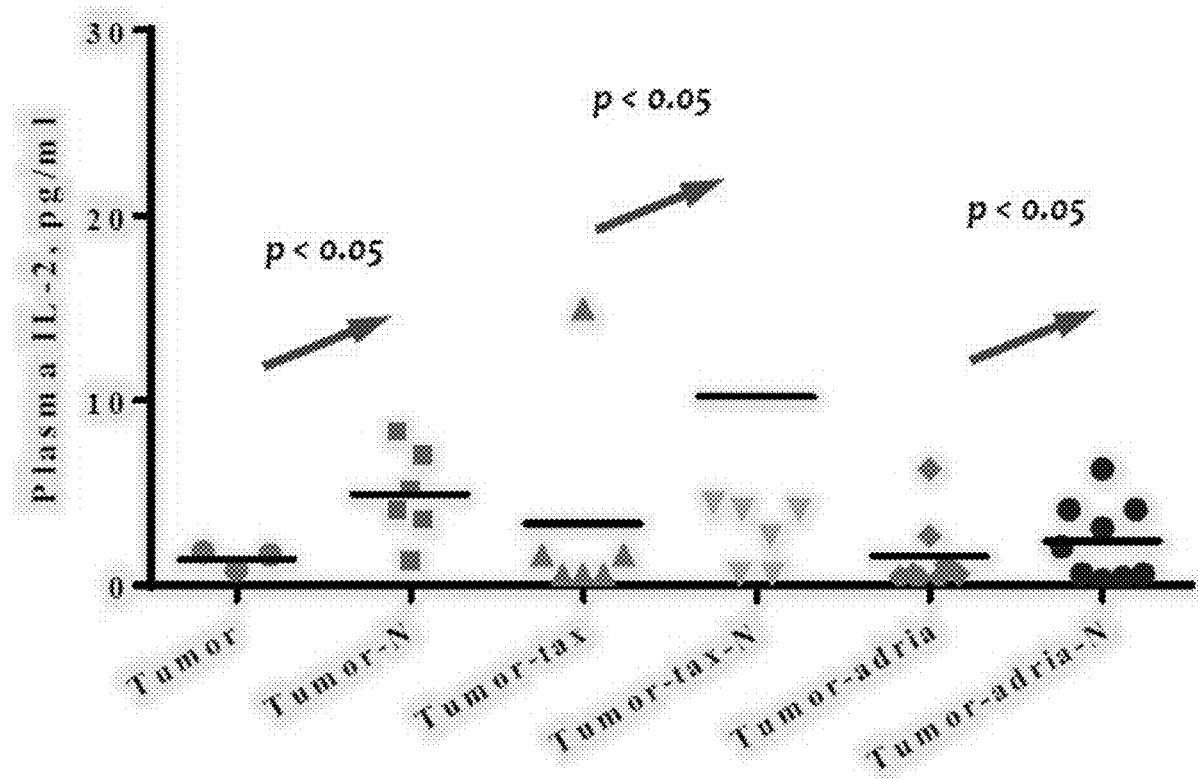
FIG. 99: Graph of the effect of a nutritional supplement containing fish oil and selenium in combination with chemotherapeutic agents on plasma concentrations of IL2 in an in vivo model of breast cancer.
Figure 100:
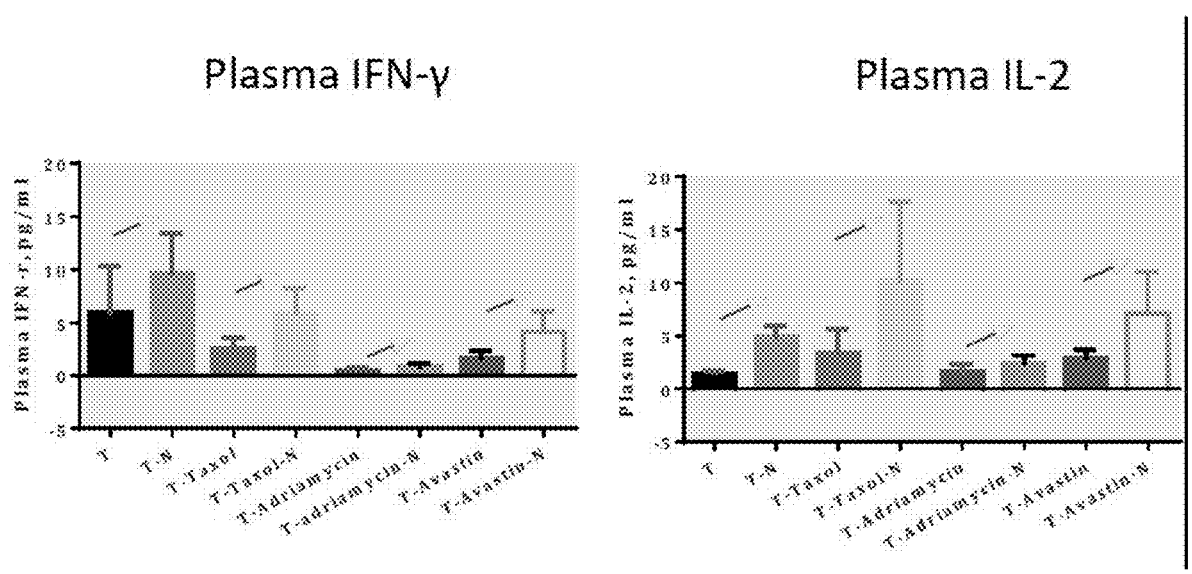
FIG. 100: Histograms of the effect of a nutritional supplement containing fish oil and selenium in combination with chemotherapeutic agents on plasma concentrations of IFN-γ and IL-2 in an in vivo model of breast cancer.
Figure 101:
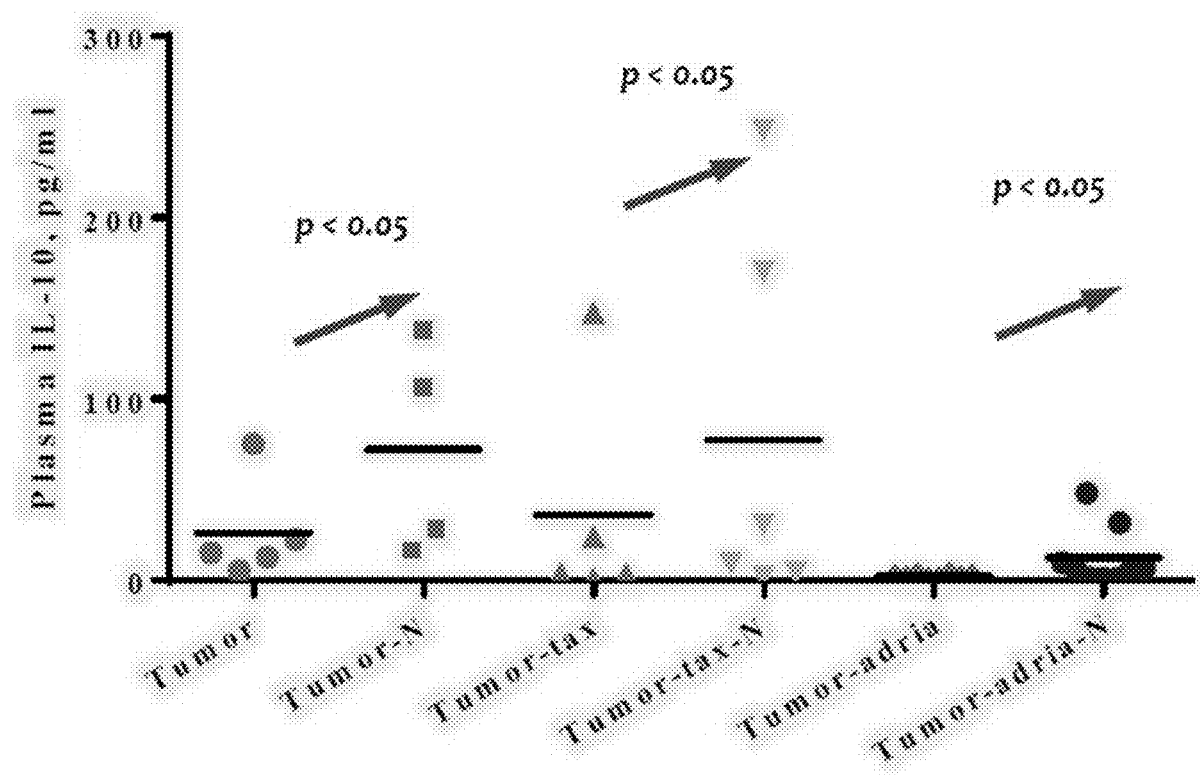
FIG. 101: Graph of the effect of a nutritional supplement containing fish oil and selenium in combination with chemotherapeutic agents on plasma concentrations of IL10 in an in vivo model of breast cancer.
Figure 102:
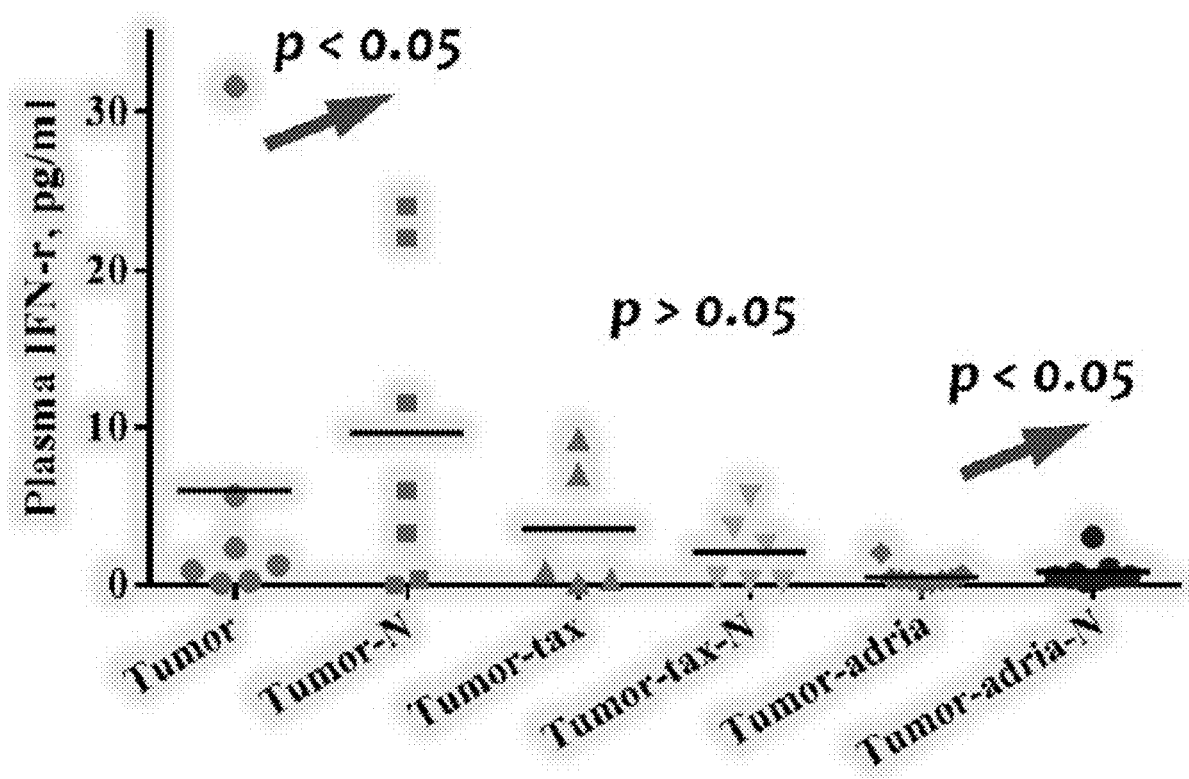
FIG. 102: Graph of the effect of a nutritional supplement containing fish oil and selenium in combination with chemotherapeutic agents on plasma concentrations of IFN-γ in an in vivo model of breast cancer.

Conversely, the Inventor has found that the use a nutritional supplement containing fish oil and selenium can increase plasma concentrations of some cytokines, both in isolation and in combination with chemotherapeutic drugs. For example, as shown in FIG. 99 and FIG. 100 (right panel) plasma concentrations of IL2 are increased in an in vivo model of breast cancer show treated. It should be appreciated that IL2 is considered an immunotherapeutic drug for the treatment of some cancers. Similar results are found for IL10 in an in vivo breast cancer model (see FIG. 101), which is another immune-activating cytokine. Plasma concentration of IFN-γ, another immune-activating cytokine, are also observed in such studies as shown in FIG. 102 and FIG. 100 (left panel).

Overall, the Inventor believes that a nutritional supplement that includes fish oil and selenium can be useful to reduce plasma concentrations of cytokines associated with inflammation and tumor growth/progression, both as a monotherapy and in combination with one or more chemotherapeutic drugs. It should be appreciated that such a reduction can be provided even when such chemotherapeutic drugs result in an increase in the plasma concentration of such cytokines when used in the absence of such a supplement, and that the reduction is potentiated by cotherapy (indicating a synergistic effect). Similarly, use of such a supplement can result in increased plasma concentrations of immune-activating cytokines, both when used as a monotherapy and when used in combination with one or more chemotherapeutic drugs.

AXL Signaling

Figure 103:
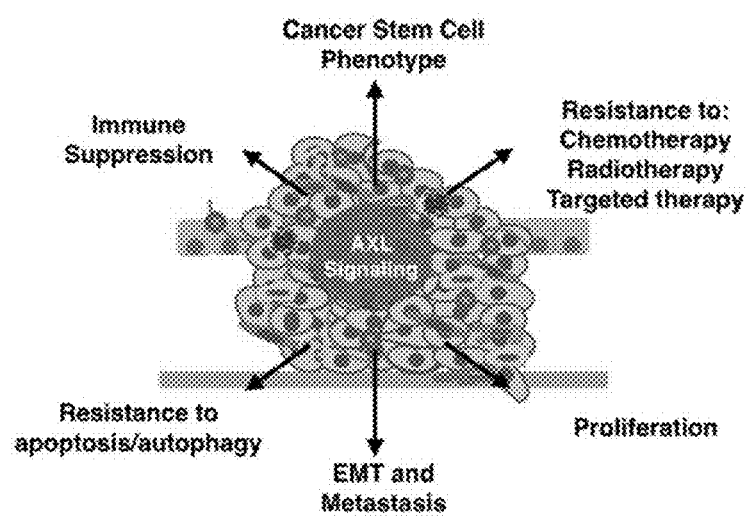
FIG. 103: Schematic depiction of AXL signaling and factors influencing tumor progression.

As shown in FIG. 103, AXL signaling in tumors is associated with a wide variety of downstream effects that promote tumor progression. As shown, AXL signaling within the tumor microenvironment can promote immunosuppression, the development of cancer stem cell phenotypes, resistance to various anti-cancer therapies (including anti-cancer drugs), tumor cell proliferation, resistance to apoptosis and/or autophagy, epithelial to mesenchymal transition, and metastatis. As such, regulation of AXL signaling (for example, returning the cell to a state more closely resembling that of a normal cell) can provide a therapeutic target for treatment of cancers, particularly drug resistant cancers.

Figure 104:
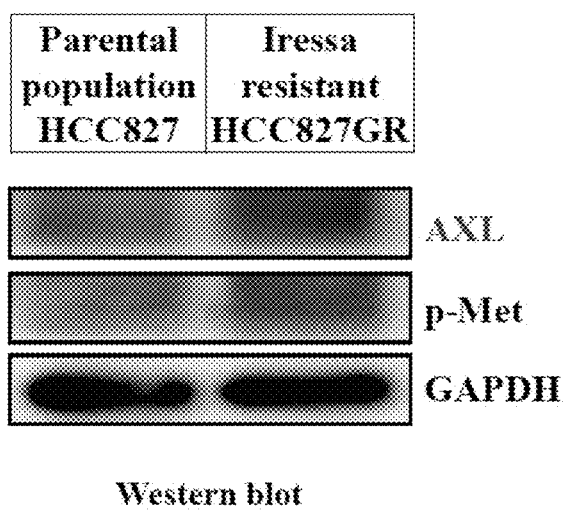
FIG. 104: Western blot of AXL and p-MET expression in HCC827 and HCC827GR (Iressa-resistant) cells.
Figure 105:
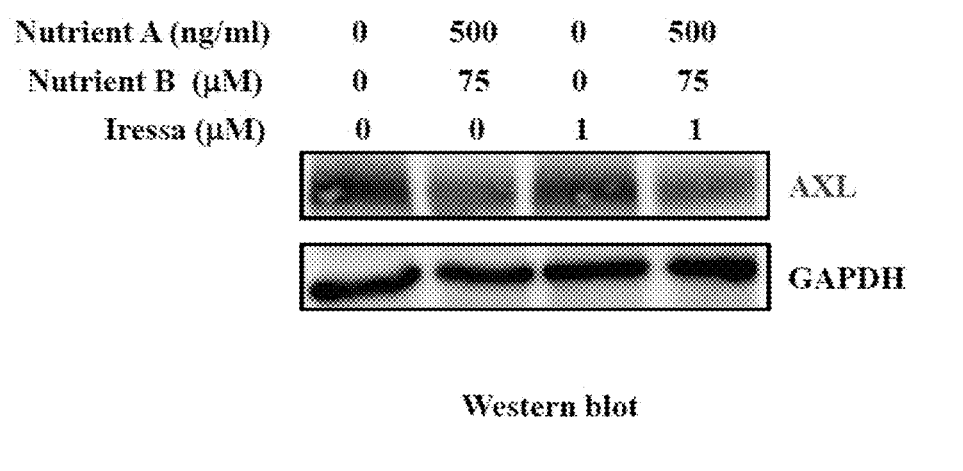
FIG. 105: Western blot of the combined effect of selenium (Nutrient A) and fish oil (Nutrient B) on AXL expression in drug (Iressa)-resistant HCC827GR cells. GAPDH is provided as a control.

In some embodiments of the inventive concept, Inventors have found that a nutritional supplement that includes fish oil and selenium is particularly effective in modifying AXL signaling in cells, particularly drug resistant tumor cells. As shown in FIG. 104, drug (Iressa)-resistant HCC827GR cells express elevated levels of both AXL and p-MET proteins relative to susceptible parent HCC827 cells. Surprisingly, Inventors have found that a combination of selenium yeast (Nutrient A) and fish oil (Nutrient B) dramatically reduces AXL expression in drug resistant HCC827GR (see FIG. 105). It should be appreciated that treatment with 1 μM Iressa had no effect.

Figure 106:
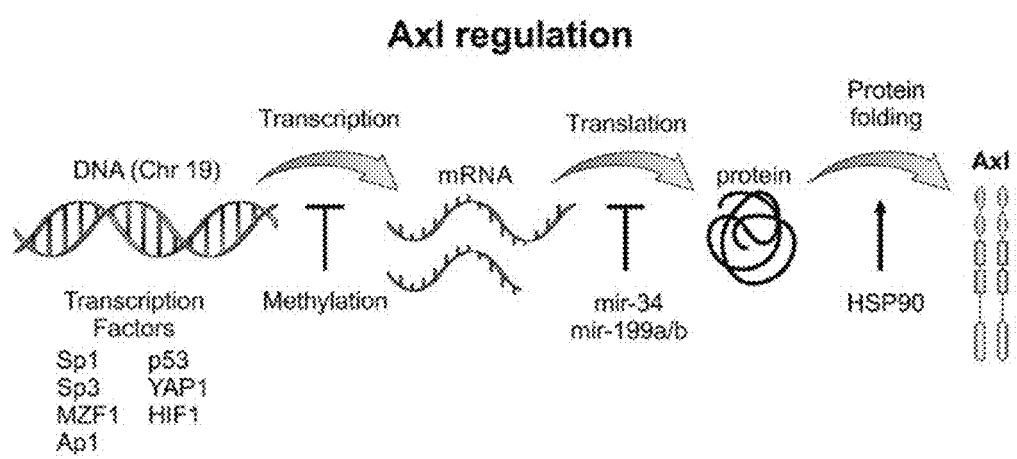
FIG. 106: Schematic depiction of the pathway for AXL protein expression, which provides various points for regulation of AXL expression.
Figure 107:
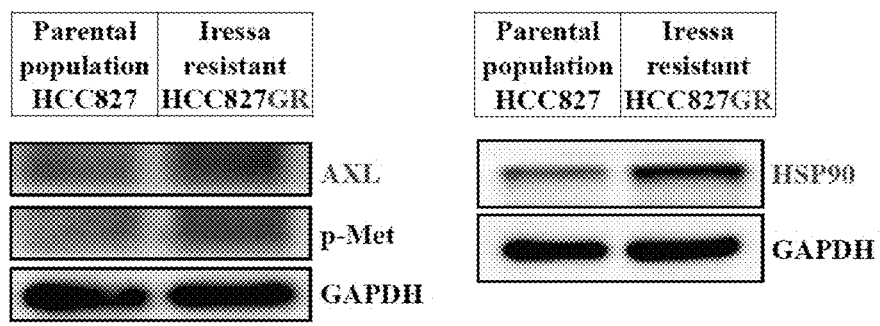
FIG. 107: Western blot of the expression of HSP90 and AXL in drug (Iressa)-resistant cells HCC827GR cells and in non-resistant parent HCC827 cells. GAPDH is provided as a control.

The Inventor has further investigated mechanisms by which the described nutritional supplement can be modulating AXL protein concentrations in the cell. FIG. 106 depicts the pathway of AXL expression, various points of which can be targeted to modulate AXL expression. As shown, AXL is dependent on heat shock protein 90 (HSP90) for proper folding. Improper protein folding can lead to increased rates of degradation. As shown in FIG. 107, both AXL and HSP90 protein levels are significantly elevated in drug (Iressa)-resistant HCC827GR tumor cells relative to non-resistant parent HCC827 cells.

Figure 108:
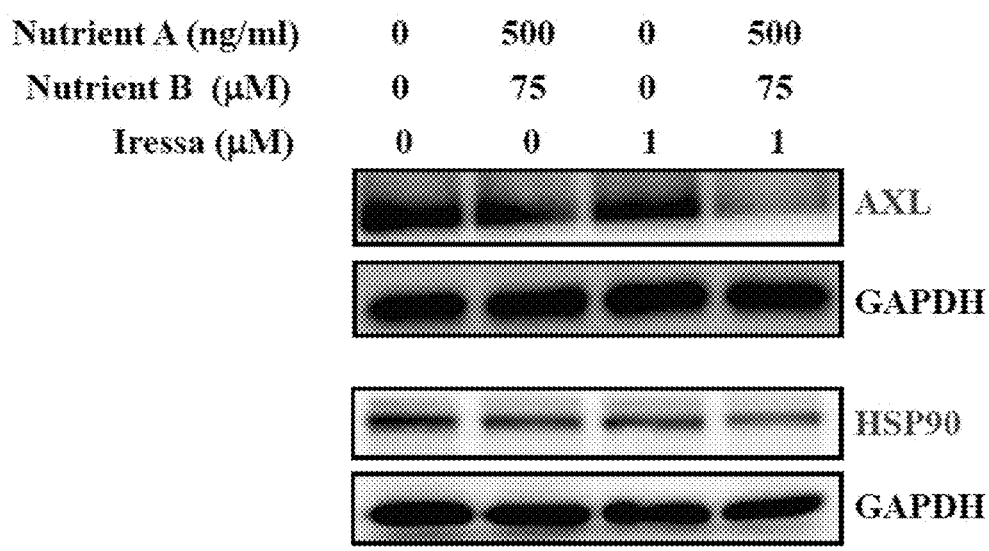
FIG. 108: Western blot showing reduction in AXL and HSP90 expression in drug (Iressa)-resistant tumor cells using a combination of selenium (Nutrient A) and fish oil (Nutrient B).

Surprisingly, the Inventor has found that a supplement containing a combination of selenium yeast (Nutrient A) and fish oil (Nutrient B) reduces both AXL and HSP90 in drug (Iressa)-resistant HCC827GR cells (see FIG. 108). A pronounced synergistic effect was also found when the combined nutritional supplement was used in combination with Iressa.

Figure 109:
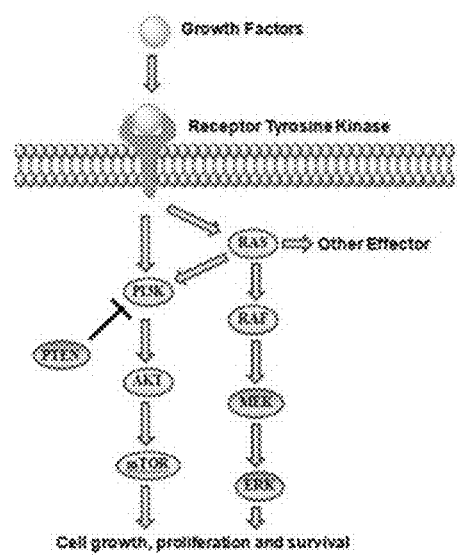
FIG. 109: Schematic depiction of the mTOR pathway.
Figure 110:
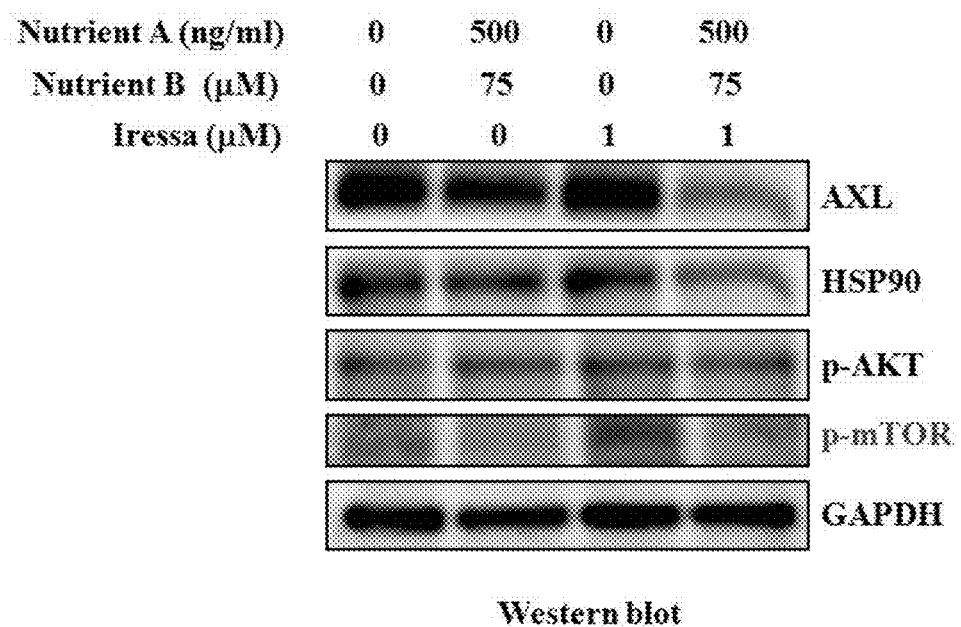
FIG. 110: Western blot showing reduction in AXL, HSP90, and p-mTOR expression in drug (Iressa)-resistant tumor cells using a combination of selenium (Nutrient A) and fish oil (Nutrient B).

The mTOR pathway has also been implicated in drug resistance in tumor cells. As shown in FIG. 109, mTOR can be phosphorylated in response to growth factors to impact cell growth and proliferation. Surprisingly, the Inventor has found that use of a supplement that combines selenium yeast (Nutrient A) and fish oil (Nutrient B) can reduce levels of p-mTOR in drug (Iressa)-resistant HCC827GR cells, both in the absence and the presence of the drug (see FIG. 110). Even more surprising, the combined nutritional supplement is able to reverse elevated p-mTOR levels in drug resistant cells that are treated with the chemotherapeutic agent.

Figure 111:
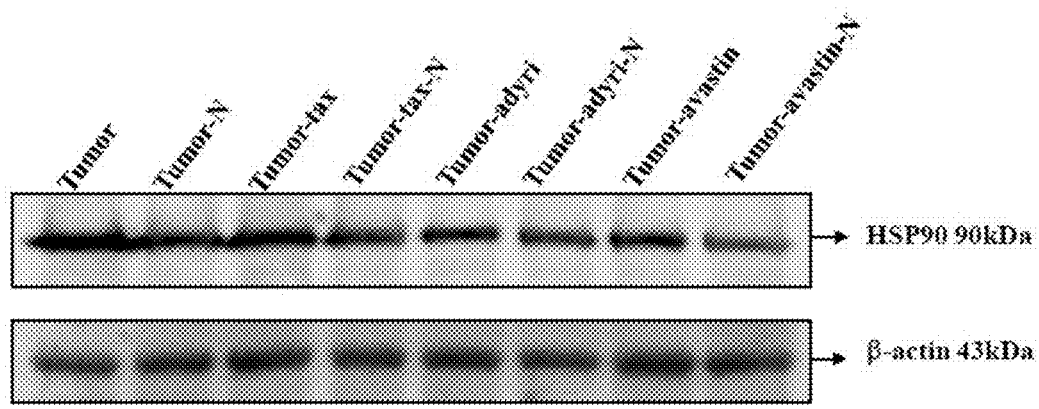
FIG. 111: Western blot showing the effects of treatment with a nutritional supplement containing fish oil and selenium alone and in combination with chemotherapeutic compounds on heat shock protein (HSP90) in tumor cells from in vivo models of human cancer.
Figure 112:
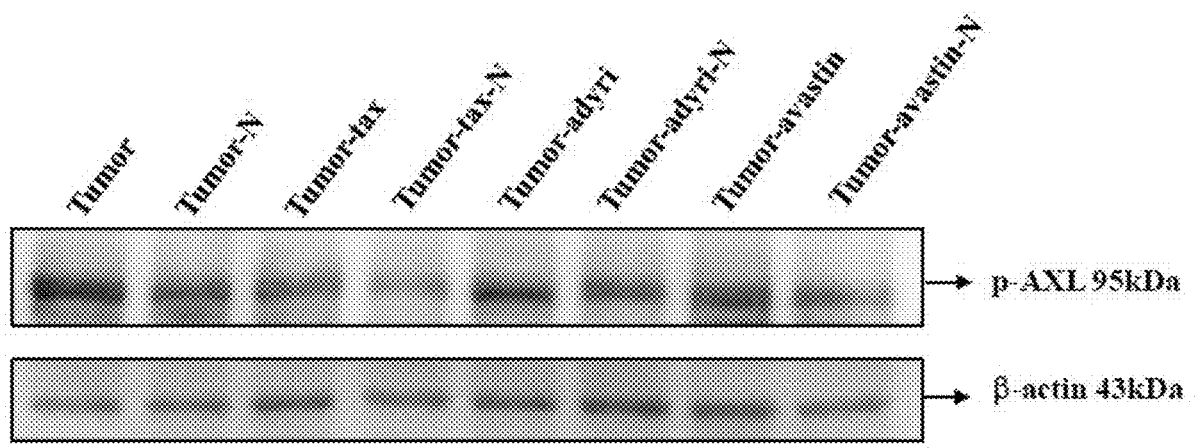
FIG. 112: Western blot showing the effects of treatment with a nutritional supplement containing fish oil and selenium alone and in combination with chemotherapeutic compounds on p-AXL in tumor cells from in vivo models of human cancer.

Studies of the effect of a nutritional supplement containing fish oil and selenium, both alone and in combination with chemotherapeutic agents, were also studied using in vivo animal models of triple negative human breast cancer. Results are shown in FIG. 111 and FIG. 112. Animals were treated with a nutritional supplement containing fish oil and selenium (for example, a formulation as described in Table 1), Taxol ("tax"), Adriamycin ("adyri"), Avastin, or a combination of the nutritional supplement and individual chemotherapeutic agents. As shown in FIG. 111, HSP90 expression (as determined by Western blot) in untreated tumor samples is high. Surprisingly, this is reduced to some extent by treatment with only a nutritional supplement containing fish oil and selenium. Treatment with Taxol has minimal impact on HSP90 expression, however a marked reduction is found when Taxol is used in combination with a nutritional supplement containing fish oil and selenium. Similar results are seen with Adrimaycin treatment and Adriamycin cotreatment with such a supplement. While HSP90 expression in such tumors is reduced to some extent by treatment with Avastin, combined treatment with Avastin and a nutritional supplement containing fish oil and selenium results in a drastic decrease in HSP90 expression, indicating a synergistic effect.

FIG. 112 shows the results of similar studies where p-AXL content of the tumor is characterized. As shown, p-AXL is evident in untreated tumors, and is surprisingly reduced on treatment with only a nutritional supplement containing fish oil and selenium. Treatment with Taxol alone reduces p-AXL expression, and this is reduced to almost non-detectable amounts by cotherapy with Taxol and a nutritional supplement containing fish oil and selenium (indicating a synergistic effect). Treatment with Adriamycin or Avastin alone provided little to no apparent reduction in p-AXL expression, where cotherapy of each of these drugs with such a supplement provided a large decrease in expression. Overall, it is apparent that use of a nutritional supplement containing fish oil and selenium can be effective in modifying AXL signaling (e.g. reducing expression of p-AXL and HSP90), and that such a supplement can be used in cotherapy with various chemotherapeutic drugs to achieve a synergistic effect in modifying such AXL signaling.

Survival

Figure 113:
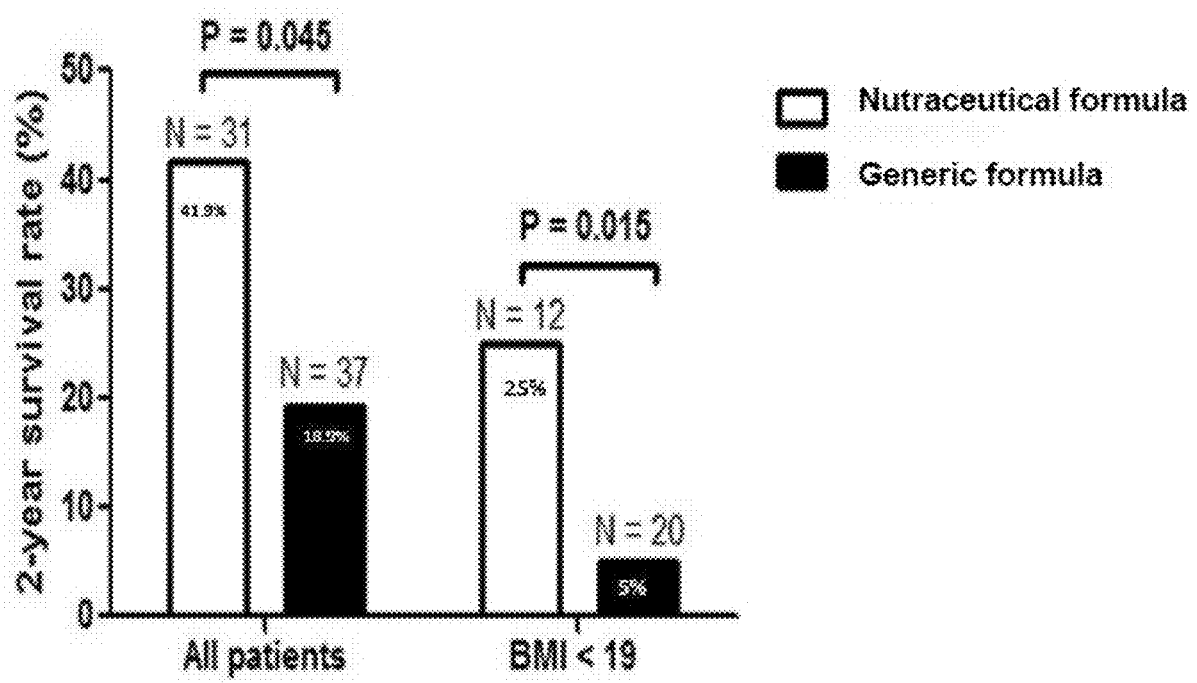
FIG. 113: Graph of two year survival rates of patients with head and neck cancers using a nutritional supplement containing fish oil and selenium and a generic prior art supplement.

As noted above, use of a nutritional supplement containing fish oil and selenium has numerous beneficial effects in regards to treatment of cancer, including reduction in tumor cell proliferation, tumor size and vascularization, resistance to chemotherapy, and metastasis. These effects are potentiated in a synergistic fashion by cotherapy with one or more chemotherapeutic agents. In addition, such supplements are able to reduce or reverse symptoms of cachexia associated with cancer, as well as modify plasma cytokine concentrations. Such benefits directly address many quality of life issues for persons living with cancer. In addition, the Inventor has found that use of a nutritional supplement containing fish oil and selenium also provide a direct benefit in regards to survival rate. As shown in FIG. 113, cancer patients receiving such a nutritional supplement ("Nutraceutical formulation") show over twice the two year survival rate of similarly treated patients receiving the caloric equivalent of a prior art supplement ("Generic formula"). When patients having a BMI of less than 19 are studied use of the nutritional supplement containing fish oil and selenium provides a 500% increase in two year survival rate relative to the generic formulation. The Inventor believes that use of a nutritional supplement that includes fish oil and selenium can provide a very significant improvement in survivability for cancer patients, particularly those with low BMI.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of generating a synergistic effect in enhancing the effectiveness of a cancer chemotherapeutic agent, comprising:
   administering the chemotherapeutic agent to an individual in need of treatment for cancer; and
   administering an effective amount of a nutritional supplement comprising selenium and fish oil comprising docosahexaenoic acid (DHA) to the individual in need of treatment for cancer, wherein the effective amount of the nutritional supplement provides amounts of fish oil and selenium effective to generate the synergistic effect in enhancing effect in with combination with the chemotherapeutic agent,
   wherein the synergistic effect provides a combined effect for the chemotherapeutic agent, fish oil, and selenium yeast that exceeds each of summation of individual effects of selenium, fish oil, and the chemotherapy agent, summation of an individual effect of selenium and combined effects of fish oil and the chemotherapeutic agent, summation of individual effects of fish oil and combined effects of selenium and the chemotherapeutic agent, and summation of individual effect of the chemotherapeutic agent and combined effects of fish oil and selenium on proliferation of a cancer cell,
   wherein the effective amount of the nutritional supplement is sufficient to provide 0.5 µg/mL to 300 µg/mL as the effective amount of selenium to the cancer cell and to provide 75 µM fish oil as the effective amount of fish oil to the cancer cell, and
   wherein the nutritional supplement comprises maltodextrin, 10,000 mg to 50,000 mg; whey protein isolate, 5,000 mg to 60,000 mg; whey protein concentrate, 1,000 mg to 50,000 mg; fructooligosaccharides/inulin, 40 mg to 15,000 mg; granulated honey, 1,000 mg to 9,000 mg; oat fiber, 500 mg to 15,000 mg; natural French Vanilla flavor, 500 mg to 20,000 mg; soy protein, 500 mg to 50,000 mg; brownulated powdered brown sugar, 500 mg to 10,000 mg; natural vanilla masking flavor, 500 mg to 5,000 mg; lecithin, 200 mg to 10,000 mg; milk, non-fat, 50 mg to 5,000 mg; rice protein powder, 50 mg to 5,000 mg; calcium caseinate, 50 mg to 2,000 mg; flax seed oil, 100 mg to 7,000 mg; canola oil, 100 mg to 7,000 mg; borage oil, 100 mg to 7,000 mg; olive oil, 100 mg to 7,000 mg; pure lemon oil, 100 mg to 1,000 mg; pure orange oil, 50 mg to 1,000 mg; mixed tocopherols, 0.5 mg to 200 mg; potassium phosphate, 200 mg to 1,500 mg; calcium carbonate, 100 mg to 5,000 mg; choline bitartrate, 150 mg to 2,500 mg; sodium chloride, 100 mg to 2,000 mg; calcium phosphate tribasic, 100 mg to 2,000 mg; ascorbic acid, 50 mg to 3,000 mg; potassium chloride, 50 mg to 2,000 mg; magnesium oxide, 50 mg to 500 mg; chromium yeast, 30 in to 3,000 in; molybdenum yeast, 30 µg to 2,000 in; inositol, 10 mg to 5,000 mg; zinc sulfate monohydrate, 5 mg to 200 mg; dry vitamin E acetate, 5 IU to 2,000 IU; niacinamide, 5 mg to 500 mg; ferric orthophosphate, 3 mg to 100 mg; calcium pantothenate, 3 mg to 200 mg; manganese sulfate monohydrate, 3 mg to 100 mg; beta carotene, 1 mg to 100 mg; copper gluconate, 1 mg to 15 mg; vitamin D3, 25

IU to 5,000 IU; vitamin K2, 2 μg to 1,000 μg; pyridoxine HCl, 0.5 mg to 200 mg; potassium iodide, 0.5 mg to 1,500 mg; riboflavin, 0.5 mg to 1,000 mg; thiamine hydrochloride, 0.5 mg to 2,500 mg; dry vitamin K1, 1 μg to 500 μg; vitamin A acetate, 500 IU to 100,000 IU; folic acid, 100 μg to 10,000 μg; d-biotin, 10 μg to 10,000 μg; vitamin B12, 1 μg to 3,000 μg; L-carnitine, 300 mg to 30,000 mg; L-glutamine, 500 mg to 60,000 mg; L-arginine base, 500 mg to 30,000 mg; taurine, 50 mg to 2,000 mg; L-lysine, 50 mg to 2,000 mg; alpha lipoic acid, 10 mg to 1,000 mg; resveratrol, 15 mg to 1,500 mg; co-enzyme Q10, 10 mg to 5,000 mg; glycine, 5 mg to 1,000 mg; proline, 5 mg to 1,000 mg; *Lact. acidophilus* (app. 10 billion total), 2 mg to 500 mg; Bifido bifidium (app. 10 billion total), 2 mg to 500 mg; *Lac. bulgaricus* (app. 10 billion total), 2 mg to 500 mg; Bifido *longum* (app. 10 billion total), 2 mg to 500 mg; *Strep. thermophilus* (app. 10 billion total), 2 mg to 500 mg; papain, 5 mg to 100 mg; pepsin, 5 mg to 100 mg; lipase, 5 mg to 100 mg; bromelain, 5 mg to 100 mg; pancreatin 4×, 0.5 mg to 100 mg; lactase, 1 mg to 100 mg; betaine HCl, 3 mg to 100 mg; pineapple juice powder, 2 mg to 500 mg; *papaya* fruit powder, 2 mg to 500 mg; quercetin, 30 mg to 3,000 mg; EGCG, 25 mg to 600 mg; OPC, 15 mg to 500 mg; anthocyanins, 15 mg to 5,000 mg; ellagic acid, 10 mg to 300 mg; astaxanthin, 2 mg to 90 mg; fucoidan, 20 mg to 1,500 mg; *Cordyceps,* 5 mg to 6,000 mg; *Ganoderma lucidum,* 15 mg to 10,000 mg; Shiitake, 40 mg to 15,000 mg; Maitake, 30 mg to 15,000 mg; and Turkey Tail, 30 mg to 15,000 mg.

2. The method of claim 1, wherein the chemotherapeutic agent is selected from the group consisting of gefitinib, erlotinib, pemetrexed, cisplatin, and docetaxel.

3. The method of claim 1, further comprising administering a plurality of chemotherapeutic compounds to the individual in need of treatment for cancer.

4. The method of claim 3, wherein the plurality of chemotherapeutic compounds is selected from the group consisting of gefitinib, erlotinib, pemetrexed, cisplatin, and docetaxel.

5. The method of claim 1, wherein the selenium is provided as a peptide or amino acid prepared from selenium yeast.

6. A method of increasing the effectiveness of a cancer chemotherapeutic agent, comprising:
administering a nutritional supplement comprising selenium and fish oil comprising docosahexaenoic acid (DHA) to an individual in need of treatment for cancer, wherein the nutritional supplement comprises
maltodextrin, 10,000 mg to 50,000 mg; whey protein isolate, 5,000 mg to 60,000 mg; whey protein concentrate, 1,000 mg to 50,000 mg; fructooligosaccharides/inulin, 40 mg to 15,000 mg; granulated honey, 1,000 mg to 9,000 mg; oat fiber, 500 mg to 15,000 mg; natural French Vanilla flavor, 500 mg to 20,000 mg; soy protein, 500 mg to 50,000 mg; brownulated powdered brown sugar, 500 mg to 10,000 mg; natural vanilla masking flavor, 500 mg to 5,000 mg; lecithin, 200 mg to 10,000 mg; milk, non-fat, 50 mg to 5,000 mg; rice protein powder, 50 mg to 5,000 mg; calcium caseinate, 50 mg to 2,000 mg; flax seed oil, 100 mg to 7,000 mg; canola oil, 100 mg to 7,000 mg; borage oil, 100 mg to 7,000 mg; olive oil, 100 mg to 7,000 mg; pure lemon oil, 100 mg to 1,000 mg; pure orange oil, 50 mg to 1,000 mg; mixed tocopherols, 0.5 mg to 200 mg; potassium phosphate, 200 mg to 1,500 mg; calcium carbonate, 100 mg to 5,000 mg; choline bitartrate, 150 mg to 2,500 mg; sodium chloride, 100 mg to 2,000 mg; calcium phosphate tribasic, 100 mg to 2,000 mg; ascorbic acid, 50 mg to 3,000 mg; potassium chloride, 50 mg to 2,000 mg; magnesium oxide, 50 mg to 500 mg; chromium yeast, 30 μg to 3,000 μg; molybdenum yeast, 30 μg to 2,000 μg; inositol, 10 mg to 5,000 mg; zinc sulfate monohydrate, 5 mg to 200 mg; dry vitamin E acetate, 5 IU to 2,000 IU; niacinamide, 5 mg to 500 mg; ferric orthophosphate, 3 mg to 100 mg; calcium pantothenate, 3 mg to 200 mg; manganese sulfate monohydrate, 3 mg to 100 mg; beta carotene, 1 mg to 100 mg; copper gluconate, 1 mg to 15 mg; vitamin D3, 25 IU to 5,000 IU; vitamin K2, 2 μg to 1,000 μg; pyridoxine HCl, 0.5 mg to 200 mg; potassium iodide, 0.5 mg to 1,500 mg; riboflavin, 0.5 mg to 1,000 mg; thiamine hydrochloride, 0.5 mg to 2,500 mg; dry vitamin K1, 1 μg to 500 μg; vitamin A acetate, 500 IU to 100,000 IU; folic acid, 100 μg to 10,000 μg; d-biotin, 10 μg to 10,000 μg; vitamin B12, 1 μg to 3,000 μg; L-carnitine, 300 mg to 30,000 mg; L-glutamine, 500 mg to 60,000 mg; L-arginine base, 500 mg to 30,000 mg; taurine, 50 mg to 2,000 mg; L-lysine, 50 mg to 2,000 mg; alpha lipoic acid, 10 mg to 1,000 mg; resveratrol, 15 mg to 1,500 mg; co-enzyme Q10, 10 mg to 5,000 mg; glycine, 5 mg to 1,000 mg; proline, 5 mg to 1,000 mg; *Lact. acidophilus* (app. 10 billion total), 2 mg to 500 mg; Bifido bifidium (app. 10 billion total), 2 mg to 500 mg; *Lac. bulgaricus* (app. 10 billion total), 2 mg to 500 mg; Bifido *longum* (app. 10 billion total), 2 mg to 500 mg; *Strep. thermophilus* (app. 10 billion total), 2 mg to 500 mg; papain, 5 mg to 100 mg; pepsin, 5 mg to 100 mg; lipase, 5 mg to 100 mg; bromelain, 5 mg to 100 mg; pancreatin 4×, 0.5 mg to 100 mg; lactase, 1 mg to 100 mg; betaine HCl, 3 mg to 100 mg; pineapple juice powder, 2 mg to 500 mg; *papaya* fruit powder, 2 mg to 500 mg; quercetin, 30 mg to 3,000 mg; EGCG, 25 mg to 600 mg; OPC, 15 mg to 500 mg; anthocyanins, 15 mg to 5,000 mg; ellagic acid, 10 mg to 300 mg; astaxanthin, 2 mg to 90 mg; fucoidan, 20 mg to 1,500 mg; *Cordyceps,* 5 mg to 6,000 mg; *Ganoderma lucidum,* 15 mg to 10,000 mg; Shiitake, 40 mg to 15,000 mg; Maitake, 30 mg to 15,000 mg; and Turkey Tail, 30 mg to 15,000 mg and is provided in an amount sufficient to provide 300 μg/mL selenium to a cancer cell and fish oil sufficient to provide 75 μM DHA to the cancer cell; and
administering the cancer chemotherapeutic agent to the individual in need of treatment for cancer,
wherein combined effects of cotherapy with the nutritional supplement and the cancer chemotherapeutic agent on cancer cell proliferation exceeds summation of individual effects of selenium, fish oil, and the chemotherapy drug on proliferation of the cancer cell.

7. The method of claim 6, wherein the cancer chemotherapeutic agent is selected from the group consisting of gefitinib, erlotinib, pemetrexed, cisplatin, and docetaxel.

8. The method of claim 6, wherein the pharmaceutical preparation comprises a plurality of cancer chemotherapeutic agents.

9. The method of claim 8, wherein the plurality of cancer chemotherapeutic agents is selected from the group consisting of gefitinib, erlotinib, pemetrexed, cisplatin, and docetaxel.

10. The method of claim 6, wherein the selenium is provided as a peptide or amino acid prepared from selenium yeast.

* * * * *